United States Patent
Glucksmann et al.

(12)

(10) Patent No.: US 6,780,627 B1
(45) Date of Patent: Aug. 24, 2004

(54) 22438, 23553, 25278, AND 26212 NOVEL HUMAN SULFATASES

(75) Inventors: Maria Alexandra Glucksmann, Lexington, MA (US); Mark Williamson, Saugus, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/495,823

(22) Filed: Jan. 31, 2000

(51) Int. Cl.[7] .............................. C12N 9/16; C12N 1/20; C12N 15/00; C12P 21/04; C07H 21/04

(52) U.S. Cl. ................. 435/196; 435/252.3; 435/320.1; 435/440; 435/71.1; 435/325; 536/23.2

(58) Field of Search .............................. 435/196, 252.3, 435/320.1, 71.1, 325, 440, 195; 536/23.2, 23.1

(56) References Cited

U.S. PATENT DOCUMENTS 6,210,883 B1    4/2001 Reed et al.

FOREIGN PATENT DOCUMENTS

WO    WO 99/46281    * 9/1999

OTHER PUBLICATIONS

Peters et al. Phylogenetic conservation of arylsulfatases. The J. Biol. Chem. vol. 265, pp. 3374–3381, 1990.*
Stein, C. et al., "Cloning and Expression of Human Arylsulfatase A," *The Journal of Biological Chemistry*, Jan. 15, 1989, pp. 1252–1259, vol. 264, Issue No. 2.

EMBL Database Report for Accession No. AB023218, Apr. 4, 1999 (XP–002181669).
EMBL Database Report for Accession No. A1423178, Mar. 15, 1999 (XP–002181670).
Blast Searches (6) for 22438 Sulfatase in NRN, Patent and NRP Databases.
Blast Searches (7) for 23553 Sulfatase in DBEST, NRN, Patent, and NRP Databases.
Blast Searches (7) for 25278 Sulfatase in DBEST, NRN, Patent, and NRP Databases.
Blast Searches (2) for 26212 Sulfatase in DBEST and NRN Databases.
Kikuno, R. et al., "Prediction of the Coding Sequences of Unidentified Human Genes. XIV. The Complete Sequences of 100 New cDNA Clones from Brain Which Code for Large Proteins in vitro," *DNA Research*, 1999, pp. 197–205, vol. 6.
NCB1 Sequence Viewer for Accession No. AB029000, Aug. 4, 1999.

* cited by examiner

*Primary Examiner*—Rebecca E. Prouty
*Assistant Examiner*—Yong D. Pak
(74) *Attorney, Agent, or Firm*—Millennium Pharmaceuticals, Inc.

(57) ABSTRACT

The present invention relates to newly identified human sulfatases. In particular, the invention relates to sulfatase polypeptides and polynucleotides, methods of detecting the sulfatase polypeptides and polynucleotides, and methods of diagnosing and treating sulfatase-related disorders. Also provided are vectors, host cells, and recombinant methods for making and using the novel molecules.

9 Claims, 25 Drawing Sheets

FIG. 1A.

Sequence length 2175

CACGCGTCCGCAAATTTCCTGATTCTTTTGAATTAGGATTCCAGATGGGGGCCTCATTTCTACAGCCCCCAACATTCCT
ATAGCCGTTATCACTGCCATCACCACTGCCACCAGCATCTTCTTGCAGATTCCACCCCTGCTCCCCAGAGACTTCCTGC
TTTGAAAGTGAGCAGAAAGGAAGCTCTCAGAAAAATCTCTAGTGGTGGCTGCCGTCGCTCCAGACAATCGGAATCCTGC

```
              M   G   W   L   F   L   K   V   L   L   A   G   V   S   F   S   G    17
CTTCACCACC   ATG GGC TGG CTT TTT CTA AAG GTT TTG TTG GCG GGA GTG AGT TTC TCA GGA    51
     F   L   Y   P   L   V   D   F   C   I   S   G   K   T   R   G   Q   K   P   N    37
    TTT CTT TAT CCT CTT GTG GAT TTT TGC ATC AGT GGG AAA ACA AGA GGA CAG AAG CCA AAC  111
     F   V   I   I   L   A   D   D   M   G   W   G   D   L   G   A   N   W   A   E    57
    TTT GTG ATT ATT TTG GCC GAT GAC ATG GGG TGG GGT GAC CTG GGA GCA AAC TGG GCA GAA  171
     T   K   D   T   A   N   L   D   K   M   A   S   E   G   M   R   F   V   D   F    77
    ACA AAG GAC ACT GCC AAC CTT GAT AAG ATG GCT TCG GAG GGA ATG AGG TTT GTG GAT TTC  231
     H   A   A   A   S   T   C   S   P   S   R   A   S   L   L   T   G   R   L   G    97
    CAT GCA GCT GCC TCC ACC TGC TCA CCC TCC CGG GCT TCC TTG CTC ACC GGC CGG CTT GGC  291
     L   R   N   G   V   T   R   N   F   A   V   T   S   V   G   G   L   P   L   N   117
    CTT CGC AAT GGA GTC ACA CGC AAC TTT GCA GTC ACT TCT GTG GGA GGC CTT CCG CTC AAC  351
     E   T   T   L   A   E   V   L   Q   Q   A   G   Y   V   T   G   I   I   G   K   137
    GAG ACC ACC TTG GCA GAG GTG CTG CAG CAG GCG GGT TAC GTC ACT GGG ATA ATA GGC AAA  411
     W   H   L   G   H   H   G   S   Y   H   P   N   F   R   G   F   D   Y   Y   F   157
    TGG CAT CTT GGA CAC CAC GGC TCT TAT CAC CCC AAC TTC CGT GGT TTT GAT TAC TAC TTT  471
     G   I   P   Y   S   H   D   M   G   C   T   D   T   P   G   Y   N   H   P   P   177
    GGA ATC CCA TAT AGC CAT GAT ATG GGC TGT ACT GAT ACT CCA GGC TAC AAC CAC CCT CCT  531
     C   P   A   C   P   Q   G   D   G   P   S   R   N   L   Q   R   D   C   Y   T   197
    TGT CCA GCG TGT CCA CAG GGT GAT GGA CCA TCA AGG AAC CTT CAA AGA GAC TGT TAC ACT  591
     D   V   A   L   P   L   Y   E   N   L   N   I   V   E   Q   P   V   N   L   S   217
    GAC GTG GCC CTC CCT CTT TAT GAA AAC CTC AAC ATT GTG GAG CAG CCG GTG AAC TTG AGC  651
     S   L   A   Q   K   Y   A   E   K   A   T   Q   F   I   Q   R   A   S   T   S   237
    AGC CTT GCC CAG AAG TAT GCT GAG AAA GCA ACC CAG TTC ATC CAG CGT GCA AGC ACC AGC  711
     G   R   P   F   L   L   Y   V   A   L   H   M   H   V   P   L   P   V   T   257
    GGG AGG CCC TTC CTG CTC TAT GTG GCT CTG GCC CAC ATG CAC GTG CCC TTA CCC GTG ACT  771
     Q   L   P   A   A   P   R   G   R   S   L   Y   G   A   G   L   W   E   M   D   277
    CAG CTA CCA GCA GCG CCA CGG GGC AGA AGC CTG TAT GGT GCA GGG CTC TGG GAG ATG GAC  831
     S   L   V   G   Q   I   K   D   K   V   D   H   T   V   K   E   N   T   F   L   297
    AGT CTG GTG GGC CAG ATC AAG GAC AAA GTT GAC CAC ACA GTG AAG GAA AAC ACA TTC CTC  891
     W   F   T   G   D   N   G   P   W   A   Q   K   C   E   L   A   G   S   V   G   317
    TGG TTT ACA GGA GAC AAT GGC CCG TGG GCT CAG AAG TGT GAG CTA GCG GGC AGT GTG GGT  951
     P   F   T   G   F   W   Q   T   R   Q   G   G   S   P   A   K   Q   T   T   W   337
    CCC TTC ACT GGA TTT TGG CAA ACT CGT CAA GGG GGA AGT CCA GCC AAG CAG ACG ACC TGG 1011
     E   G   G   H   R   V   P   A   L   A   Y   W   P   G   R   V   P   V   N   V   357
```

```
GAA GGA GGC CAC CGG GTC CCA GCA CTC CCA GCA CTG GCT TAC TGG CCT GGC AGA GTT CCA GTT AAT GTC   1071
 T   S   T   A   L   L   S   V   L   D   I   F   P   T   V   V   A   L   A   Q    377
ACC AGC ACT GCC TTG TTA AGC GTG CTG GAC ATT TTT CCA ACT GTG GTA GCC CTG GCC CAG   1131
 A   S   L   P   Q   G   R   R   F   D   G   V   D   V   S   E   V   L   F   G    397
GCC AGC TTA CCT CAA GGA CGG CGC TTT GAT GGT GTG GAC GTC TCC GAG GTG CTC TTT GGC   1191
 R   S   Q   P   G   H   R   V   L   F   H   P   N   S   G   A   A   G   E   F    417
CGG TCA CAG CCT GGG CAC AGG GTG CTG TTC CAC CCC AAC AGC GGG GCA GCT GGA GAG TTT   1251
 G   A   L   Q   T   V   R   L   E   R   Y   K   A   F   Y   I   T   G   G   A    437
GGA GCC CTG CAG ACT GTC CGC CTG GAG CGT TAC AAG GCC TTC TAC ATT ACC GGT GGA GCC   1311
 R   A   C   D   G   S   T   G   P   E   L   Q   H   K   F   P   L   I   F   N    457
AGG GCT TGT GAT GGG AGC ACG GGG CCT GAG CTG CAG CAT AAG TTT CCT CTG ATT TTC AAC   1371
 L   E   D   D   T   A   E   A   V   P   L   E   R   G   G   A   E   Y   Q   A    477
CTG GAA GAC GAT ACC GCA GAA GCT GTG CCC CTA GAA AGA GGT GGT GCG GAG TAC CAG GCT   1431
 V   L   P   E   V   R   K   V   L   A   D   V   L   Q   D   I   A   N   D   N    497
GTG CTG CCC GAG GTC AGA AAG GTT CTT GCA GAC GTC CTC CAA GAC ATT GCC AAC GAC AAC   1491
 I   S   S   A   D   Y   T   Q   D   P   S   V   T   P   C   C   N   P   Y   Q    517
ATC TCC AGC GCA GAT TAC ACT CAG GAC CCT TCA GTA ACT CCC TGC TGT AAT CCC TAC CAA   1551
 I   A   C   R   C   Q   A   A   *                                                 526
ATT GCC TGC CGC TGT CAA GCC GCA TAA                                                1578

CAGACCAATTTTTATTCCACGAGGAGGAGTACCTGGAAATTAGGCAAGTTTGCTTCCAAATTTCATTTTTACCCTCTTT
ACAAACACACGCTTTAGTTTAGTCTTGGAGTTTAGTTTTGGAGTTAGCCTTGCATATCCCTTCTGTATCCTGTCCCTCC
TCCACGCCGACCCGAGAGCAGCTGAGCTGCGCTGGCTCTGGGCACCCAGTGTGCCTTAATGGGAAGCACACGGGCTTTG
GAGTCAGGCACAGGTGCCAGCTCCAGCTTTTGAACTTGGGCAATTGTTTAACCTAACCTGCAAGTTGATTTTGAGGGTT
AAATAAAGGCATACATGAAAAAAAAAAAAAAAAAA
```

Prosite Pattern Matches

Prosite version: Release 12.2 of February 1995

>PS00001/PDOC00001/ASN_GLYCOSYLATION N-glycosylation site.

Query: 117 NETT 120
Query: 215 NLSS 218
Query: 356 NVTS 359
Query: 497 NISS 500

>PS00005/PDOC00005/PKC_PHOSPHO_SITE Protein kinase C phosphorylation site.

Query: 28 SGK 30
Query: 93 TGR 95
Query: 237 SGR 239
Query: 290 TVK 292
Query: 422 TVR 424

>PS00006/PDOC00006/CK2_PHOSPHO_SITE Casein kinase II phosphorylation site.

Query: 120 TLAE 123
Query: 290 TVKE 293
Query: 335 TTWE 338
Query: 364 SVLD 367
Query: 444 TGPE 447
Query: 499 SSAD 502

>PS00008/PDOC00008/MYRISTYL N-myristoylation site.

Query: 12 GVSFSG 17
Query: 33 GQKPNF 38
Query: 52 GANWAE 57
Query: 97 GLRNGV 102
Query: 113 GLPLNE 118
Query: 158 GIPYSH 163
Query: 328 GGSPAK 333
Query: 388 GVDVSE 393
Query: 418 GALQTV 423
Query: 435 GGARAC 440

>PS00009/PDOC00009/AMIDATION Amidation site.

Query: 382 QGRR 385

>PS00149/PDOC00117/SULFATASE_2 Sulfatases signature 2.

Query: 129 GYVTGIIGKW 138

FIG. 5A.

Input file Fbh23553fl.seq; Output File 23553.trans
Sequence length 4321

```
CCCACGCGTCCGGCTAATGAATCTTGGGGCCGGTGTCGGGCCGGGGCGGCTTGATCGGCAACTAGGAAACCCCAGGCGC
AGAGGCCAGGAGCGAGGGCAGCGAGGATCAGAGGCCAGGCCTTCCCGGCTGCCGGCGCTCCTCGGAGGTCAGGGCAGAT
GAGGAACATGACTCTCCCCCTTCGGAGGAGGAAGGAAGTCCCGCTGCCACCTTATCTCTGCTCCTCTGCCTCCTCCCTG
TTCCCAGAGCTTTTTCTCTAGAGAAGATTTTGAAGGCGGCTTTTGTGCTGACGGCCACCCACCATCATCTAAAGAAGAT
AAACTTGGCAAATGACATGCAGGTTCTTCAAGGCAGAATAATTGCAGAAAATCTTCAAAGGACCCTATCTGCAGATGTT
CTGAATACCTCTGAGAATAGAGATTGATTATTCAACCAGGATACCTAATTCAAGAACTCCAGAAATCAGGAGACGGAGA
```

| | | | | | | M | K | Y | S | C | C | A | L | V | L | A | 11 |
|---|---|---|---|---|---|---|---|---|---|---|---|---|---|---|---|---|---|
| CATTTTGTCAGTTTTGCAACATTGGACCAAATACA | | | | | | ATG | AAG | TAT | TCT | TGC | TGT | GCT | CTG | GTT | TTG | GCT | 33 |

| V | L | G | T | E | L | L | G | S | L | C | S | T | V | R | S | P | R | F | R | 31 |
|---|---|---|---|---|---|---|---|---|---|---|---|---|---|---|---|---|---|---|---|---|
| GTC | CTG | GGC | ACA | GAA | TTG | CTG | GGA | AGC | CTC | TGT | TCG | ACT | GTC | AGA | TCC | CCG | AGG | TTC | AGA | 93 |

| G | R | I | Q | Q | E | R | K | N | I | R | P | N | I | I | L | V | L | T | D | 51 |
|---|---|---|---|---|---|---|---|---|---|---|---|---|---|---|---|---|---|---|---|---|
| GGA | CGG | ATA | CAG | CAG | GAA | CGA | AAA | AAC | ATC | CGA | CCC | AAC | ATT | ATT | CTT | GTG | CTT | ACC | GAT | 153 |

| D | Q | D | V | E | L | G | S | L | Q | V | M | N | K | T | R | K | I | M | E | 71 |
|---|---|---|---|---|---|---|---|---|---|---|---|---|---|---|---|---|---|---|---|---|
| GAT | CAA | GAT | GTG | GAG | CTG | GGG | TCC | CTG | CAA | GTC | ATG | AAC | AAA | ACG | AGA | AAG | ATT | ATG | GAA | 213 |

| H | G | A | T | F | I | N | A | F | V | T | T | P | M | C | C | P | S | R | 91 |
|---|---|---|---|---|---|---|---|---|---|---|---|---|---|---|---|---|---|---|---|
| CAT | GGG | GGG | GCC | ACC | TTC | ATC | AAT | GCC | TTT | GTG | ACT | ACA | CCC | ATG | TGC | TGC | CCG | TCA | CGG | 273 |

| S | S | M | L | T | G | K | Y | V | H | N | H | N | V | Y | T | N | N | E | N | 111 |
|---|---|---|---|---|---|---|---|---|---|---|---|---|---|---|---|---|---|---|---|---|
| TCC | TCC | ATG | CTC | ACC | GGG | AAG | TAT | GTG | CAC | AAT | CAC | AAT | GTC | TAC | ACC | AAC | AAC | GAG | AAC | 333 |

| C | S | S | P | S | W | Q | A | M | H | E | P | R | T | F | A | V | Y | L | N | 131 |
|---|---|---|---|---|---|---|---|---|---|---|---|---|---|---|---|---|---|---|---|---|
| TGC | TCT | TCC | CCC | TCG | TGG | CAG | GCC | ATG | CAT | GAG | CCT | CGG | ACT | TTT | GCT | GTA | TAT | CTT | AAC | 393 |

| N | T | G | Y | R | T | A | F | F | G | K | Y | L | N | E | Y | N | G | S | Y | 151 |
|---|---|---|---|---|---|---|---|---|---|---|---|---|---|---|---|---|---|---|---|---|
| AAC | ACT | GGC | TAC | AGA | ACA | GCC | TTT | TTT | GGA | AAA | TAC | CTC | AAT | GAA | TAT | AAT | GGC | AGC | TAC | 453 |

| I | P | P | G | W | R | E | W | L | G | L | I | K | N | S | R | F | Y | N | Y | 171 |
|---|---|---|---|---|---|---|---|---|---|---|---|---|---|---|---|---|---|---|---|---|
| ATC | CCC | CCT | GGG | TGG | CGA | GAA | TGG | CTT | GGA | TTA | ATC | AAG | AAT | TCT | CGC | TTC | TAT | AAT | TAC | 513 |

| T | V | C | R | N | G | I | K | E | K | H | G | F | D | Y | A | K | D | Y | F | 191 |
|---|---|---|---|---|---|---|---|---|---|---|---|---|---|---|---|---|---|---|---|---|
| ACT | GTT | TGT | CGC | AAT | GGC | ATC | AAA | GAA | AAG | CAT | GGA | TTT | GAT | TAT | GCA | AAG | GAC | TAC | TTC | 573 |

| T | D | L | I | T | N | E | S | I | N | Y | F | K | M | S | K | R | M | Y | P | 211 |
|---|---|---|---|---|---|---|---|---|---|---|---|---|---|---|---|---|---|---|---|---|
| ACA | GAC | TTA | ATC | ACT | AAC | GAG | AGC | ATT | AAT | TAC | TTC | AAA | ATG | TCT | AAG | AGA | ATG | TAT | CCC | 633 |

| H | R | P | V | M | M | V | I | S | H | A | A | P | H | G | P | E | D | S | A | 231 |
|---|---|---|---|---|---|---|---|---|---|---|---|---|---|---|---|---|---|---|---|---|
| CAT | AGG | CCC | GTT | ATG | ATG | GTG | ATC | AGC | CAC | GCT | GCG | CCC | CAC | GGC | CCC | GAG | GAC | TAC | GCC | 693 |

| P | Q | F | S | K | L | Y | P | N | A | S | Q | H | I | T | P | S | Y | N | Y | 251 |
|---|---|---|---|---|---|---|---|---|---|---|---|---|---|---|---|---|---|---|---|---|
| CCA | CAG | TTT | TCT | AAA | CTG | TAC | CCC | AAT | GCT | TCC | CAA | CAC | ATA | ACT | CCT | AGT | TAT | AAC | TAT | 753 |

| A | P | N | M | D | K | H | W | I | M | Q | Y | T | G | P | M | L | P | I | H | 271 |
|---|---|---|---|---|---|---|---|---|---|---|---|---|---|---|---|---|---|---|---|---|
| GCA | CCA | AAT | ATG | GAT | AAA | CAC | TGG | ATT | ATG | CAG | TAC | ACA | GGA | CCA | ATG | CTG | CCC | ATC | CAC | 813 |

| M | E | F | T | N | I | L | Q | R | K | R | L | Q | T | L | M | S | V | D | D | 291 |
|---|---|---|---|---|---|---|---|---|---|---|---|---|---|---|---|---|---|---|---|---|
| ATG | GAA | TTT | ACA | AAC | ATT | CTA | CAG | CGC | AAA | AGG | CTC | CAG | ACT | TTG | ATG | TCA | GTG | GAT | GAT | 873 |

| S | V | E | R | L | Y | N | M | L | V | E | T | G | E | L | E | N | T | Y | I | 311 |

FIG. 5B.

```
                        TCT GTG GAG AGG CTG TAT AAC ATG CTC GTG GAG ACG GGG GAG CTG GAG AAT ACT TAC ATC  933
 I   Y   T   A   D   H   G   Y   H   I   G   Q   F   G   L   V   K   G   K   S    331
ATT TAC ACC GCC GAC CAT GGT TAC CAT ATT GGG CAG TTT GCA CTG GTC AAG GGG AAA TCC  993
 M   P   Y   D   F   D   I   R   V   P   F   F   I   R   G   P   S   V   E   P   351
ATG CCA TAT GAC TTT GAT ATT CGT GTG CCT TTT TTT ATT CGT GGT CCA AGT GTA GAA CCA 1053
 G   S   I   V   P   Q   I   V   L   N   I   D   L   A   P   T   I   L   D   I   371
GGA TCA ATA GTC CCA CAG ATC GTT CTC AAC ATT GAC TTG GCC CCC ACG ATC CTG GAT ATT 1113
 A   G   L   D   T   P   P   D   V   D   G   K   S   V   L   K   L   L   D   P   391
GCT GGG CTC GAC ACA CCT CCT GAT GTG GAC GGC AAG TCT GTC CTC AAA CTT CTG GAC CCA 1173
 E   K   P   G   N   R   F   R   T   N   K   K   A   K   I   W   R   D   T   F   411
GAA AAG CCA GGT AAC AGG TTT CGA ACA AAC AAG AAG GCC AAA ATT TGG CGT GAT ACA TTC 1233
 L   V   E   R   G   K   F   L   R   K   K   E   E   S   S   K   N   I   Q   Q   431
CTA GTG GAA AGA GGC AAA TTT CTA CGT AAG AAG GAA GAA TCC AGC AAG AAT ATC CAA CAG 1293
 S   N   H   L   P   K   Y   E   R   V   K   E   L   C   Q   Q   A   R   Y   Q   451
TCA AAT CAC TTG CCC AAA TAT GAA CGG GTC AAA GAA CTA TGC CAG CAG GCC AGG TAC CAG 1353
 T   A   C   E   Q   P   G   Q   K   W   Q   C   I   E   D   T   S   G   K   L   471
ACA GCC TGT GAA CAA CCG GGG CAG AAG TGG CAA TGC ATT GAG GAT ACA TCT GGC AAG CTT 1413
 R   I   H   K   C   K   G   P   S   D   L   L   T   V   R   Q   S   T   R   N   491
CGA ATT CAC AAG TGT AAA GGA CCC AGT GAC CTG CTC ACA GTC CGG CAG AGC ACG CGG AAC 1473
 L   Y   A   R   G   F   H   D   K   D   K   E   C   S   C   R   E   S   G   Y   511
CTC TAC GCT CGC GGC TTC CAT GAC AAA GAC AAA GAG TGC AGT TGT AGG GAG TCT GGT TAC 1533
 R   A   S   R   S   Q   R   K   S   Q   R   Q   F   L   R   N   Q   G   T   P   531
CGT GCC AGC AGA AGC CAA AGA AAG AGT CAA CGG CAA TTC TTG AGA AAC CAG GGG ACT CCA 1593
 K   Y   K   P   R   F   V   H   T   R   Q   T   R   S   L   S   V   E   F   E   551
AAG TAC AAG CCC AGA TTT GTC CAT ACT CGG CAG ACA CGT TCC TTG TCC GTC GAA TTT GAA 1653
 G   E   I   Y   D   I   N   L   E   E   E   E   E   L   Q   V   L   Q   P   R   571
GGT GAA ATA TAT GAC ATA AAT CTG GAA GAA GAA GAA GAA TTG CAA GTG TTG CAA CCA AGA 1713
 N   I   A   K   R   H   D   E   G   H   K   G   P   R   D   L   Q   A   S   S   591
AAC ATT GCT AAG CGT CAT GAT GAA GGC CAC AAG GGG CCA AGA GAT CTC CAG GCT TCC AGT 1773
 G   G   N   R   G   R   M   L   A   D   S   S   N   A   V   G   P   P   T   T   611
GGT GGC AAC AGG GGC AGG ATG CTG GCA GAT AGC AGC AAC GCC GTG GGC CCA CCT ACC ACT 1833
 V   R   V   T   H   K   C   F   I   L   P   N   D   S   I   H   C   E   R   E   631
GTC CGA GTG ACA CAC AAG TGT TTT ATT CTT CCC AAT GAC TCT ATC CAT TGT GAG AGA GAA 1893
 L   Y   Q   S   A   R   A   W   K   D   H   K   A   Y   I   D   K   E   I   E   651
CTG TAC CAA TCG GCC AGA GCG TGG AAG GAC CAT AAG GCA TAC ATT GAC AAA GAG ATT GAA 1953
 A   L   Q   D   K   I   K   N   L   R   E   V   R   G   H   L   K   R   R   K   671
GCT CTG CAA GAT AAA ATT AAG AAT TTA AGA GAA GTG AGA GGA CAT CTG AAG AGA AGG AAG 2013
 P   E   E   C   S   C   S   K   Q   S   Y   Y   N   K   E   K   G   V   K   K   291
CCT GAG GAA TGT AGC TGC AGT AAA CAA AGC TAT TAC AAT AAA GAG AAA GGT GTA AAA AAG 2073
 Q   E   K   L   K   S   H   L   H   P   F   K   E   A   A   Q   E   V   D   S   711
CAA GAG AAA TTA AAG AGC CAT CTT CAC CCA TTC AAG GAG GCT GCT CAG GAA GTA GAT AGC 2133
```

FIG. 5C.

```
  K   L   Q   L   F   K   E   N   N   R   R   R   K   K   E   R   K   E   K   R   731
 AAA CTG CAA CTT TTC AAG GAG AAC AAC CGT AGG AGG AAG AAG GAG AGG AAG GAG AAG AGA 2193
  R   Q   R   K   G   E   E   C   S   L   P   G   L   T   C   F   T   H   D   N   751
 CGG CAG AGG AAG GGG GAA GAG TGC AGC CTG CCT GGC CTC ACT TGC TTC ACG CAT GAC AAC 2253
  N   H   W   Q   T   A   P   F   W   N   L   G   S   F   C   A   C   T   S   S   771
 AAC CAC TGG CAG ACA GCC CCG TTC TGG AAC CTG GGA TCT TTC TGT GCT TGC ACG AGT TCT 2313
  N   N   N   T   Y   W   C   L   R   T   V   N   E   T   H   N   F   L   F   C   791
 AAC AAT AAC ACC TAC TGG TGT TTG CGT ACA GTT AAT GAG ACG CAT AAT TTT CTT TTC TGT 2373
  E   F   A   T   G   F   L   E   Y   F   D   M   N   T   D   P   Y   Q   L   T   811
 GAG TTT GCT ACT GGC TTT TTG GAG TAT TTT GAT ATG AAT ACA GAT CCT TAT CAG CTC ACA 2433
  N   T   V   H   T   V   E   R   G   I   L   N   Q   L   H   V   Q   L   M   E   831
 AAT ACA GTG CAC ACG GTA GAA CGA GGC ATT TTG AAT CAG CTA CAC GTA CAA CTA ATG GAG 2493
  L   R   S   C   Q   G   Y   K   Q   C   N   P   R   P   K   N   L   D   V   G   851
 CTC AGA AGC TGT CAA GGA TAT AAG CAG TGC AAC CCA AGA CCT AAG AAT CTT GAT GTT GGA 2553
  N   K   D   G   G   S   Y   D   L   H   R   G   Q   L   W   D   G   W   E   G   871
 AAT AAA GAT GGA GGA AGC TAT GAC CTA CAC AGA GGA CAG TTA TGG GAT GGA TGG GAA GGT 2613
  *                                                                               872
 TAA                                                                              2616
```

TCAGCCCCGTCTCACTGCAGACATCAACTGGCAAGGCCTAGAGGAGCTACACAGTGTGAATGAAAACATCTATGAGTAC
AGACAAAACTACAGACTTAGTCTGGTGGACTGGACTAATTACTTGAAGGATTTAGATAGAGTATTTGCACTGCTGAAGA
GTCACTATGAGCAAAATAAAACAAATAAGACTCAAACTGCTCAAAGTGACGGGTTCTTGGTTGTCTCTGCTGAGCACGC
TGTGTCAATGGAGATGGCCTCTGCTGACTCAGATGAAGACCCAAGGCATAAGGTTGGGAAAACACCTCATTTGACCTTG
CCAGCTGACCTTCAAACCCTGCATTTGAACCGACCAACATTAAGTCCAGAGAGTAAACTTGAATGGAATAACGACATTC
CAGAAGTTAATCATTTGAATTCTGAACACTGGAGAAAAACCGAAAAATGGACGGGGCATGAAGAGACTAATCATCTGGA
AACCGATTTCAGTGGCGATGGCATGACAGAGCTAGAGCTCGGGCCCAGCCCCAGGCTGCAGCCCATTCGCAGGCACCCG
AAAGAACTTCCCCAGTATGGTGGTCCTGGAAAGGACATTTTTGAAGATCAACTATATCTTCCTGTGCATTCCGATGGAA
TTTCAGTTCATCAGATGTTCACCATGGCCACCGCAGAACACCGAAGTAATTCCAGCATAGCGGGGAAGATGTTGACCAA
GGTGGAGAAGAATCACGAAAAGGAGAAGTCACAGCACCTAGAAGGCAGCGCCTCCTCTTCACTCTCCTCTGATTAGATG
AAACTGTTACCCTTACCTAAACACAGTATTTCTTTTTAACTTTTTTATTTGTAAACTAATAAAGGKAATCACAGCCACC
AACATTCCAAGCTACCCTGGGTACCTTTGTGCAGTAGAAGCTAGTGAGCATGTGAGCAAGCGGTGTGCACACGGAGACT
CATCGTTATAATTTACTATCTGCCAAGGAGTAGAAAGAAAGGCTGGGGATATTTGGGTTGGCTTTGGKTTTGATTTTTT
GCTTGGTTGGTTGGTTTGKACTAAAACAGTATTATCTTTTGAATATCGTAGGGACATAARKWWWWMMWKKTWVTCMAW
YMHRAKAKGSYWRRAWKGGGSTYTYTSKKRKSTMWAMWYKWSCHCCYSKKRWWAWTYWYWMMYWCMYKYTSSSTGRYKRN
KTAATGAAGTT

Prosite Pattern Matches for 23553

Prosite versions: Release 12.2 of February 1995

>PS00001/PDOC00001/ASN_GLYCOSYLATION N-glycosylation site.

| | | |
|---|---|---|
| Query: 64 | NKTR | 67 |
| Query: 111 | NCSS | 114 |
| Query: 131 | NNTG | 134 |
| Query: 148 | NGSY | 151 |
| Query: 170 | NYTV | 173 |
| Query: 197 | NESI | 200 |
| Query: 240 | NASQ | 243 |
| Query: 623 | NDSI | 626 |
| Query: 773 | NNTY | 776 |
| Query: 783 | NETH | 786 |

>PS00005/PDOC00005/PKC_PHOSPHO_SITE Protein kinase C phosphorylation site.

| | | |
|---|---|---|
| Query: 24 | TVR | 26 |
| Query: 27 | SPR | 29 |
| Query: 66 | TRK | 68 |
| Query: 96 | TGK | 98 |
| Query: 206 | SKR | 208 |
| Query: 400 | TNK | 402 |
| Query: 425 | SSK | 427 |
| Query: 468 | SGK | 470 |
| Query: 484 | TVR | 486 |
| Query: 488 | STR | 490 |
| Query: 505 | SCR | 507 |
| Query: 516 | SQR | 518 |
| Query: 520 | SQR | 522 |
| Query: 530 | TPK | 532 |
| Query: 611 | TVR | 613 |
| Query: 615 | THK | 617 |
| Query: 635 | SAR | 637 |

>PS00006/PDOC00006/CK2_PHOSPHO_SITE Casein kinase II phosphorylation site.

| | | |
|---|---|---|
| Query: 107 | TNNE | 110 |
| Query: 288 | SVDO | 291 |
| Query: 367 | TILD | 370 |
| Query: 376 | TPPD | 379 |
| Query: 452 | TACE | 455 |
| Query: 505 | SCRE | 508 |
| Query: 781 | TVNE | 784 |

FIG. 8A.

\>PS00007/PDOC00007/TYR_PHOSPHO_SITE Tyrosine kinase phosphorylation site.

Query: 637   RAWKDHKAY   645

\>PS00008/PDOC00008/MYRISTYL N-myristoylation site.

Query:  19   GSLCST  24
Query: 161   GLIKNS 166
Query: 325   GLVKGK 330
Query: 592   GGNRGR 597
Query: 763   GSFCAC 768
Query: 851   GNKDGG 856

\>PS00523/PDOC00117/SULFATASE_1 Sulfatases signature 1.

Query: 85   PMCCPSRSSMLTG   97

FIG. 8B.

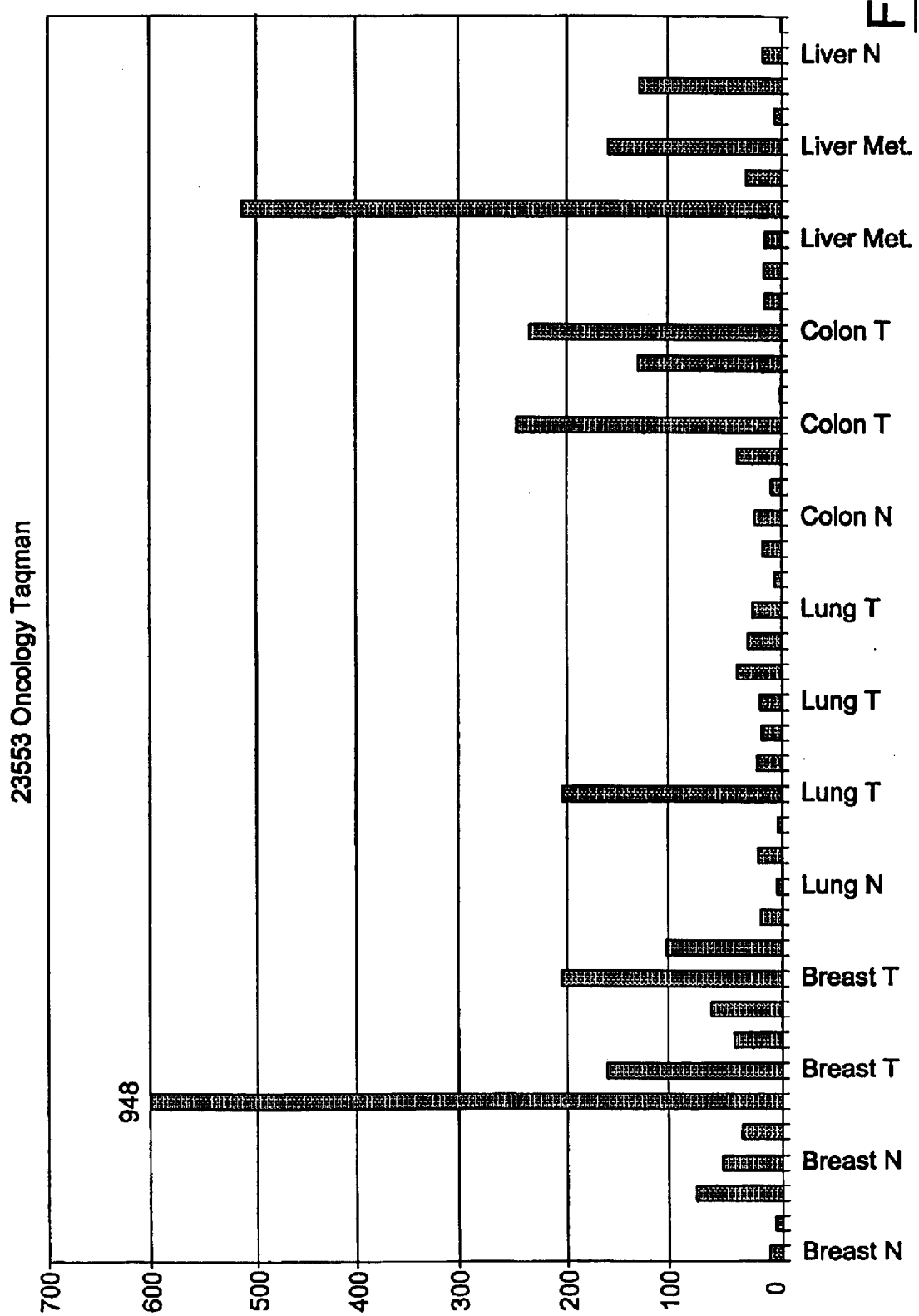

Input file Fbh25278FL1.seq  Output File 25278.trans
Sequence length 2940

FIG. 10A.

```
CCACGCGTCCGCCCACGCGTCCGGCTGCCACGCCGCGTCTCAGGCTGGCCGGGCTGAGCCGGGGAAGAGGGAGCAAAGG
CGGCGCAGGGCCTGCGCTTAGGCAGCGGGAGGCAGCTCGGCGCGGGCCTGACCTCCCCAGAGCGCCCCGCTGCGGCCGA
GCAGATCCGGCCCAGCCGTCCGGCAGCCAGTCCCGGACCAGACACTGGACCGTCCCCGGGGGCGCTGAACTCCTCGC
AGCATCCGAGCCGGCGGGCCGGTGGTGCGCCCTGGGCGCGCGAGGTGGTGAGGCCCCAGGAGCCCGGCGCGCCGGGACA
```

|  |  |  |  |  |  |  |  |  |  |  |  |  |  |  | M | H | T | L | T | G | F | S | L | V | S | L | L | S | F | 15 |
| CGCGGGCCGGCTTGGCG | ATG | CAC | ACC | CTC | ACT | GGC | TTC | TCT | CTG | GTC | AGC | CTG | CTC | AGC | TTC | 45 |

```
  G   Y   L   S   W   D   W   A   K   P   S   F   V   A   D   G   P   G   E   A    35
  GGC TAC CTG TCC TGG GAC TGG GCC AAG CCG AGC TTC GTG GCC GAC GGG CCC GGG GAG GCT  105

G   E   Q   P   S   A   A   P   P   Q   P   P   H   I   I   F   I   L   T   D    55
  GGC GAG CAG CCC TCG GCC GCT CCG CCC CAG CCT CCC CAC ATC ATC TTC ATC CTC ACG GAC  165

D   Q   G   Y   H   D   V   G   Y   H   G   S   D   I   E   T   P   T   L   D    75
  GAC CAA GGC TAC CAC GAC GTG GGC TAC CAT GGT TCA GAT ATC GAG ACC CCT ACG CTG GAC  225

R   L   A   A   K   G   V   K   L   E   N   Y   Y   I   Q   P   I   C   T   P    95
  AGG CTG GCG GCC AAG GGG GTC AAG TTG GAG AAT TAT TAC ATC CAG CCC ATC TGC ACG CCT  285

S   R   S   Q   L   L   T   G   R   Y   Q   I   H   T   G   L   Q   H   S   I   115
  TCG CGG AGC CAG CTC CTC ACT GGC AGG TAC CAG ATC CAC ACA GGA CTC CAG CAT TCC ATC  345

I   R   P   Q   Q   P   N   C   L   P   L   D   Q   V   T   L   P   Q   K   L   135
  ATC CGC CCA CAG CAG CCC AAC TGC CTG CCC CTG GAC CAG GTG ACA CTG CCA CAG AAG CTG  405

Q   E   A   G   Y   S   T   H   M   V   G   K   W   H   L   G   F   Y   R   K   155
  CAG GAG GCA GGT TAT TCC ACC CAT ATG GTG GGC AAG TGG CAC CTG GGC TTC TAC CGG AAG  465

E   C   L   P   T   R   R   G   F   D   T   F   L   G   S   L   T   G   N   V   175
  GAG TGT CTG CCC ACC CGT CGG GGC TTC GAC ACC TTC CTG GGC TCG CTC ACG GGC AAT GTG  525

D   Y   Y   T   Y   D   N   C   D   G   P   G   V   C   G   F   D   L   H   E   195
  GAC TAT TAC ACC TAT GAC AAC TGT GAT GGC CCA GGC GTG TGC GGC TTC GAC CTG CAC GAG  585

G   E   N   V   A   W   G   L   S   G   Q   Y   S   T   M   L   Y   A   Q   R   215
  GGT GAG AAT GTG GCC TGG GGG CTC AGC GGC CAG TAC TCC ACT ATG CTT TAC GCC CAG CGC  645

A   S   H   I   L   A   S   H   S   P   Q   R   P   L   F   L   Y   V   A   F   235
  GCC AGC CAT ATC CTG GCC AGC CAC AGC CCT CAG CGT CCC CTC TTC CTC TAT GTG GCC TTC  705

Q   A   V   H   T   P   L   Q   S   P   R   E   Y   L   Y   R   Y   R   T   M   255
  CAG GCA GTA CAC ACA CCC CTG CAG TCC CCT CGT GAG TAC CTG TAC CGC TAC CGC ACC ATG  765

G   N   V   A   R   R   K   Y   A   A   M   V   T   C   M   D   E   A   V   R   275
  GGC AAT GTG GCC CGG CGG AAG TAC GCG GCC ATG GTG ACC TGC ATG GAT GAG GCT GTG CGC  825

N   I   T   W   A   L   K   R   Y   G   F   Y   N   N   S   V   I   I   F   S   295
  AAC ATC ACC TGG GCC CTC AAG CGC TAC GGT TTC TAC AAC AAC AGT GTC ATC ATC TTC TCC  885

S   D   N   G   G   Q   T   F   S   G   G   S   N   W   P   L   R   G   R   K   315
  AGT GAC AAT GGT GGC CAG ACT TTC TCG GGG GGC AGC AAC TGG CCG CTC CGA GGA CGC AAG  945

G   T   Y   W   E   G   G   V   R   G   L   G   F   V   H   S   P   L   L   K   335
  GGC ACT TAT TGG GAA GGT GGC GTG CGG GGC CTA GGC TTT GTC CAC AGT CCC CTG CTC AAG 1005
```

|  |  |  | R | K | Q | R | T | S | R | A | L | M | H | I | T | D | W | Y | P | T | L | V | 355 |
|---|---|---|---|---|---|---|---|---|---|---|---|---|---|---|---|---|---|---|---|---|---|---|---|---|

```
    R   K   Q   R   T   S   R   A   L   M   H   I   T   D   W   Y   P   T   L   V   355
   CCA AAG CAA CGG ACA AGC CGG GCA CTG ATG CAC ATC ACT GAC TGG TAC CCG ACC CTG GTG  1065
    G   L   A   G   G   T   T   S   A   A   D   G   L   D   G   Y   D   V   W   P   375
   GGT CTG GCA GGT GGT ACC ACC TCA GCA GCC GAT GGG CTA GAT GGC TAC GAC GTG TGG CCG  1125
    A   I   S   E   G   R   A   S   P   R   T   E   I   L   H   N   I   D   P   L   395
   GCC ATC AGC GAG GGC CGG GCC TCA CCA CGC ACG GAG ATC CTG CAC AAC ATT GAC CCA CTC  1185
    Y   N   H   A   Q   H   G   S   L   E   G   G   F   G   I   W   N   T   A   V   415
   TAC AAC CAT GCC CAG CAT GGC TCC CTG GAG GGC GGC TTT GGC ATC TGG AAC ACC GCC GTG  1245
    Q   A   A   I   R   V   G   E   W   K   L   L   T   G   D   P   G   Y   G   D   435
   CAG GCT GCC ATC CGC GTG GGT GAG TGG AAG CTG CTG ACA GGA GAC CCC GGC TAT GGC GAT  1305
    W   I   P   P   Q   T   L   A   T   F   P   G   S   W   W   N   L   E   R   M   455
   TGG ATC CCA CCG CAG ACA CTG GCC ACC TTC CCG GGT AGC TGG TGG AAC CTG GAA CGA ATG  1365
    A   S   V   R   Q   A   V   W   L   F   N   I   S   A   D   P   Y   E   R   E   475
   GCC AGT GTC CGC CAG GCC GTG TGG CTC TTC AAC ATC AGT GCT GAC CCT TAT GAA CGG GAG  1425
    D   L   A   G   Q   R   P   D   V   V   R   T   L   L   A   R   L   A   E   Y   495
   GAC CTG GCT GGC CAG CGG CCT GAT GTG GTC CGC ACC CTG CTG GCT CGC CTG GCC GAA TAT  1485
    N   R   T   A   I   P   V   R   Y   P   A   E   N   P   R   A   H   P   D   F   515
   AAC CGC ACA GCC ATC CCG GTA CGC TAC CCA GCT GAG AAC CCC CGG GCT CAT CCT GAC TTT  1545
    N   G   G   A   W   G   P   W   A   S   D   E   E   E   E   E   E   G   R   535
   AAT GGG GGT GCT TGG GGG CCC TGG GCC AGT GAT GAG GAA GAG GAG GAA GAG GAA GGG AGG  1605
    A   R   S   F   S   R   G   R   R   K   K   K   C   K   I   C   K   L   R   S   555
   GCT CGA AGC TTC TCC CGG GGT CGT CGC AAG AAA AAA TGC AAG ATT TGC AAG CTT CGA TCC  1665
    F   F   R   K   L   N   T   R   L   M   S   Q   R   I   *                       570
   TTT TTC CGT AAA CTC AAC ACC AGG CTA ATG TCC CAA CGG ATC TGA                      1710
```

TGGTGGGGAGGGAGAAAACTGTCCTTTAGAGGATCTTCCCCACTCCGGCTTGGCCCTGCTGTTTCTCAGGGAGAAGCCT
GTCACATCTCCATCTACAGGGAGTTGGAGGGTGTAGAGTCCCTTGGTTGAACAGGGTAGGGAGCCTGGATAGGAGTGGG
TGGGAATAAACCAGACTGGGATGCCTGTGTCTCAGTCCTGCCTCCTCACGGACTTGCTCTGTGACCCTCAGGTGACCCAC
ATGAGCTTTTAGCCTCAGTTTCCTCATCTGTAAAATGAGCTCTAATGACTTTGTGACTCTTTGGTGTGGCCCTGGAGCC
TGGGGCCACGGTGGAGTTCCTGGCCGGCCTTGCCACTTGACAACTCCTTTAAGGCTTCCCCCTTAACACGGGATCCCTG
TGGTGGTGTTTGGGAGTTGCCTGGAGGCAACTCCAAGCCTGGCCCCCAGCTGAAGCATGGCAATCTGGCTGCTCTCTAC
AGGGACCCCCAAGCGCTGTGGGTGGAGGGCAGGGGTCGGGGGGGTTGACCTTCTTGGGTCTTCACATGGCCTAGGCCAG
TCCTCCGGTCAGACTGGTGTCAGGCACCGTGGTGCAAAATTCCTCTTCTGGCCCCTCCAGTACCCAGAGAAACTGGCTG
GGCCATTAACTGCTGCAGCACCAAGGGTGGTAGAAAGAGCTGTGAAGAGCCCCCAAACCAGTACCAGGACACCTGGGTT
CTCCTGTGACCTGGGGCACAGTTCTTGCCCTCTAGGCCTTGATTTCCCCACCTGCAAGTGGGGATGCCAGCCCTGGCTC
TGCCTCCTTCATGAGGCTCTGGAAGACTGGCCAAGGTTGTGGAGGAGCTTGTGAACTTGATTAAAGTGTCGTAACATGG
AAAAAAAAAAAAAAAAAAAAAAAGGGCGG

Prosite Pattern Matches for 25278

Prosite versions: Release 12.2 of February 1995

>PS00001/PDOC00001/ASN_GLYCOSYLATION N-glycosylation site.

Query: 276 NITW 279
Query: 288 NNSV 291
Query: 466 NISA 469
Query: 496 NRTA 499

>PS00004/PDOC00004/CAMP_PHOSPHO_SITE cAMP- and cGMP-dependent protein kinase phosphorylation site.

Query: 314 RKGT 317

>PS00005/PDOC00005/PKC_PHOSPHO_SITE Protein kinase C phosphorylation site.

Query: 102 TGR 104
Query: 160 TRR 162
Query: 244 SPR 246
Query: 340 TSR 342
Query: 383 SPR 385
Query: 457 SVR 459
Query: 566 SQR 568

>PS00006/PDOC00006/CK2_PHOSPHO_SITE Casein kinase II phosphorylation site.

Query: 67 SDIE 70
Query: 244 SPRE 247
Query: 268 TCMD 271
Query: 317 TYWE 320
Query: 363 SAAD 366
Query: 525 SDEE 528

>PS00007/PDOC00007/TYR_PHOSPHO_SITE Tyrosine kinase phosphorylation site.

Query: 134 KLQEAGY 140

>PS00008/PDOC00008/MYRISTYL N-myristoylation site.

Query: 110 GLQHSI 115
Query: 169 GSLTGN 174
Query: 205 GQYSTM 210
Query: 300 GQTFSG 305
Query: 321 GGVRGL 326
Query: 356 GLAGGT 361
Query: 402 GSLEGG 407
Query: 409 GIWNTA 414
Query: 447 GSWWNL 452

>PS00009/PDOC00009/AMIDATION Amidation site.

Query: 312 RGRK 315
Query: 541 RGRR 544

>PS00149/PDOC00117/SULFATASE_2 Sulfatases signature 2.

Query: 139 GYSTHMVGKW 148

>PS00523/PDOC00117/SULFATASE_1 Sulfatases signature 1.

Query: 91 PICTPSRSQLLTG 103

```
Input file 26212cons; Output File 26212pat
Sequence length 2266

CACGCGTCCGCCCACGCGTCCGTGGAGATATTAACTTTTTTCTTTTTTTTTTTCCTTGGTGGAAGCTGCTCTAGGGAGG

GGGGAGGAGGAGGAGAAAGTGAAATGTGCTGGAGAAGAGCGAGCCCTCCTTGTTCTTCCGGAGTCCCATCCATTAAGCC

ATCACTTCTGGAAGATTAAAGTTGTCGGACATGGTGACAGCTGAGAGGAGAGGAGGATTTCTTGCCAGGTGGAGAGTCT

TCACCGTCTGTTGGGTGCATGTGTGCGCCCGCASCGGCGCGGGGCGCGTGGTTCTCCGCGTGGAGTCTCACCTGGGACC
```

|      |   |   | M   | A   | P   | R   | G   | C   | A   | G   | H   | P   | P   | P   | P   | S   | P   | Q   | A   | C   | 18  |
|------|---|---|-----|-----|-----|-----|-----|-----|-----|-----|-----|-----|-----|-----|-----|-----|-----|-----|-----|-----|-----|
| TGAGTGA | | | ATG | GCT | CCC | AGG | GGC | TGT | GCG | GGG | CAT | CCG | CCT | CCG | CCT | TCT | CCA | CAG | GCC | TGT | 54 |

| V | C | P | G | K | M | L | A | M | G | A | L | A | G | F | W | I | L | C | L | 38 |
|---|---|---|---|---|---|---|---|---|---|---|---|---|---|---|---|---|---|---|---|----|
| GTC | TGT | CCT | GGA | AAG | ATG | CTA | GCA | ATG | GGG | GCG | CTG | GCA | GGA | TTC | TGG | ATC | CTC | TGC | CTC | 114 |

| L | T | Y | G | Y | L | S | W | G | Q | A | L | E | E | E | E | G | A | L | 58 |
|---|---|---|---|---|---|---|---|---|---|---|---|---|---|---|---|---|---|---|----|
| CTC | ACT | TAT | GGT | TAC | CTG | TCC | TGG | GGC | CAG | GCC | TTA | GAA | GAG | GAG | GAA | GAA | GGG | GCC | TTA | 174 |

| L | A | Q | A | G | E | K | L | E | P | S | T | T | S | T | S | Q | P | H | L | 78 |
|---|---|---|---|---|---|---|---|---|---|---|---|---|---|---|---|---|---|---|---|----|
| CTA | GCT | CAA | GCT | GGA | GAG | AAA | CTA | GAG | CCC | AGC | ACA | ACT | TCC | ACC | TCC | CAG | CCC | CAT | CTC | 234 |

| I | F | I | L | A | D | D | Q | G | F | R | D | V | G | Y | H | G | S | E | I | 98 |
|---|---|---|---|---|---|---|---|---|---|---|---|---|---|---|---|---|---|---|---|----|
| ATT | TTC | ATC | CTA | GCG | GAT | GAT | CAG | GGA | TTT | AGA | GAT | GTG | GGT | TAC | CAC | GGA | TCT | GAG | ATT | 294 |

| K | T | P | T | L | D | K | L | A | A | E | G | V | K | L | E | N | Y | Y | V | 118 |
|---|---|---|---|---|---|---|---|---|---|---|---|---|---|---|---|---|---|---|---|-----|
| AAA | ACA | CCT | ACT | CTT | GAC | AAG | CTC | GCT | GCC | GAA | GGA | GTT | AAA | CTG | GAG | AAC | TAC | TAT | GTC | 354 |

| Q | P | I | C | T | P | S | R | S | Q | F | I | T | G | K | Y | Q | I | H | T | 138 |
|---|---|---|---|---|---|---|---|---|---|---|---|---|---|---|---|---|---|---|---|-----|
| CAG | CCT | ATT | TGC | ACA | CCA | TCC | AGG | AGT | CAG | TTT | ATT | ACT | GGA | AAG | TAT | CAG | ATA | CAC | ACC | 414 |

| G | L | Q | H | S | I | I | R | P | T | Q | P | N | C | L | P | L | D | N | A | 158 |
|---|---|---|---|---|---|---|---|---|---|---|---|---|---|---|---|---|---|---|---|-----|
| GGA | CTT | CAA | CAT | TCT | ATC | ATA | AGA | CCT | ACC | CAA | CCC | AAC | TGT | TTA | CCT | CTG | GAC | AAT | GCC | 474 |

| T | L | P | Q | K | L | K | E | V | G | Y | S | T | H | M | V | G | K | W | H | 178 |
|---|---|---|---|---|---|---|---|---|---|---|---|---|---|---|---|---|---|---|---|-----|
| ACC | CTA | CCT | CAG | AAA | CTG | AAG | GAG | GTT | GGA | TAT | TCA | ACG | CAT | ATG | GTC | GGA | AAA | TGG | CAC | 534 |

| L | G | F | Y | R | K | E | C | M | P | T | R | R | G | F | D | T | F | F | G | 198 |
|---|---|---|---|---|---|---|---|---|---|---|---|---|---|---|---|---|---|---|---|-----|
| TTG | GGT | TTT | TAC | AGA | AAA | GAA | TGC | ATG | CCC | ACC | AGA | AGA | GGA | TTT | GAT | ACC | TTT | TTT | GGT | 594 |

| S | L | L | G | S | G | D | Y | Y | T | H | Y | K | C | D | S | P | G | M | C | 218 |
|---|---|---|---|---|---|---|---|---|---|---|---|---|---|---|---|---|---|---|---|-----|
| TCC | CTT | TTG | GGA | AGT | GGG | GAT | TAC | TAT | ACA | CAC | TAC | AAA | TGT | GAC | AGT | CCT | GGG | ATG | TGT | 654 |

| G | Y | D | L | Y | E | N | D | N | A | A | W | D | Y | D | N | G | I | Y | S | 238 |
|---|---|---|---|---|---|---|---|---|---|---|---|---|---|---|---|---|---|---|---|-----|
| GGC | TAT | GAC | TTG | TAT | GAA | AAC | GAC | AAT | GCT | GCC | TGG | GAC | TAT | GAC | AAT | GGC | ATA | TAC | TCC | 714 |

| T | Q | M | Y | T | Q | R | V | Q | Q | I | L | A | S | H | N | P | T | K | P | 258 |
|---|---|---|---|---|---|---|---|---|---|---|---|---|---|---|---|---|---|---|---|-----|
| ACA | CAG | ATG | TAC | ACT | CAG | AGA | GTA | CAG | CAA | ATC | TTA | GCT | TCC | CAT | AAC | CCC | ACA | AAG | CCT | 774 |

| I | F | L | Y | I | A | Y | Q | A | V | H | S | P | L | Q | A | P | G | R | Y | 278 |
|---|---|---|---|---|---|---|---|---|---|---|---|---|---|---|---|---|---|---|---|-----|
| ATA | TTT | TTA | TAT | ATT | GCC | TAT | CAA | GCT | GTT | CAT | TCA | CCA | CTG | CAA | GCT | CCT | GGC | AGG | TAT | 834 |

| F | E | H | Y | R | S | I | I | N | I | N | R | R | R | Y | A | A | M | L | S | 298 |
|---|---|---|---|---|---|---|---|---|---|---|---|---|---|---|---|---|---|---|---|-----|
| TTC | GAA | CAC | TAC | CGA | TCC | ATT | ATC | AAC | ATA | AAC | AGG | AGG | AGA | TAT | GCT | GCC | ATG | CTT | TCC | 894 |

| C | L | D | E | A | I | N | N | V | T | L | A | L | K | T | Y | G | F | Y | N | 318 |
|---|---|---|---|---|---|---|---|---|---|---|---|---|---|---|---|---|---|---|---|-----|
| TGC | TTA | GAT | GAA | GCA | ATC | AAC | AAC | GTG | ACA | TTG | GCT | CTA | AAG | ACT | TAT | GGT | TTC | TAT | AAC | 954 |

FIG. 15A.

```
N   S   I   I   I   Y   S   S   D   N   G   G   Q   P   T   A   G   G   S   N    338
AAC AGC ATT ATC ATT TAC TCT TCA GAT AAT GGT GGC CAG CCT ACG GCA GGA GGG AGT AAC 1014

W   P   L   R   G   S   K   G   T   Y   W   E   G   G   I   R   A   V   G   F    358
TGG CCT CTC AGA GGT AGC AAA GGA ACA TAT TGG GAA GGA GGG ATC CGG GCT GTA GGC TTT 1074

V   H   S   P   L   L   K   N   K   G   T   V   C   K   E   L   V   H   I   T    378
GTG CAT AGC CCA CTT CTG AAA AAC AAG GGA ACA GTG TGT AAG GAA CTT GTG CAC ATC ACT 1134

D   W   Y   P   T   L   I   S   L   A   E   G   Q   I   D   E   D   I   Q   L    398
GAC TGG TAC CCC ACT CTC ATT TCA CTG GCT GAA GGA CAG ATT GAT GAG GAC ATT CAA CTA 1194

D   G   Y   D   I   W   E   T   I   S   E   G   L   R   S   P   R   V   D   I    418
GAT GGC TAT GAT ATC TGG GAG ACC ATA AGT GAG GGT CTT CGC TCA CCC CGA GTA GAT ATT 1254

L   H   N   I   D   P   I   Y   T   K   A   K   N   G   S   W   A   A   G   Y    438
TTG CAT AAC ATT GAC CCC ATA TAC ACC AAG GCA AAA AAT GGC TCC TGG GCA GCA GGC TAT 1314

G   I   W   N   T   A   I   Q   S   A   I   R   V   Q   H   W   K   L   L   T    458
GGG ATC TGG AAC ACT GCA ATC CAG TCA GCC ATC AGA GTG CAG CAC TGG AAA TTG CTT ACA 1374

G   N   P   G   Y   S   D   W   V   P   P   Q   S   F   S   N   L   G   P   N    478
GGA AAT CCT GGC TAC AGC GAC TGG GTC CCC CCT CAG TCT TTC AGC AAC CTG GGA CCG AAC 1434

R   W   H   N   E   R   I   T   S   S   T   G   K   S   V   W   L   F   N   I    498
CGG TGG CAC AAT GAA CGG ATC ACC TCG TCA ACT GGC AAA AGT GTA TGG CTT TTC AAC ATC 1494

T   A   D   P   Y   E   R   V   D   L   S   N   R   Y   P   G   I   V   K   K    518
ACA GCC GAC CCA TAT GAG AGG GTG GAC CTA TCT AAC AGG TAT CCA GGA ATC GTG AAG AAG 1554

L   L   R   R   L   S   Q   F   N   K   T   A   V   P   V   R   Y   P   P   K    538
CTC CTA CGG AGG CTC TCA CAG TTC AAC AAA ACT GCA GTG CCG GTC AGG TAT CCC CCC AAA 1614

D   P   R   S   N   P   R   L   N   G   G   V   *                                 551
GAC CCC AGA AGT AAC CCT AGG CTC AAT GGA GGG GTC TAG                               1653

GGACCATGGTATAGAGAGGAAACCAAGAAAAAGAAGCCAAGCAAAAATCAGGCTGAGAAAAAGCAAAAGAAAAGCAAAA

AAAGAAGAAGAAACAGCAGAAAGCAGTCTCAGGTTCAACTTGCCATTCAGGTGTTACTTGTGGATAAGCACAAATATTT

CCTGTTTGGTTAAACTTTAATCAGTTCTTATCTTTCATCTGTTTCCTAGGTAAACCAGCAAATTTGGCTCGATAATATC

GCTGGCCTAAGCGTCAGGCTTGTTTTCATGCTGTGCCACCTGGTGCCGAATTC
```

FIG. 15B.

Prosite Pattern Matches for 26212prot

Prosite version: Release 12.2 of February 1995

>PS00001|PDOC00001|ASN_GLYCOSYLATION N-glycosylation site.

| Query: | 157 | NATL | 160 |
|---|---|---|---|
| Query: | 306 | NVTL | 309 |
| Query: | 318 | NNSI | 321 |
| Query: | 431 | NGSW | 434 |
| Query: | 497 | NITA | 500 |
| Query: | 527 | NKTA | 530 |

>PS00004|PDOC00004|CAMP_PHOSPHO_SITE cAMP- and cGMP-dependent protein kinase phosphorylation site.

| Query: | 521 | RRLS | 524 |
|---|---|---|---|

>PS00005|PDOC00005|PKC_PHOSPHO_SITE Protein kinase C phosphorylation site.

| Query: | 131 | TGK | 133 |
|---|---|---|---|
| Query: | 189 | TRR | 191 |
| Query: | 243 | TQR | 245 |
| Query: | 413 | SPR | 415 |
| Query: | 489 | TGK | 491 |
| Query: | 509 | SNR | 511 |

FIG. 18A.

>PS00006|PDOC00006|CK2_PHOSPHO_SITE Casein kinase II phosphorylation site.

Query: 298  SCLD  301

Query: 347  TYWE  350

Query: 386  SLAE  389

Query: 406  TISE  409

>PS00007|PDOC00007|TYR_PHOSPHO_SITE Tyrosine kinase phosphorylation site.

Query: 163  KLKEVGY  169

>PS00008|PDOC00008|MYRISTYL N-myristoylation site.

Query: 28   GALAGF  33

Query: 56   GALLAQ  61

Query: 139  GLQHSI  144

Query: 198  GSLLGS  203

Query: 235  GIYSTQ  240

Query: 329  GGQPTA  334

Query: 343  GSKGTY  348

Query: 351  GGIRAV  356

Query: 432  GSWAAG  437

Query: 439  GIWNTA  444

>PS00149|PDOC00117|SULFATASE_2 Sulfatases signature 2.

Query: 168  GYSTHMVGKW  177

>PS00523|PDOC00117|SULFATASE_1 Sulfatases signature 1.

Query: 120  PICTPSRSQFITG  132

FIG. 18B.

SEQUENCE LISTING

```
<160> NUMBER OF SEQ ID NOS: 8

<210> SEQ ID NO 1
<211> LENGTH: 525
<212> TYPE: PRT
<213> ORGANISM: homo sapiens

<400> SEQUENCE: 1

Met Gly Trp Leu Phe Leu Lys Val Leu Leu Ala Gly Val Ser Phe Ser
1               5                   10                  15

Gly Phe Leu Tyr Pro Leu Val Asp Phe Cys Ile Ser Gly Lys Thr Arg
            20                  25                  30

Gly Gln Lys Pro Asn Phe Val Ile Ile Leu Ala Asp Asp Met Gly Trp
        35                  40                  45

Gly Asp Leu Gly Ala Asn Trp Ala Glu Thr Lys Asp Thr Ala Asn Leu
    50                  55                  60

Asp Lys Met Ala Ser Glu Gly Met Arg Phe Val Asp Phe His Ala Ala
65                  70                  75                  80

Ala Ser Thr Cys Ser Pro Ser Arg Ala Ser Leu Leu Thr Gly Arg Leu
                85                  90                  95

Gly Leu Arg Asn Gly Val Thr Arg Asn Phe Ala Val Thr Ser Val Gly
            100                 105                 110

Gly Leu Pro Leu Asn Glu Thr Thr Leu Ala Glu Val Leu Gln Gln Ala
        115                 120                 125

Gly Tyr Val Thr Gly Ile Ile Gly Lys Trp His Leu Gly His His Gly
    130                 135                 140

Ser Tyr His Pro Asn Phe Arg Gly Phe Asp Tyr Tyr Phe Gly Ile Pro
145                 150                 155                 160

Tyr Ser His Asp Met Gly Cys Thr Asp Thr Pro Gly Tyr Asn His Pro
                165                 170                 175

Pro Cys Pro Ala Cys Pro Gln Gly Asp Gly Pro Ser Arg Asn Leu Gln
            180                 185                 190

Arg Asp Cys Tyr Thr Asp Val Ala Leu Pro Leu Tyr Glu Asn Leu Asn
        195                 200                 205

Ile Val Glu Gln Pro Val Asn Leu Ser Ser Leu Ala Gln Lys Tyr Ala
    210                 215                 220

Glu Lys Ala Thr Gln Phe Ile Gln Arg Ala Ser Thr Ser Gly Arg Pro
225                 230                 235                 240

Phe Leu Leu Tyr Val Ala Leu Ala His Met His Val Pro Leu Pro Val
                245                 250                 255
```

-continued

```
Thr Gln Leu Pro Ala Ala Pro Arg Gly Arg Ser Leu Tyr Gly Ala Gly
            260                 265                 270

Leu Trp Glu Met Asp Ser Leu Val Gly Gln Ile Lys Asp Lys Val Asp
        275                 280                 285

His Thr Val Lys Glu Asn Thr Phe Leu Trp Phe Thr Gly Asp Asn Gly
    290                 295                 300

Pro Trp Ala Gln Lys Cys Glu Leu Ala Gly Ser Val Gly Pro Phe Thr
305                 310                 315                 320

Gly Phe Trp Gln Thr Arg Gln Gly Ser Pro Ala Lys Gln Thr Thr
                325                 330                 335

Trp Glu Gly Gly His Arg Val Pro Ala Leu Ala Tyr Trp Pro Gly Arg
                340                 345                 350

Val Pro Val Asn Val Thr Ser Thr Ala Leu Leu Ser Val Leu Asp Ile
                355                 360                 365

Phe Pro Thr Val Val Ala Leu Ala Gln Ala Ser Leu Pro Gln Gly Arg
            370                 375                 380

Arg Phe Asp Gly Val Asp Val Ser Glu Val Leu Phe Gly Arg Ser Gln
385                 390                 395                 400

Pro Gly His Arg Val Leu Phe His Pro Asn Ser Gly Ala Ala Gly Glu
                405                 410                 415

Phe Gly Ala Leu Gln Thr Val Arg Leu Glu Arg Tyr Lys Ala Phe Tyr
            420                 425                 430

Ile Thr Gly Gly Ala Arg Ala Cys Asp Gly Ser Thr Gly Pro Glu Leu
        435                 440                 445

Gln His Lys Phe Pro Leu Ile Phe Asn Leu Glu Asp Asp Thr Ala Glu
    450                 455                 460

Ala Val Pro Leu Glu Arg Gly Gly Ala Glu Tyr Gln Ala Val Leu Pro
465                 470                 475                 480

Glu Val Arg Lys Val Leu Ala Asp Val Leu Gln Asp Ile Ala Asn Asp
                485                 490                 495

Asn Ile Ser Ser Ala Asp Tyr Thr Gln Asp Pro Ser Val Thr Pro Cys
            500                 505                 510

Cys Asn Pro Tyr Gln Ile Ala Cys Arg Cys Gln Ala Ala
            515                 520                 525
```

<210> SEQ ID NO 2
<211> LENGTH: 2175
<212> TYPE: DNA
<213> ORGANISM: homo sapiens
<220> FEATURE:
<221> NAME/KEY: CDS
<222> LOCATION: (248)...(1825)

<400> SEQUENCE: 2

```
cacgcgtccg caaatttcct gattctttg aattaggatt ccagatgggg gcctcatttc      60
tacagccccc aacattccta tagccgttat cactgccatc accactgcca ccagcatctt    120
cttgcagatt ccaccctgc tccccagaga cttcctgctt tgaaagtgag cagaaaggaa     180
gctctcagaa aaatctctag tggtggctgc cgtcgctcca gacaatcgga atcctgcctt    240 caccacc atg ggc tgg ctt ttt cta aag gtt ctg ttg gcg gga gtg agt      289
        Met Gly Trp Leu Phe Leu Lys Val Leu Leu Ala Gly Val Ser
        1               5                   10 ttc tca gga ttt ctt tat cct ctt gtg gat ttt tgc atc agt ggg aaa     337
Phe Ser Gly Phe Leu Tyr Pro Leu Val Asp Phe Cys Ile Ser Gly Lys
 15                  20                  25                  30 aca aga gga cag aag cca aac ttt gtg att att ttt gcc gat gac atg     385
```

-continued

```
        Thr Arg Gly Gln Lys Pro Asn Phe Val Ile Ile Leu Ala Asp Asp Met
                     35                  40                  45 gga tgg ggt gac ctg gga gca aac tgg gca gaa aca aag gac act gcc         433
Gly Trp Gly Asp Leu Gly Ala Asn Trp Ala Glu Thr Lys Asp Thr Ala
             50                  55                  60 aac ctt gat aag atg gct tcg gag gga atg agg ttt gtg gat ttc cat         481
Asn Leu Asp Lys Met Ala Ser Glu Gly Met Arg Phe Val Asp Phe His
         65                  70                  75 gca gct gcc tcc acc tgc tca ccc tcc cgg gct tcc ttg ctc acc ggc         529
Ala Ala Ala Ser Thr Cys Ser Pro Ser Arg Ala Ser Leu Leu Thr Gly
     80                  85                  90 cgg ctt ggc ctt cgc aat gga gtc aca cgc aac ttt gca gtc act tct         577
Arg Leu Gly Leu Arg Asn Gly Val Thr Arg Asn Phe Ala Val Thr Ser
 95                 100                 105                 110 gtg gga ggc ctt ccg ctc aac gag acc acc ttg gca gag gtg ctg cag         625
Val Gly Gly Leu Pro Leu Asn Glu Thr Thr Leu Ala Glu Val Leu Gln
                115                 120                 125 cag gcg ggt tac gtc act ggg ata ata ggc aaa tgg cat ctt gga cac         673
Gln Ala Gly Tyr Val Thr Gly Ile Ile Gly Lys Trp His Leu Gly His
            130                 135                 140 cac ggc tct tat cac ccc aac ttc cgt ggt ttt gat tac tac ttt gga         721
His Gly Ser Tyr His Pro Asn Phe Arg Gly Phe Asp Tyr Tyr Phe Gly
        145                 150                 155 atc cca tat agc cat gat atg ggc tgt act gat act cca ggc tac aac         769
Ile Pro Tyr Ser His Asp Met Gly Cys Thr Asp Thr Pro Gly Tyr Asn
    160                 165                 170 cac cct cct tgt cca gcg tgt cca cag ggt gat gga cca tca agg aac         817
His Pro Pro Cys Pro Ala Cys Pro Gln Gly Asp Gly Pro Ser Arg Asn
175                 180                 185                 190 ctt caa aga gac tgt tac act gac gtg gcc ctc cct ctt tat gaa aac         865
Leu Gln Arg Asp Cys Tyr Thr Asp Val Ala Leu Pro Leu Tyr Glu Asn
                195                 200                 205 ctc aac att gtg gag cag ccg gtg aac ttg agc agc ctt gcc cag aag         913
Leu Asn Ile Val Glu Gln Pro Val Asn Leu Ser Ser Leu Ala Gln Lys
            210                 215                 220 tat gct gag aaa gca acc cag ttc atc cag cgt gca agc acc agc ggg         961
Tyr Ala Glu Lys Ala Thr Gln Phe Ile Gln Arg Ala Ser Thr Ser Gly
        225                 230                 235 agg ccc ttc ctg ctc tat gtg gct ctg gcc cac atg cac gtg ccc tta        1009
Arg Pro Phe Leu Leu Tyr Val Ala Leu Ala His Met His Val Pro Leu
    240                 245                 250 ccc gtg act cag cta cca gca gcg cca cgg ggc aga agc ctg tat ggt        1057
Pro Val Thr Gln Leu Pro Ala Ala Pro Arg Gly Arg Ser Leu Tyr Gly
255                 260                 265                 270 gca ggg ctc tgg gag atg gac agt ctg gtg ggc cag atc aag gac aaa        1105
Ala Gly Leu Trp Glu Met Asp Ser Leu Val Gly Gln Ile Lys Asp Lys
                275                 280                 285 gtt gac cac aca gtg aag gaa aac aca ttc ctc tgg ttt aca gga gac        1153
Val Asp His Thr Val Lys Glu Asn Thr Phe Leu Trp Phe Thr Gly Asp
            290                 295                 300 aat ggc ccg tgg gct cag aag tgt gag cta gcg ggc agt gtg ggt ccc        1201
Asn Gly Pro Trp Ala Gln Lys Cys Glu Leu Ala Gly Ser Val Gly Pro
        305                 310                 315 ttc act gga ttt tgg caa act cgt caa ggg gga agt cca gcc aag cag        1249
Phe Thr Gly Phe Trp Gln Thr Arg Gln Gly Gly Ser Pro Ala Lys Gln
    320                 325                 330 acg acc tgg gaa gga ggg cac cgg gtc cca gca ctg gct tac tgg cct        1297
Thr Thr Trp Glu Gly Gly His Arg Val Pro Ala Leu Ala Tyr Trp Pro
335                 340                 345                 350
```

-continued

| | | |
|---|---|---|
| ggc aga gtt cca gtt aat gtc acc agc act gcc ttg tta agc gtg ctg<br>Gly Arg Val Pro Val Asn Val Thr Ser Thr Ala Leu Leu Ser Val Leu<br>355 360 365 | | 1345 |
| gac att ttt cca act gtg gta gcc ctg gcc cag gcc agc tta cct caa<br>Asp Ile Phe Pro Thr Val Val Ala Leu Ala Gln Ala Ser Leu Pro Gln<br>370 375 380 | | 1393 |
| gga cgg cgc ttt gat ggt gtg gac gtc tcc gag gtg ctc ttt ggc cgg<br>Gly Arg Arg Phe Asp Gly Val Asp Val Ser Glu Val Leu Phe Gly Arg<br>385 390 395 | | 1441 |
| tca cag cct ggg cac agg gtg ctg ttc cac ccc aac agc ggg gca gct<br>Ser Gln Pro Gly His Arg Val Leu Phe His Pro Asn Ser Gly Ala Ala<br>400 405 410 | | 1489 |
| gga gag ttt gga gcc ctg cag act gtc cgc ctg gag cgt tac aag gcc<br>Gly Glu Phe Gly Ala Leu Gln Thr Val Arg Leu Glu Arg Tyr Lys Ala<br>415 420 425 430 | | 1537 |
| ttc tac att acc ggt gga gcc agg gcg tgt gat ggg agc acg ggg cct<br>Phe Tyr Ile Thr Gly Gly Ala Arg Ala Cys Asp Gly Ser Thr Gly Pro<br>435 440 445 | | 1585 |
| gag ctg cag cat aag ttt cct ctg att ttc aac ctg gaa gac gat acc<br>Glu Leu Gln His Lys Phe Pro Leu Ile Phe Asn Leu Glu Asp Asp Thr<br>450 455 460 | | 1633 |
| gca gaa gct gtg ccc cta gaa aga ggt ggt gcg gag tac cag gct gtg<br>Ala Glu Ala Val Pro Leu Glu Arg Gly Gly Ala Glu Tyr Gln Ala Val<br>465 470 475 | | 1681 |
| ctg ccc gag gtc aga aag gtt ctt gca gac gtc ctc caa gac att gcc<br>Leu Pro Glu Val Arg Lys Val Leu Ala Asp Val Leu Gln Asp Ile Ala<br>480 485 490 | | 1729 |
| aac gac aac atc tcc agc gca gat tac act cag gac cct tca gta act<br>Asn Asp Asn Ile Ser Ser Ala Asp Tyr Thr Gln Asp Pro Ser Val Thr<br>495 500 505 510 | | 1777 |
| ccc tgc tgt aat ccc tac caa att gcc tgc cgc tgt caa gcc gca taa<br>Pro Cys Cys Asn Pro Tyr Gln Ile Ala Cys Arg Cys Gln Ala Ala *<br>515 520 525 | | 1825 |
| cagaccaatt tttattccac gaggaggagt acctggaaat taggcaagtt tgcttccaaa | | 1885 |
| tttcattttt accctcttta caaacacacg ctttagttta gtcttggagt ttagttttgg | | 1945 |
| agttagcctt gcatatccct tctgtatcct gtccctcctc cacgccgacc cgagagcagc | | 2005 |
| tgagctgcgc tggctctggg cagggagtgt gccttaatgg gaagcacacg ggctttggag | | 2065 |
| tcaggcacag gtgccagctc cagcttttga acttgggcaa ttgtttaacc taacctgcaa | | 2125 |
| gttgattttg agggttaaat aaaggcatac atgaaaaaaa aaaaaaaaa | | 2175 |

<210> SEQ ID NO 3
<211> LENGTH: 871
<212> TYPE: PRT
<213> ORGANISM: homo sapiens

<400> SEQUENCE: 3

Met Lys Tyr Ser Cys Cys Ala Leu Val Leu Ala Val Leu Gly Thr Glu
1               5                   10                  15

Leu Leu Gly Ser Leu Cys Ser Thr Val Arg Ser Pro Arg Phe Arg Gly
                20                  25                  30

Arg Ile Gln Gln Glu Arg Lys Asn Ile Arg Pro Asn Ile Ile Leu Val
        35                  40                  45

Leu Thr Asp Asp Gln Asp Val Glu Leu Gly Ser Leu Gln Val Met Asn
    50                  55                  60

Lys Thr Arg Lys Ile Met Glu His Gly Gly Ala Thr Phe Ile Asn Ala
65                  70                  75                  80

-continued

```
Phe Val Thr Thr Pro Met Cys Cys Pro Ser Arg Ser Ser Met Leu Thr
                 85                  90                  95

Gly Lys Tyr Val His Asn His Asn Val Tyr Thr Asn Asn Glu Asn Cys
                100                 105                 110

Ser Ser Pro Ser Trp Gln Ala Met His Glu Pro Arg Thr Phe Ala Val
                115                 120                 125

Tyr Leu Asn Asn Thr Gly Tyr Arg Thr Ala Phe Phe Gly Lys Tyr Leu
            130                 135                 140

Asn Glu Tyr Asn Gly Ser Tyr Ile Pro Pro Gly Trp Arg Glu Trp Leu
145                 150                 155                 160

Gly Leu Ile Lys Asn Ser Arg Phe Tyr Asn Tyr Thr Val Cys Arg Asn
                165                 170                 175

Gly Ile Lys Glu Lys His Gly Phe Asp Tyr Ala Lys Asp Tyr Phe Thr
                180                 185                 190

Asp Leu Ile Thr Asn Glu Ser Ile Asn Tyr Phe Lys Met Ser Lys Arg
            195                 200                 205

Met Tyr Pro His Arg Pro Val Met Met Val Ile Ser His Ala Ala Pro
        210                 215                 220

His Gly Pro Glu Asp Ser Ala Pro Gln Phe Ser Lys Leu Tyr Pro Asn
225                 230                 235                 240

Ala Ser Gln His Ile Thr Pro Ser Tyr Asn Tyr Ala Pro Asn Met Asp
                245                 250                 255

Lys His Trp Ile Met Gln Tyr Thr Gly Pro Met Leu Pro Ile His Met
                260                 265                 270

Glu Phe Thr Asn Ile Leu Gln Arg Lys Arg Leu Gln Thr Leu Met Ser
            275                 280                 285

Val Asp Asp Ser Val Glu Arg Leu Tyr Asn Met Leu Val Glu Thr Gly
        290                 295                 300

Glu Leu Glu Asn Thr Tyr Ile Ile Tyr Thr Ala Asp His Gly Tyr His
305                 310                 315                 320

Ile Gly Gln Phe Gly Leu Val Lys Gly Lys Ser Met Pro Tyr Asp Phe
                325                 330                 335

Asp Ile Arg Val Pro Phe Phe Ile Arg Gly Pro Ser Val Glu Pro Gly
                340                 345                 350

Ser Ile Val Pro Gln Ile Val Leu Asn Ile Asp Leu Ala Pro Thr Ile
            355                 360                 365

Leu Asp Ile Ala Gly Leu Asp Thr Pro Pro Asp Val Asp Gly Lys Ser
370                 375                 380

Val Leu Lys Leu Leu Asp Pro Glu Lys Pro Gly Asn Arg Phe Arg Thr
385                 390                 395                 400

Asn Lys Lys Ala Lys Ile Trp Arg Asp Thr Phe Leu Val Glu Arg Gly
                405                 410                 415

Lys Phe Leu Arg Lys Lys Glu Glu Ser Ser Lys Asn Ile Gln Gln Ser
            420                 425                 430

Asn His Leu Pro Lys Tyr Glu Arg Val Lys Glu Leu Cys Gln Gln Ala
        435                 440                 445

Arg Tyr Gln Thr Ala Cys Glu Gln Pro Gly Gln Lys Trp Gln Cys Ile
        450                 455                 460

Glu Asp Thr Ser Gly Lys Leu Arg Ile His Lys Cys Lys Gly Pro Ser
465                 470                 475                 480

Asp Leu Leu Thr Val Arg Gln Ser Thr Arg Asn Leu Tyr Ala Arg Gly
                485                 490                 495

Phe His Asp Lys Asp Lys Glu Cys Ser Cys Arg Glu Ser Gly Tyr Arg
```

```
                500             505             510
Ala Ser Arg Ser Gln Arg Lys Ser Gln Arg Gln Phe Leu Arg Asn Gln
        515                 520                 525

Gly Thr Pro Lys Tyr Lys Pro Arg Phe Val His Thr Arg Gln Thr Arg
        530                 535                 540

Ser Leu Ser Val Glu Phe Glu Gly Glu Ile Tyr Asp Ile Asn Leu Glu
545                 550                 555                 560

Glu Glu Glu Glu Leu Gln Val Leu Gln Pro Arg Asn Ile Ala Lys Arg
                565                 570                 575

His Asp Glu Gly His Lys Gly Pro Arg Asp Leu Gln Ala Ser Ser Gly
            580                 585                 590

Gly Asn Arg Gly Arg Met Leu Ala Asp Ser Ser Asn Ala Val Gly Pro
        595                 600                 605

Pro Thr Thr Val Arg Val Thr His Lys Cys Phe Ile Leu Pro Asn Asp
        610                 615                 620

Ser Ile His Cys Glu Arg Glu Leu Tyr Gln Ser Ala Arg Ala Trp Lys
625                 630                 635                 640

Asp His Lys Ala Tyr Ile Asp Lys Glu Ile Glu Ala Leu Gln Asp Lys
                645                 650                 655

Ile Lys Asn Leu Arg Glu Val Arg Gly His Leu Lys Arg Arg Lys Pro
                660                 665                 670

Glu Glu Cys Ser Cys Ser Lys Gln Ser Tyr Tyr Asn Lys Glu Lys Gly
            675                 680                 685

Val Lys Lys Gln Glu Lys Leu Lys Ser His Leu His Pro Phe Lys Glu
        690                 695                 700

Ala Ala Gln Glu Val Asp Ser Lys Leu Gln Leu Phe Lys Glu Asn Asn
705                 710                 715                 720

Arg Arg Arg Lys Lys Glu Arg Lys Glu Lys Arg Arg Gln Arg Lys Gly
                725                 730                 735

Glu Glu Cys Ser Leu Pro Gly Leu Thr Cys Phe Thr His Asp Asn Asn
            740                 745                 750

His Trp Gln Thr Ala Pro Phe Trp Asn Leu Gly Ser Phe Cys Ala Cys
        755                 760                 765

Thr Ser Ser Asn Asn Asn Thr Tyr Trp Cys Leu Arg Thr Val Asn Glu
770                 775                 780

Thr His Asn Phe Leu Phe Cys Glu Phe Ala Thr Gly Phe Leu Glu Tyr
785                 790                 795                 800

Phe Asp Met Asn Thr Asp Pro Tyr Gln Leu Thr Asn Thr Val His Thr
                805                 810                 815

Val Glu Arg Gly Ile Leu Asn Gln Leu His Val Gln Leu Met Glu Leu
            820                 825                 830

Arg Ser Cys Gln Gly Tyr Lys Gln Cys Asn Pro Arg Pro Lys Asn Leu
        835                 840                 845

Asp Val Gly Asn Lys Asp Gly Gly Ser Tyr Asp Leu His Arg Gly Gln
        850                 855                 860

Leu Trp Asp Gly Trp Glu Gly
865                 870

<210> SEQ ID NO 4
<211> LENGTH: 4321
<212> TYPE: DNA
<213> ORGANISM: homo sapiens
<220> FEATURE:
<221> NAME/KEY: CDS
<222> LOCATION: (510)...(3125)
```

```
<221> NAME/KEY: misc_feature
<222> LOCATION: 4310
<223> OTHER INFORMATION: n = A,T,C or G

<400> SEQUENCE: 4
cccacgcgtc cggctaatga atcttggggc cggtgtcggg ccggggcggc ttgatcggca      60
actaggaaac cccaggcgca gaggccagga gcgagggcag cgaggatcag aggccaggcc     120
ttcccggctg ccggcgctcc tcggaggtca gggcagatga ggaacatgac tctcccccctt   180 cggaggagga aggaagtccc gctgccacct tatctctgct cctctgcctc ctccctgttc     240
ccagagcttt ttctctagag aagatttga aggcggcttt tgtgctgacg gccacccacc     300
atcatctaaa gaagataaac ttggcaaatg acatgcaggt tcttcaaggc agaataattg     360
cagaaaatct tcaaaggacc ctatctgcag atgttctgaa tacctctgag aatagagatt     420
gattattcaa ccaggatacc taattcaaga actccagaaa tcaggagacg gagacatttt     480
gtcagttttg caacattgga ccaaataca atg aag tat tct tgc tgt gct ctg      533
                                 Met Lys Tyr Ser Cys Cys Ala Leu
                                  1               5
```

```
gtt ttg gct gtc ctg ggc aca gaa ttg ctg gga agc ctc tgt tcg act      581
Val Leu Ala Val Leu Gly Thr Glu Leu Leu Gly Ser Leu Cys Ser Thr
 10              15                  20 gtc aga tcc ccg agg ttc aga gga cgg ata cag cag gaa cga aaa aac      629
Val Arg Ser Pro Arg Phe Arg Gly Arg Ile Gln Gln Glu Arg Lys Asn
 25              30                  35                  40 atc cga ccc aac att att ctt gtg ctt acc gat gat caa gat gtg gag      677
Ile Arg Pro Asn Ile Ile Leu Val Leu Thr Asp Asp Gln Asp Val Glu
                 45                  50                  55 ctg ggg tcc ctg caa gtc atg aac aaa acg aga aag att atg gaa cat      725
Leu Gly Ser Leu Gln Val Met Asn Lys Thr Arg Lys Ile Met Glu His
             60                  65                  70 ggg ggg gcc acc ttc atc aat gcc ttt gtg act aca ccc atg tgc tgc      773
Gly Gly Ala Thr Phe Ile Asn Ala Phe Val Thr Thr Pro Met Cys Cys
         75                  80                  85 ccg tca cgg tcc tcc atg ctc acc ggg aag tat gtg cac aat cac aat      821
Pro Ser Arg Ser Ser Met Leu Thr Gly Lys Tyr Val His Asn His Asn
     90                  95                 100 gtc tac acc aac aac gag aac tgc tct tcc ccc tcg tgg cag gcc atg      869
Val Tyr Thr Asn Asn Glu Asn Cys Ser Ser Pro Ser Trp Gln Ala Met
105                 110                 115                 120 cat gag cct cgg act ttt gct gta tat ctt aac aac act ggc tac aga      917
His Glu Pro Arg Thr Phe Ala Val Tyr Leu Asn Asn Thr Gly Tyr Arg
                125                 130                 135 aca gcc ttt ttt gga aaa tac ctc aat gaa tat aat ggc agc tac atc      965
Thr Ala Phe Phe Gly Lys Tyr Leu Asn Glu Tyr Asn Gly Ser Tyr Ile
            140                 145                 150 ccc cct ggg tgg cga gaa tgg ctt gga tta atc aag aat tct cgc ttc     1013
Pro Pro Gly Trp Arg Glu Trp Leu Gly Leu Ile Lys Asn Ser Arg Phe
        155                 160                 165 tat aat tac act gtt tgt cgc aat ggc atc aaa gaa aag cat gga ttt     1061
Tyr Asn Tyr Thr Val Cys Arg Asn Gly Ile Lys Glu Lys His Gly Phe
    170                 175                 180 gat tat gca aag gac tac ttc aca gac tta atc act aac gag agc att     1109
Asp Tyr Ala Lys Asp Tyr Phe Thr Asp Leu Ile Thr Asn Glu Ser Ile
185                 190                 195                 200 aat tac ttc aaa atg tct aag aga atg tat ccc cat agg ccc gtt atg     1157
Asn Tyr Phe Lys Met Ser Lys Arg Met Tyr Pro His Arg Pro Val Met
                205                 210                 215 atg gtg atc agc cac gct gcg ccc cac ggc ccc gag gac tca gcc cca     1205
```

-continued

```
            Met Val Ile Ser His Ala Ala Pro His Gly Pro Glu Asp Ser Ala Pro
                    220                 225                 230 cag ttt tct aaa ctg tac ccc aat gct tcc caa cac ata act cct agt         1253
Gln Phe Ser Lys Leu Tyr Pro Asn Ala Ser Gln His Ile Thr Pro Ser
            235                 240                 245 tat aac tat gca cca aat atg gat aaa cac tgg att atg cag tac aca         1301
Tyr Asn Tyr Ala Pro Asn Met Asp Lys His Trp Ile Met Gln Tyr Thr
        250                 255                 260 gga cca atg ctg ccc atc cac atg gaa ttt aca aac att cta cag cgc         1349
Gly Pro Met Leu Pro Ile His Met Glu Phe Thr Asn Ile Leu Gln Arg
265                 270                 275                 280 aaa agg ctc cag act ttg atg tca gtg gat gat tct gtg gag agg ctg         1397
Lys Arg Leu Gln Thr Leu Met Ser Val Asp Asp Ser Val Glu Arg Leu
                285                 290                 295 tat aac atg ctc gtg gag acg ggg gag ctg gag aat act tac atc att         1445
Tyr Asn Met Leu Val Glu Thr Gly Glu Leu Glu Asn Thr Tyr Ile Ile
            300                 305                 310 tac acc gcc gac cat ggt tac cat att ggg cag ttt gga ctg gtc aag         1493
Tyr Thr Ala Asp His Gly Tyr His Ile Gly Gln Phe Gly Leu Val Lys
        315                 320                 325 ggg aaa tcc atg cca tat gac ttt gat att cgt gtg cct ttt ttt att         1541
Gly Lys Ser Met Pro Tyr Asp Phe Asp Ile Arg Val Pro Phe Phe Ile
330                 335                 340 cgt ggt cca agt gta gaa cca gga tca ata gtc cca cag atc gtt ctc         1589
Arg Gly Pro Ser Val Glu Pro Gly Ser Ile Val Pro Gln Ile Val Leu
345                 350                 355                 360 aac att gac ttg gcc ccc acg atc ctg gat att gct ggg ctc gac aca         1637
Asn Ile Asp Leu Ala Pro Thr Ile Leu Asp Ile Ala Gly Leu Asp Thr
                365                 370                 375 cct cct gat gtg gac ggc aag tct gtc ctc aaa ctt ctg gac cca gaa         1685
Pro Pro Asp Val Asp Gly Lys Ser Val Leu Lys Leu Leu Asp Pro Glu
            380                 385                 390 aag cca ggt aac agg ttt cga aca aac aag aag gcc aaa att tgg cgt         1733
Lys Pro Gly Asn Arg Phe Arg Thr Asn Lys Lys Ala Lys Ile Trp Arg
        395                 400                 405 gat aca ttc cta gtg gaa aga ggc aaa ttt cta cgt aag aag gaa gaa         1781
Asp Thr Phe Leu Val Glu Arg Gly Lys Phe Leu Arg Lys Lys Glu Glu
410                 415                 420 tcc agc aag aat atc caa cag tca aat cac ttg ccc aaa tat gaa cgg         1829
Ser Ser Lys Asn Ile Gln Gln Ser Asn His Leu Pro Lys Tyr Glu Arg
425                 430                 435                 440 gtc aaa gaa cta tgc cag cag gcc agg tac cag aca gcc tgt gaa caa         1877
Val Lys Glu Leu Cys Gln Gln Ala Arg Tyr Gln Thr Ala Cys Glu Gln
                445                 450                 455 ccg ggg cag aag tgg caa tgc att gag gat aca tct ggc aag ctt cga         1925
Pro Gly Gln Lys Trp Gln Cys Ile Glu Asp Thr Ser Gly Lys Leu Arg
            460                 465                 470 att cac aag tgt aaa gga ccc agt gac ctg ctc aca gtc cgg cag agc         1973
Ile His Lys Cys Lys Gly Pro Ser Asp Leu Leu Thr Val Arg Gln Ser
        475                 480                 485 acg cgg aac ctc tac gct cgc ggc ttc cat gac aaa gac aaa gag tgc         2021
Thr Arg Asn Leu Tyr Ala Arg Gly Phe His Asp Lys Asp Lys Glu Cys
490                 495                 500 agt tgt agg gag tct ggt tac cgt gcc agc aga agc caa aga aag agt         2069
Ser Cys Arg Glu Ser Gly Tyr Arg Ala Ser Arg Ser Gln Arg Lys Ser
505                 510                 515                 520 caa cgg caa ttc ttg aga aac cag ggg act cca aag tac aag ccc aga         2117
Gln Arg Gln Phe Leu Arg Asn Gln Gly Thr Pro Lys Tyr Lys Pro Arg
                525                 530                 535
```

-continued

| | | |
|---|---|---|
| ttt gtc cat act cgg cag aca cgt tcc ttg tcc gtc gaa ttt gaa ggt<br>Phe Val His Thr Arg Gln Thr Arg Ser Leu Ser Val Glu Phe Glu Gly<br>540 545 550 | 2165 | |
| gaa ata tat gac ata aat ctg gaa gaa gaa gaa gaa ttg caa gtg ttg<br>Glu Ile Tyr Asp Ile Asn Leu Glu Glu Glu Glu Glu Leu Gln Val Leu<br>555 560 565 | 2213 | |
| caa cca aga aac att gct aag cgt cat gat gaa ggc cac aag ggg cca<br>Gln Pro Arg Asn Ile Ala Lys Arg His Asp Glu Gly His Lys Gly Pro<br>570 575 580 | 2261 | |
| aga gat ctc cag gct tcc agt ggt ggc aac agg ggc agg atg ctg gca<br>Arg Asp Leu Gln Ala Ser Ser Gly Gly Asn Arg Gly Arg Met Leu Ala<br>585 590 595 600 | 2309 | |
| gat agc agc aac gcc gtg ggc cca cct acc act gtc cga gtg aca cac<br>Asp Ser Ser Asn Ala Val Gly Pro Pro Thr Thr Val Arg Val Thr His<br>605 610 615 | 2357 | |
| aag tgt ttt att ctt ccc aat gac tct atc cat tgt gag aga gaa ctg<br>Lys Cys Phe Ile Leu Pro Asn Asp Ser Ile His Cys Glu Arg Glu Leu<br>620 625 630 | 2405 | |
| tac caa tcg gcc aga gcg tgg aag gac cat aag gca tac att gac aaa<br>Tyr Gln Ser Ala Arg Ala Trp Lys Asp His Lys Ala Tyr Ile Asp Lys<br>635 640 645 | 2453 | |
| gag att gaa gct ctg caa gat aaa att aag aat tta aga gaa gtg aga<br>Glu Ile Glu Ala Leu Gln Asp Lys Ile Lys Asn Leu Arg Glu Val Arg<br>650 655 660 | 2501 | |
| gga cat ctg aag aga agg aag cct gag gaa tgt agc tgc agt aaa caa<br>Gly His Leu Lys Arg Arg Lys Pro Glu Glu Cys Ser Cys Ser Lys Gln<br>665 670 675 680 | 2549 | |
| agc tat tac aat aaa gag aaa ggt gta aaa aag caa gag aaa tta aag<br>Ser Tyr Tyr Asn Lys Glu Lys Gly Val Lys Lys Gln Glu Lys Leu Lys<br>685 690 695 | 2597 | |
| agc cat ctt cac cca ttc aag gag gct gct cag gaa gta gat agc aaa<br>Ser His Leu His Pro Phe Lys Glu Ala Ala Gln Glu Val Asp Ser Lys<br>700 705 710 | 2645 | |
| ctg caa ctt ttc aag gag aac aac cgt agg agg aag aag gag agg aag<br>Leu Gln Leu Phe Lys Glu Asn Asn Arg Arg Arg Lys Lys Glu Arg Lys<br>715 720 725 | 2693 | |
| gag aag aga cgg cag agg aag ggg gaa gag tgc agc ctg cct ggc ctc<br>Glu Lys Arg Arg Gln Arg Lys Gly Glu Glu Cys Ser Leu Pro Gly Leu<br>730 735 740 | 2741 | |
| act tgc ttc acg cat gac aac aac cac tgg cag aca gcc ccg ttc tgg<br>Thr Cys Phe Thr His Asp Asn Asn His Trp Gln Thr Ala Pro Phe Trp<br>745 750 755 760 | 2789 | |
| aac ctg gga tct ttc tgt gct tgc acg agt tct aac aat aac acc tac<br>Asn Leu Gly Ser Phe Cys Ala Cys Thr Ser Ser Asn Asn Asn Thr Tyr<br>765 770 775 | 2837 | |
| tgg tgt ttg cgt aca gtt aat gag acg cat aat ttt ctt ttc tgt gag<br>Trp Cys Leu Arg Thr Val Asn Glu Thr His Asn Phe Leu Phe Cys Glu<br>780 785 790 | 2885 | |
| ttt gct act ggc ttt ttg gag tat ttt gat atg aat aca gat cct tat<br>Phe Ala Thr Gly Phe Leu Glu Tyr Phe Asp Met Asn Thr Asp Pro Tyr<br>795 800 805 | 2933 | |
| cag ctc aca aat aca gtg cac acg gta gaa cga ggc att ttg aat cag<br>Gln Leu Thr Asn Thr Val His Thr Val Glu Arg Gly Ile Leu Asn Gln<br>810 815 820 | 2981 | |
| cta cac gta caa cta atg gag ctc aga agc tgt caa gga tat aag cag<br>Leu His Val Gln Leu Met Glu Leu Arg Ser Cys Gln Gly Tyr Lys Gln<br>825 830 835 840 | 3029 | |
| tgc aac cca aga cct aag aat ctt gat gtt gga aat aaa gat gga gga<br>Cys Asn Pro Arg Pro Lys Asn Leu Asp Val Gly Asn Lys Asp Gly Gly<br>845 850 855 | 3077 | |

-continued

```
agc tat gac cta cac aga gga cag tta tgg gat gga tgg gaa ggt taa    3125
Ser Tyr Asp Leu His Arg Gly Gln Leu Trp Asp Gly Trp Glu Gly  *
        860                 865                 870 tcagccccgt ctcactgcag acatcaactg gcaaggccta gaggagctac acagtgtgaa    3185
tgaaaacatc tatgagtaca gacaaaacta cagacttagt ctggtggact ggactaatta    3245
cttgaaggat ttagatagag tatttgcact gctgaagagt cactatgagc aaataaaaac    3305
aaataagact caaactgctc aaagtgacgg gttcttggtt gtctctgctg agcacgctgt    3365
gtcaatggag atggcctctg ctgactcaga tgaagaccca aggcataagg ttgggaaaac    3425
acctcatttg accttgccag ctgaccttca aaccctgcat ttgaaccgac caacattaag    3485
tccagagagt aaacttgaat ggaataacga cattccagaa gttaatcatt tgaattctga    3545
acactggaga aaaccgaaa atggacggg gcatgaagag actaatcatc tggaaaccga    3605
tttcagtggc gatggcatga cagagctaga gctcgggccc agccccaggc tgcagcccat    3665
tcgcaggcac ccgaaagaac ttccccagta tggtggtcct ggaaaggaca ttttgaaga    3725 tcaactatat cttcctgtgc attccgatgg aatttcagtt catcagatgt tcaccatggc    3785
caccgcagaa caccgaagta attccagcat agcggggaag atgttgacca aggtggagaa    3845
gaatcacgaa aaggagaagt cacagcacct agaaggcagc gcctcctctt cactctcctc    3905
tgattagatg aaactgttac cttaccctaa acacagtatt tcttttaac tttttattt    3965 gtaaactaat aaaggkaatc acagccacca acattccaag ctaccctggg tacctttgtg    4025
cagtagaagc tagtgagcat gtgagcaagc ggtgtgcaca cggagactca tcgttataat    4085
ttactatctg ccaaggagta gaaagaaagg ctggggatat ttgggttggc tttggktttg    4145
attttttgct tggttggttg gtttgkacta aaacagtatt atcttttgaa tatcgtaggg    4205
acataarkww wwwmmmwkktw wtcmawymra kakgsywrra wkgggstyty tskkrkstmw    4265
amwykwscmc cyskkrwwaw tywywmmywc mykytsssstg rykrnktaat gaagtt        4321
```

<210> SEQ ID NO 5
<211> LENGTH: 569
<212> TYPE: PRT
<213> ORGANISM: homo sapiens

<400> SEQUENCE: 5

```
Met His Thr Leu Thr Gly Phe Ser Leu Val Ser Leu Ser Phe Gly
 1               5                  10                  15

Tyr Leu Ser Trp Asp Trp Ala Lys Pro Ser Phe Val Ala Asp Gly Pro
                20                  25                  30

Gly Glu Ala Gly Glu Gln Pro Ser Ala Ala Pro Pro Gln Pro Pro His
            35                  40                  45

Ile Ile Phe Ile Leu Thr Asp Asp Gln Gly Tyr His Asp Val Gly Tyr
        50                  55                  60

His Gly Ser Asp Ile Glu Thr Pro Thr Leu Asp Arg Leu Ala Ala Lys
65                  70                  75                  80

Gly Val Lys Leu Glu Asn Tyr Tyr Ile Gln Pro Ile Cys Thr Pro Ser
                85                  90                  95

Arg Ser Gln Leu Leu Thr Gly Arg Tyr Gln Ile His Thr Gly Leu Gln
            100                 105                 110

His Ser Ile Ile Arg Pro Gln Gln Pro Asn Cys Leu Pro Leu Asp Gln
        115                 120                 125

Val Thr Leu Pro Gln Lys Leu Gln Glu Ala Gly Tyr Ser Thr His Met
    130                 135                 140
```

```
Val Gly Lys Trp His Leu Gly Phe Tyr Arg Lys Glu Cys Leu Pro Thr
145                 150                 155                 160

Arg Arg Gly Phe Asp Thr Phe Leu Gly Ser Leu Thr Gly Asn Val Asp
                165                 170                 175

Tyr Tyr Thr Tyr Asp Asn Cys Asp Gly Pro Gly Val Cys Gly Phe Asp
                180                 185                 190

Leu His Glu Gly Glu Asn Val Ala Trp Gly Leu Ser Gly Gln Tyr Ser
            195                 200                 205

Thr Met Leu Tyr Ala Gln Arg Ala Ser His Ile Leu Ala Ser His Ser
        210                 215                 220

Pro Gln Arg Pro Leu Phe Leu Tyr Val Ala Phe Gln Ala Val His Thr
225                 230                 235                 240

Pro Leu Gln Ser Pro Arg Glu Tyr Leu Tyr Arg Tyr Arg Thr Met Gly
                245                 250                 255

Asn Val Ala Arg Arg Lys Tyr Ala Ala Met Val Thr Cys Met Asp Glu
                260                 265                 270

Ala Val Arg Asn Ile Thr Trp Ala Leu Lys Arg Tyr Gly Phe Tyr Asn
            275                 280                 285

Asn Ser Val Ile Ile Phe Ser Ser Asp Asn Gly Gly Gln Thr Phe Ser
        290                 295                 300

Gly Gly Ser Asn Trp Pro Leu Arg Gly Arg Lys Gly Thr Tyr Trp Glu
305                 310                 315                 320

Gly Gly Val Arg Gly Leu Gly Phe Val His Ser Pro Leu Leu Lys Arg
                325                 330                 335

Lys Gln Arg Thr Ser Arg Ala Leu Met His Ile Thr Asp Trp Tyr Pro
                340                 345                 350

Thr Leu Val Gly Leu Ala Gly Gly Thr Thr Ser Ala Ala Asp Gly Leu
            355                 360                 365

Asp Gly Tyr Asp Val Trp Pro Ala Ile Ser Glu Gly Arg Ala Ser Pro
        370                 375                 380

Arg Thr Glu Ile Leu His Asn Ile Asp Pro Leu Tyr Asn His Ala Gln
385                 390                 395                 400

His Gly Ser Leu Glu Gly Gly Phe Gly Ile Trp Asn Thr Ala Val Gln
                405                 410                 415

Ala Ala Ile Arg Val Gly Glu Trp Lys Leu Leu Thr Gly Asp Pro Gly
                420                 425                 430

Tyr Gly Asp Trp Ile Pro Pro Gln Thr Leu Ala Thr Phe Pro Gly Ser
            435                 440                 445

Trp Trp Asn Leu Glu Arg Met Ala Ser Val Arg Gln Ala Val Trp Leu
        450                 455                 460

Phe Asn Ile Ser Ala Asp Pro Tyr Glu Arg Glu Asp Leu Ala Gly Gln
465                 470                 475                 480

Arg Pro Asp Val Val Arg Thr Leu Leu Ala Arg Leu Ala Glu Tyr Asn
                485                 490                 495

Arg Thr Ala Ile Pro Val Arg Tyr Pro Ala Glu Asn Pro Arg Ala His
                500                 505                 510

Pro Asp Phe Asn Gly Gly Ala Trp Gly Pro Trp Ala Ser Asp Glu Glu
            515                 520                 525

Glu Glu Glu Glu Glu Gly Arg Ala Arg Ser Phe Ser Arg Gly Arg Arg
        530                 535                 540

Lys Lys Lys Cys Lys Ile Cys Lys Leu Arg Ser Phe Phe Arg Lys Leu
545                 550                 555                 560
```

-continued

```
Asn Thr Arg Leu Met Ser Gln Arg Ile
                565
```

<210> SEQ ID NO 6
<211> LENGTH: 2940
<212> TYPE: DNA
<213> ORGANISM: homo sapiens
<220> FEATURE:
<221> NAME/KEY: CDS
<222> LOCATION: (334)...(2043)

<400> SEQUENCE: 6

```
ccacgcgtcc gcccacgcgt ccggctgcca cgccgcgtct caggctggcc gggctgagcc      60
ggggaagagg gagcaaaggc ggcgcagggc ctgcgcttag gcagcgggag gcagctcggc     120
gcgggcctga cctccccaga gcgccccgct gcggccgagc agatccggcc cagccgtccg     180
gcagccagtc ccggaccaga cactggaccg tccccggggg gcgctgaact ccctcgcagc     240
atccgagccg gcgggccggt ggtgcgccct gggcgcgcga ggtggtgagg ccccaggagc     300
ccggcgcgcc gggacacgcg gccggcttg gcg atg cac acc ctc act ggc ttc      354
                                   Met His Thr Leu Thr Gly Phe
                                    1               5 tct ctg gtc agc ctg ctc agc ttc ggc tac ctg tcc tgg gac tgg gcc      402
Ser Leu Val Ser Leu Leu Ser Phe Gly Tyr Leu Ser Trp Asp Trp Ala
        10                  15                  20 aag ccg agc ttc gtg gcc gac ggg ccc ggg gag gct ggc gag cag ccc      450
Lys Pro Ser Phe Val Ala Asp Gly Pro Gly Glu Ala Gly Glu Gln Pro
    25                  30                  35 tcg gcc gct ccg ccc cag cct ccc cac atc atc ttc atc ctc acg gac      498
Ser Ala Ala Pro Pro Gln Pro Pro His Ile Ile Phe Ile Leu Thr Asp
40                  45                  50                  55 gac caa ggc tac cac gac gtg ggc tac cat ggt tca gat atc gag acc      546
Asp Gln Gly Tyr His Asp Val Gly Tyr His Gly Ser Asp Ile Glu Thr
                60                  65                  70 cct acg ctg gac agg ctg gcg gcc aag ggg gtc aag ttg gag aat tat      594
Pro Thr Leu Asp Arg Leu Ala Ala Lys Gly Val Lys Leu Glu Asn Tyr
            75                  80                  85 tac atc cag ccc atc tgc acg cct tcg cgg agc cag ctc ctc act ggc      642
Tyr Ile Gln Pro Ile Cys Thr Pro Ser Arg Ser Gln Leu Leu Thr Gly
        90                  95                 100 agg tac cag atc cac aca gga ctc cag cat tcc atc atc cgc cca cag      690
Arg Tyr Gln Ile His Thr Gly Leu Gln His Ser Ile Ile Arg Pro Gln
    105                 110                 115 cag ccc aac tgc ctg ccc ctg gac cag gtg aca ctg cca cag aag ctg      738
Gln Pro Asn Cys Leu Pro Leu Asp Gln Val Thr Leu Pro Gln Lys Leu
120                 125                 130                 135 cag gag gca ggt tat tcc acc cat atg gtg ggc aag tgg cac ctg ggc      786
Gln Glu Ala Gly Tyr Ser Thr His Met Val Gly Lys Trp His Leu Gly
                140                 145                 150 ttc tac cgg aag gag tgt ctg ccc acc cgt cgg ggc ttc gac acc ttc      834
Phe Tyr Arg Lys Glu Cys Leu Pro Thr Arg Arg Gly Phe Asp Thr Phe
            155                 160                 165 ctg ggc tcg ctc acg ggc aat gtg gac tat tac acc tat gac aac tgt      882
Leu Gly Ser Leu Thr Gly Asn Val Asp Tyr Tyr Thr Tyr Asp Asn Cys
        170                 175                 180 gat ggc cca ggc gtg tgc ggc ttc gac ctg cac gag ggt gag aat gtg      930
Asp Gly Pro Gly Val Cys Gly Phe Asp Leu His Glu Gly Glu Asn Val
    185                 190                 195 gcc tgg ggg ctc agc ggc cag tac tcc act atg ctt tac gcc cag cgc      978
Ala Trp Gly Leu Ser Gly Gln Tyr Ser Thr Met Leu Tyr Ala Gln Arg
200                 205                 210                 215
```

-continued

| | |
|---|---|
| gcc agc cat atc ctg gcc agc cac agc cct cag cgt ccc ctc ttc ctc<br>Ala Ser His Ile Leu Ala Ser His Ser Pro Gln Arg Pro Leu Phe Leu<br>220 225 230 | 1026 |
| tat gtg gcc ttc cag gca gta cac aca ccc ctg cag tcc cct cgt gag<br>Tyr Val Ala Phe Gln Ala Val His Thr Pro Leu Gln Ser Pro Arg Glu<br>235 240 245 | 1074 |
| tac ctg tac cgc tac cgc acc atg ggc aat gtg gcc cgg cgg aag tac<br>Tyr Leu Tyr Arg Tyr Arg Thr Met Gly Asn Val Ala Arg Arg Lys Tyr<br>250 255 260 | 1122 |
| gcg gcc atg gtg acc tgc atg gat gag gct gtg cgc aac atc acc tgg<br>Ala Ala Met Val Thr Cys Met Asp Glu Ala Val Arg Asn Ile Thr Trp<br>265 270 275 | 1170 |
| gcc ctc aag cgc tac ggt ttc tac aac aac agt gtc atc atc ttc tcc<br>Ala Leu Lys Arg Tyr Gly Phe Tyr Asn Asn Ser Val Ile Ile Phe Ser<br>280 285 290 295 | 1218 |
| agt gac aat ggt ggc cag act ttc tcg ggg ggc agc aac tgg ccg ctc<br>Ser Asp Asn Gly Gly Gln Thr Phe Ser Gly Gly Ser Asn Trp Pro Leu<br>300 305 310 | 1266 |
| cga gga cgc aag ggc act tat tgg gaa ggt ggc gtg cgg gga cta ggc<br>Arg Gly Arg Lys Gly Thr Tyr Trp Glu Gly Gly Val Arg Gly Leu Gly<br>315 320 325 | 1314 |
| ttt gtc cac agt ccc ctg ctc aag cga aag caa cgg aca agc cgg gca<br>Phe Val His Ser Pro Leu Leu Lys Arg Lys Gln Arg Thr Ser Arg Ala<br>330 335 340 | 1362 |
| ctg atg cac atc act gac tgg tac ccg acc ctg gtg ggt ctg gca ggt<br>Leu Met His Ile Thr Asp Trp Tyr Pro Thr Leu Val Gly Leu Ala Gly<br>345 350 355 | 1410 |
| ggt acc acc tca gca gcc gat ggg cta gat ggc tac gac gtg tgg ccg<br>Gly Thr Thr Ser Ala Ala Asp Gly Leu Asp Gly Tyr Asp Val Trp Pro<br>360 365 370 375 | 1458 |
| gcc atc agc gag ggc cgg gcc tca cca cgc acg gag atc ctg cac aac<br>Ala Ile Ser Glu Gly Arg Ala Ser Pro Arg Thr Glu Ile Leu His Asn<br>380 385 390 | 1506 |
| att gac cca ctc tac aac cat gcc cag cat ggc tcc ctg gag ggc ggc<br>Ile Asp Pro Leu Tyr Asn His Ala Gln His Gly Ser Leu Glu Gly Gly<br>395 400 405 | 1554 |
| ttt ggc atc tgg aac acc gcc gtg cag gct gcc atc cgc gtg ggt gag<br>Phe Gly Ile Trp Asn Thr Ala Val Gln Ala Ala Ile Arg Val Gly Glu<br>410 415 420 | 1602 |
| tgg aag ctg ctg aca gga gac ccc ggc tat ggc gat tgg atc cca ccg<br>Trp Lys Leu Leu Thr Gly Asp Pro Gly Tyr Gly Asp Trp Ile Pro Pro<br>425 430 435 | 1650 |
| cag aca ctg gcc acc ttc ccg ggt agc tgg tgg aac ctg gaa cga atg<br>Gln Thr Leu Ala Thr Phe Pro Gly Ser Trp Trp Asn Leu Glu Arg Met<br>440 445 450 455 | 1698 |
| gcc agt gtc cgc cag gcc gtg tgg ctc ttc aac atc agt gct gac cct<br>Ala Ser Val Arg Gln Ala Val Trp Leu Phe Asn Ile Ser Ala Asp Pro<br>460 465 470 | 1746 |
| tat gaa cgg gag gac ctg gct ggc cag cgg cct gat gtg gtc cgc acc<br>Tyr Glu Arg Glu Asp Leu Ala Gly Gln Arg Pro Asp Val Val Arg Thr<br>475 480 485 | 1794 |
| ctg ctg gct cgc ctg gcc gaa tat aac cgc aca gcc atc ccg gta cgc<br>Leu Leu Ala Arg Leu Ala Glu Tyr Asn Arg Thr Ala Ile Pro Val Arg<br>490 495 500 | 1842 |
| tac cca gct gag aac ccc cgg gct cat cct gac ttt aat ggg ggt gct<br>Tyr Pro Ala Glu Asn Pro Arg Ala His Pro Asp Phe Asn Gly Gly Ala<br>505 510 515 | 1890 |
| tgg ggg ccc tgg gcc agt gat gag gaa gag gag gaa gag gaa ggg agg<br>Trp Gly Pro Trp Ala Ser Asp Glu Glu Glu Glu Glu Glu Glu Gly Arg | 1938 |

```
                520             525             530             535
gct cga agc ttc tcc cgg ggt cgt cgc aag aaa aaa tgc aag att tgc     1986
Ala Arg Ser Phe Ser Arg Gly Arg Arg Lys Lys Lys Cys Lys Ile Cys
                540                     545                 550 aag ctt cga tcc ttt ttc cgt aaa ctc aac acc agg cta atg tcc caa     2034
Lys Leu Arg Ser Phe Phe Arg Lys Leu Asn Thr Arg Leu Met Ser Gln
            555                 560                 565 cgg atc tga tggtggggag ggagaaaact gtcctttaga ggatcttccc             2083
Arg Ile * cactccggct tggccctgct gtttctcagg gagaagcctg tcacatctcc atctacaggg   2143
agttggaggg tgtagagtcc cttggttgaa cagggtaggg agcctggata ggagtgggtg   2203
ggaataaacc agactgggat gcctgtgtct cagtcctgcc tcctcacgga cttgctctgt   2263
gacctcaggt gacccacatg agcttttagc ctcagtttcc tcatctgtaa aatgagctct   2323
aatgactttg tgactctttg tgtggccct ggagcctggg gccacggtgg agttcctggc    2383
cggccttgcc acttgacaac tcctttaagg cttccccctt aacacgggat ccctgtggtg   2443
gtgtttggga gttgcctgga ggcaactcca agcctggccc ccagctgaag catggcaatc   2503
tggctgctct ctacagggac ccccaagcgc tgtgggtgga gggcagggt cggggggtt     2563 gaccttcttg ggtcttcaca tggcctaggc cagtcctccg gtcagactgg tgtcaggcac   2623
cgtggtgcaa aattcctctt ctggccctc cagtacccag agaaactggc tgggccatta   2683
actgctgcag caccaagggt ggtagaaaga gctgtgaaga gcccccaaac cagtaccagg   2743
acacctgggt tctcctgtga cctggggcac agttcttgcc ctctaggcct tgatttcccc   2803
acctgcaagt gggatgcca gccctggctc tgcctccttc atgaggctct ggaagactgg    2863
ccaaggttgt ggaggagctt gtgaacttga ttaaagtgtc gtaacatgga aaaaaaaaa    2923 aaaaaaaaaa agggcgg                                                  2940

<210> SEQ ID NO 7
<211> LENGTH: 550
<212> TYPE: PRT
<213> ORGANISM: homo sapiens

<400> SEQUENCE: 7

Met Ala Pro Arg Gly Cys Ala Gly His Pro Pro Pro Ser Pro Gln
1               5                   10                  15

Ala Cys Val Cys Pro Gly Lys Met Leu Ala Met Gly Ala Leu Ala Gly
            20                  25                  30

Phe Trp Ile Leu Cys Leu Leu Thr Tyr Gly Tyr Leu Ser Trp Gly Gln
        35                  40                  45

Ala Leu Glu Glu Glu Glu Gly Ala Leu Leu Ala Gln Ala Gly Glu
    50                  55                  60

Lys Leu Glu Pro Ser Thr Thr Ser Thr Ser Gln Pro His Leu Ile Phe
65                  70                  75                  80

Ile Leu Ala Asp Asp Gln Gly Phe Arg Asp Val Gly Tyr His Gly Ser
                85                  90                  95

Glu Ile Lys Thr Pro Thr Leu Asp Lys Leu Ala Ala Glu Gly Val Lys
            100                 105                 110

Leu Glu Asn Tyr Tyr Val Gln Pro Ile Cys Thr Pro Ser Arg Ser Gln
        115                 120                 125

Phe Ile Thr Gly Lys Tyr Gln Ile His Thr Gly Leu Gln His Ser Ile
    130                 135                 140

Ile Arg Pro Thr Gln Pro Asn Cys Leu Pro Leu Asp Asn Ala Thr Leu
```

```
             145                 150                 155                 160
Pro Gln Lys Leu Lys Glu Val Gly Tyr Ser Thr His Met Val Gly Lys
                165                 170                 175

Trp His Leu Gly Phe Tyr Arg Lys Glu Cys Met Pro Thr Arg Arg Gly
            180                 185                 190

Phe Asp Thr Phe Phe Gly Ser Leu Gly Ser Gly Asp Tyr Tyr Thr
            195                 200                 205

His Tyr Lys Cys Asp Ser Pro Gly Met Cys Gly Tyr Asp Leu Tyr Glu
            210                 215                 220

Asn Asp Asn Ala Ala Trp Asp Tyr Asp Asn Gly Ile Tyr Ser Thr Gln
225                 230                 235                 240

Met Tyr Thr Gln Arg Val Gln Gln Ile Leu Ala Ser His Asn Pro Thr
                245                 250                 255

Lys Pro Ile Phe Leu Tyr Ile Ala Tyr Gln Ala Val His Ser Pro Leu
                260                 265                 270

Gln Ala Pro Gly Arg Tyr Phe Glu His Tyr Arg Ser Ile Ile Asn Ile
                275                 280                 285

Asn Arg Arg Arg Tyr Ala Ala Met Leu Ser Cys Leu Asp Glu Ala Ile
290                 295                 300

Asn Asn Val Thr Leu Ala Leu Lys Thr Tyr Gly Phe Tyr Asn Asn Ser
305                 310                 315                 320

Ile Ile Ile Tyr Ser Ser Asp Asn Gly Gly Gln Pro Thr Ala Gly Gly
                325                 330                 335

Ser Asn Trp Pro Leu Arg Gly Ser Lys Gly Thr Tyr Trp Glu Gly Gly
            340                 345                 350

Ile Arg Ala Val Gly Phe Val His Ser Pro Leu Leu Lys Asn Lys Gly
            355                 360                 365

Thr Val Cys Lys Glu Pro Val His Ile Thr Asp Trp Tyr Pro Thr Leu
            370                 375                 380

Ile Ser Leu Ala Glu Gly Gln Ile Asp Glu Asp Ile Gln Leu Asp Gly
385                 390                 395                 400

Tyr Asp Ile Trp Glu Thr Ile Ser Glu Gly Leu Arg Ser Pro Arg Val
                405                 410                 415

Asp Ile Leu His Asn Ile Asp Pro Ile Tyr Thr Lys Ala Lys Asn Gly
            420                 425                 430

Ser Trp Ala Ala Gly Tyr Gly Ile Trp Asn Thr Ala Ile Gln Ser Ala
            435                 440                 445

Ile Arg Val Gln His Trp Lys Leu Leu Thr Gly Asn Pro Gly Tyr Ser
            450                 455                 460

Asp Trp Val Pro Pro Gln Ser Phe Ser Asn Leu Gly Pro Asn Arg Trp
465                 470                 475                 480

His Asn Glu Arg Ile Thr Ser Ser Thr Gly Lys Ser Val Trp Leu Phe
                485                 490                 495

Asn Ile Thr Ala Asp Pro Tyr Glu Arg Val Asp Leu Ser Asn Arg Tyr
            500                 505                 510

Pro Gly Ile Val Lys Lys Leu Leu Arg Arg Leu Ser Gln Phe Asn Lys
            515                 520                 525

Thr Ala Val Pro Val Arg Tyr Pro Pro Lys Asp Pro Arg Ser Asn Pro
            530                 535                 540

Arg Leu Asn Gly Gly Val
545                 550

<210> SEQ ID NO 8
```

-continued

```
<211> LENGTH: 2266
<212> TYPE: DNA
<213> ORGANISM: homo sapiens
<220> FEATURE:
<221> NAME/KEY: CDS
<222> LOCATION: (324)...(1977)

<400> SEQUENCE: 8
cacgcgtccg cccacgcgtc cgtggagata ttaactttt tctttttttt tttccttggt      60
ggaagctgct ctagggaggg gggaggagga ggagaaagtg aaatgtgctg agaagagcg      120 agccctcctt gttcttccgg agtcccatcc attaagccat cacttctgga agattaaagt    180
tgtcggacat ggtgacagct gagaggagag gaggatttct tgccaggtgg agagtcttca    240
ccgtctgttg ggtgcatgtg tgcgcccgca scggcgcggg gcgcgtggtt ctccgcgtgg    300
agtctcacct gggacctgag tga atg gct ccc agg ggc tgt gcg ggg cat ccg    353
                           Met Ala Pro Arg Gly Cys Ala Gly His Pro
                            1               5                  10 cct ccg cct tct cca cag gcc tgt gtc tgt cct gga aag atg cta gca      401
Pro Pro Pro Ser Pro Gln Ala Cys Val Cys Pro Gly Lys Met Leu Ala
                15                  20                  25 atg ggg gcg ctg gca gga ttc tgg atc ctc tgc ctc ctc act tat ggt      449
Met Gly Ala Leu Ala Gly Phe Trp Ile Leu Cys Leu Leu Thr Tyr Gly
        30                  35                  40 tac ctg tcc tgg ggc cag gcc tta gaa gag gag gaa gaa ggg gcc tta      497
Tyr Leu Ser Trp Gly Gln Ala Leu Glu Glu Glu Glu Glu Gly Ala Leu
    45                  50                  55 cta gct caa gct gga gag aaa cta gag ccc agc aca act tcc acc tcc      545
Leu Ala Gln Ala Gly Glu Lys Leu Glu Pro Ser Thr Thr Ser Thr Ser
60                  65                  70 cag ccc cat ctc att ttc atc cta gcg gat gat cag gga ttt aga gat      593
Gln Pro His Leu Ile Phe Ile Leu Ala Asp Asp Gln Gly Phe Arg Asp
75                  80                  85                  90 gtg ggt tac cac gga tct gag att aaa aca cct act ctt gac aag ctc      641
Val Gly Tyr His Gly Ser Glu Ile Lys Thr Pro Thr Leu Asp Lys Leu
                95                  100                 105 gct gcc gaa gga gtt aaa ctg gag aac tac tat gtc cag cct att tgc      689
Ala Ala Glu Gly Val Lys Leu Glu Asn Tyr Tyr Val Gln Pro Ile Cys
            110                 115                 120 aca cca tcc agg agt cag ttt att act gga aag tat cag ata cac acc      737
Thr Pro Ser Arg Ser Gln Phe Ile Thr Gly Lys Tyr Gln Ile His Thr
        125                 130                 135 gga ctt caa cat tct atc ata aga cct acc caa ccc aac tgt tta cct      785
Gly Leu Gln His Ser Ile Ile Arg Pro Thr Gln Pro Asn Cys Leu Pro
    140                 145                 150 ctg gac aat gcc acc cta cct cag aaa ctg aag gag gtt gga tat tca      833
Leu Asp Asn Ala Thr Leu Pro Gln Lys Leu Lys Glu Val Gly Tyr Ser
155                 160                 165                 170 acg cat atg gtc gga aaa tgg cac ttg ggt ttt tac aga aaa gaa tgc      881
Thr His Met Val Gly Lys Trp His Leu Gly Phe Tyr Arg Lys Glu Cys
                175                 180                 185 atg ccc acc aga aga gga ttt gat acc ttt ttt ggt tcc ctt ttg gga      929
Met Pro Thr Arg Arg Gly Phe Asp Thr Phe Phe Gly Ser Leu Leu Gly
            190                 195                 200 agt ggg gat tac tat aca cac tac aaa tgt gac agt cct ggg atg tgt      977
Ser Gly Asp Tyr Tyr Thr His Tyr Lys Cys Asp Ser Pro Gly Met Cys
        205                 210                 215 ggc tat gac ttg tat gaa aac gac aat gct gcc tgg gac tat gac aat      1025
Gly Tyr Asp Leu Tyr Glu Asn Asp Asn Ala Ala Trp Asp Tyr Asp Asn
    220                 225                 230
```

| | |
|---|---|
| ggc ata tac tcc aca cag atg tac act cag aga gta cag caa atc tta<br>Gly Ile Tyr Ser Thr Gln Met Tyr Thr Gln Arg Val Gln Gln Ile Leu<br>235                      240                  245                    250 | 1073 |
| gct tcc cat aac ccc aca aag cct ata ttt tta tat att gcc tat caa<br>Ala Ser His Asn Pro Thr Lys Pro Ile Phe Leu Tyr Ile Ala Tyr Gln<br>                      255                  260                    265 | 1121 |
| gct gtt cat tca cca ctg caa gct cct ggc agg tat ttc gaa cac tac<br>Ala Val His Ser Pro Leu Gln Ala Pro Gly Arg Tyr Phe Glu His Tyr<br>                270                  275                  280 | 1169 |
| cga tcc att atc aac ata aac agg agg aga tat gct gcc atg ctt tcc<br>Arg Ser Ile Ile Asn Ile Asn Arg Arg Arg Tyr Ala Ala Met Leu Ser<br>            285                  290                  295 | 1217 |
| tgc tta gat gaa gca atc aac aac gtg aca ttg gct cta aag act tat<br>Cys Leu Asp Glu Ala Ile Asn Asn Val Thr Leu Ala Leu Lys Thr Tyr<br>300                      305                  310 | 1265 |
| ggt ttc tat aac aac agc att atc att tac tct tca gat aat ggt ggc<br>Gly Phe Tyr Asn Asn Ser Ile Ile Ile Tyr Ser Ser Asp Asn Gly Gly<br>315                      320                  325                    330 | 1313 |
| cag cct acg gca gga ggg agt aac tgg cct ctc aga ggt agc aaa gga<br>Gln Pro Thr Ala Gly Gly Ser Asn Trp Pro Leu Arg Gly Ser Lys Gly<br>                335                  340                  345 | 1361 |
| aca tat tgg gaa gga ggg atc cgg gct gta ggc ttt gtg cat agc cca<br>Thr Tyr Trp Glu Gly Gly Ile Arg Ala Val Gly Phe Val His Ser Pro<br>            350                  355                  360 | 1409 |
| ctt ctg aaa aac aag gga aca gtg tgt aag gaa cct gtg cac atc act<br>Leu Leu Lys Asn Lys Gly Thr Val Cys Lys Glu Pro Val His Ile Thr<br>365                      370                  375 | 1457 |
| gac tgg tac ccc act ctc att tca ctg gct gaa gga cag att gat gag<br>Asp Trp Tyr Pro Thr Leu Ile Ser Leu Ala Glu Gly Gln Ile Asp Glu<br>380                      385                  390 | 1505 |
| gac att caa cta gat ggc tat gat atc tgg gag acc ata agt gag ggt<br>Asp Ile Gln Leu Asp Gly Tyr Asp Ile Trp Glu Thr Ile Ser Glu Gly<br>395                      400                  405                    410 | 1553 |
| ctt cgc tca ccc cga gta gat att ttg cat aac att gac ccc ata tac<br>Leu Arg Ser Pro Arg Val Asp Ile Leu His Asn Ile Asp Pro Ile Tyr<br>                415                  420                  425 | 1601 |
| acc aag gca aaa aat ggc tcc tgg gca gca ggc tat ggg atc tgg aac<br>Thr Lys Ala Lys Asn Gly Ser Trp Ala Ala Gly Tyr Gly Ile Trp Asn<br>            430                  435                  440 | 1649 |
| act gca atc cag tca gcc atc aga gtg cag cac tgg aaa ttg ctt aca<br>Thr Ala Ile Gln Ser Ala Ile Arg Val Gln His Trp Lys Leu Leu Thr<br>            445                  450                  455 | 1697 |
| gga aat cct ggc tac agc gac tgg gtc ccc cct cag tct ttc agc aac<br>Gly Asn Pro Gly Tyr Ser Asp Trp Val Pro Pro Gln Ser Phe Ser Asn<br>460                      465                  470 | 1745 |
| ctg gga ccg aac cgg tgg cac aat gaa cgg atc acc tcg tca act ggc<br>Leu Gly Pro Asn Arg Trp His Asn Glu Arg Ile Thr Ser Ser Thr Gly<br>475                      480                  485                    490 | 1793 |
| aaa agt gta tgg ctt ttc aac atc aca gcc gac cca tat gag agg gtg<br>Lys Ser Val Trp Leu Phe Asn Ile Thr Ala Asp Pro Tyr Glu Arg Val<br>                495                  500                  505 | 1841 |
| gac cta tct aac agg tat cca gga atc gtg aag aag ctc cta cgg agg<br>Asp Leu Ser Asn Arg Tyr Pro Gly Ile Val Lys Lys Leu Leu Arg Arg<br>            510                  515                  520 | 1889 |
| ctc tca cag ttc aac aaa act gca gtg ccg gtc agg tat ccc ccc aaa<br>Leu Ser Gln Phe Asn Lys Thr Ala Val Pro Val Arg Tyr Pro Pro Lys<br>            525                  530                  535 | 1937 |
| gac ccc aga agt aac cct agg ctc aat gga ggg gtc tag g gaccatggta<br>Asp Pro Arg Ser Asn Pro Arg Leu Asn Gly Gly Val *<br>540                      545                  550 | 1987 |

```
tagagaggaa accaagaaaa agaagccaag caaaaatcag gctgagaaaa agcaaaagaa    2047
aagcaaaaaa agaagaagaa acagcagaaa gcagtctcag gttcaacttg ccattcaggt    2107
gttacttgtg gataagcaca aatatttcct gtttggttaa actttaatca gttcttatct    2167
ttcatctgtt tcctaggtaa accagcaaat ttggctcgat aatatcgctg gcctaagcgt    2227
caggcttgtt ttcatgctgt gccacctggt gccgaattc                          2266
```

22438, 23553, 25278, AND 26212 NOVEL HUMAN SULFATASES

FIELD OF THE INVENTION

The present invention relates to newly identified human sulfatases. In particular, the invention relates to sulfatase polypeptides and polynucleotides, methods of detecting the sulfatase polypeptides and polynucleotides, and methods of diagnosing and treating sulfatase-related disorders. Also provided are vectors, host cells, and recombinant methods for making and using the novel molecules.

BACKGROUND OF THE INVENTION

The biology and functions of the reversible sulfation pathway catalyzed by human sulfotransferases and sulfatases has been reviewed by Coughtrie et al. (*Chemico-Biological Interactions* 109:3–27 (191998)). This review, summarized below, focuses on the sulfation of small molecules carried out by cytosolic sulfotransferases rather than the sulfation of macromolecules and lipids catalyzed by membrane-associated sulfotransferases.

Sulfation functions in the metabolism of xenobiotic compounds, steroid biosynthesis, and modulating the biological activity and inactivation and elimination of potent endogenous chemicals such as thyroid-hormones, steroids and catechols. This pathway is reversible, comprising the sulfotransferase enzymes that cause the sulfation and the sulfatases that hydrolyze the sulfate esters formed by the action of the sulfotransferases. Accordingly, the interplay between these families regulates the availability and biological activity of xenobiotic and endogenous chemicals. The sulfatases, including the arylsulfatases (ARS), are located in lysosomes or endoplasmic reticulum.

The presence of sulfated components depends upon the availability of key members of the sulfate pathway, i.e., substrate and activated sulfate donor molecule (co-substrate) and the balance between sulfation and sulfate conjugate hydrolysis that depends upon the activity and localization of the sulfotransferases and the sulfatases. Essentially, divalent sulfate is converted to adenosine 5' phosphosulfate (PAPS) by hydrolysis of ATP. This compound is in turn converted to 3' phosphoadenosine 5' phosphosulfate by hydrolysis of ATP to ADP. This compound is then converted to adenosine 3'5' biphosphate concurrently with the formation of 4-nitrophenolsulfate from 4-nitrophenol. An ARS would then cleave the monovalent sulfate from the 4-nitrophenolsulfate to produce the original 4nitrophenol. This forms the basis for the sulfation system in humans. Over- or under-production of any of these key molecules can result in sulfate-related disorders. For example, the brachymorphic mouse has a connective tissue disorder that results from a defect in PAPS formation that causes undersulfated cartilage proteoglycans.

ARS enzymes and their genes have been associated with specific genetic diseases. ARSA is located in the lysosomes and removes sulfate from sulfated glycolipids. A deficiency of ARSA has been associated with metachromatic leukodystrophy and multiple sulfatase deficiency (MSD). ARSB is located in lysosomes and has, as an endogenous substrate, dermatan sulfate and chondrotin sulfate. A deficiency of ARSB is associated with Maroteaux-Lamy syndrome and MSD. ARSC is located in the endoplasmic reticulum and has, as its endogenous substrate, cholesterol sulfate and steroid sulfates. A deficiency of ARSC is associated with X-linked ichthyosis and MSD. ARSD may be associated with MSD. ARSE has been associated with chondrodysplasia punctata and MSD. ARSF may be associated with MSD. ARSC hydrolyses sulfate esters on a wide range of steroids and cholesterol. ARSs also hydrolyse sulfate conjugates of xenobiotics.

MSD results from an inability to perform a co- or post-translational modification of a cysteine residue to serine semialdehyde (2-oxo-3-propionic acid). This residue is conserved in all eukaryotic sulfatases described by Coughtrie et at ARSC may have a very broad specificity, extending to iodothyronine sulfates and a number of sulfate conjugates of xenobiotic phenols.

The kinetic and catalytic properties of ARS enzymes in isolation, important for understanding substrate specificity and the physical and chemical properties of enzymes and substrates that allow substrate preference, have been characterized recently based on recombinant enzyme systems. For the expression of the human sulfotransferases, COS and V79 cells have been used. Coughtrie et al. have constructed and characterized V79 cell lines stably expressing ARSA, ARSB, and ARSC. These cell lines exhibited the expected substrate preferences of the three enzymes among the substrates 4-nitrocatechol sulfate, estrone sulfate, and dehydroepiandrosterone sulfate(DHEAS).

The sulfation of small molecules can be broadly divided into the areas of chemical defense, hormone biosynthesis, and bioactivation. It was originally viewed that sulfation protected against the toxic effects of xenobiotics in that sulfate conjugates are more readily excreted in urine or bile and generally exhibit reduced pharmacological/biological activity relative to the parent compound. Many drugs and other xenobiotics are conjugated with sulfate. Many phenolic metabolites of the cytochrome P450 mono-oxygenase system are excreted as sulfate conjugates.

Further, potent endogenous chemicals, such as steroids and catecholamines are found at high levels as circulating sulfate conjugates. For example, greater than 90% of circulating dopamine exists as the sulfated form. Sulfation is also suggested to play a role in the inactivation of potent steroids such as estrogens and androgens. Accordingly, sulfation is important in metabolism and homeostasis of such compounds in humans.

DHEAS is the major circulating steroid in humans and estrone sulfate is the major estrogen. These chemicals act as precursors of estrogens and androgens. Extremely large quantities of such steroids or estrogens may occur during various stages of development, such as pregnancy. Estrone sulfate is a precursor for β-estradiol synthesis. In breast cancer cells it is hydrolysed by steroid sulfatase (ARSC) to estrone which is then converted to β-estradiol by action of another enzyme. Accordingly, ARSC is important for maintaining active estrogen. It is thus an important therapeutic target for the treatment of breast cancer.

Cholesterol sulfate, synthesized in the skin epidermis, may have a role in keratinocyte differentiation. Accordingly, hydrolysis of cholesterol sulfate by steroid sulfatase may be important in skin formation and differentiation. This is the major organ affected in X-linked ichthyosis caused by mutations in ARSC.

Although sulfation may widely serve to detoxify potent compounds, some sulfate conjugates are more biologically active than the corresponding parent compound. Minoxidil and cicletanine are activated upon sulfation. Further, an inhibitor of ARSC was shown to potentiate the memory enhancing effect of DHEAS. This suggests a role for sulfates and sulfation in the central nervous system.

An important example of bioactivation by means of sulfation, however, occurs with dietary and environmental mutagens and carcinogens. For a large number of these, sulfation is the terminal step in the pathway to metabolic activation. Examples of such chemicals include aromatic amines (including heterocyclic amines) and benzylic alcohols of chemicals such as polycyclic aromatic hydrocarbons, safrole, and estragole.

The sulfatase gene family has been reviewed in Parenti et al. (*Current Opinion in Genetics and Development* 7:386–391 (1997)), summarized below.

The sulfatase family of enzymes is functionally and structurally similar. Nevertheless, these enzymes catalyze the hydrolysis of sulfate ester bonds from a wide variety of substrates ranging from complex molecules such as glycosaminoglycans and sulfolipids to steroid sulfates (see also Coughtrie et al, above). Several human genetic disorders result from the accumulation of intermediate sulfate compounds that result from a deficiency of single or multiple sulfatase activities. A subset of sulfatase, ARS, is characterized by the ability to hydrolyze sulfate esters of chromogenic or fluorogenic aromatic compounds such aspnitrocatechol sulfate and 4methylumbelliferyl sulfate. Desulfation is required to degrade glycosaminoglycans, heparan sulfate, chondroitin sulfate and dermatan sulfate and sulfolipids. Steroid sulfatase differs from other members of the family with respect to subcellular localization. It is localized in the microsomes rather than in lysosomes. Further, ARSD, ARSE, and ARSF are also non-lysosomal, being localized in the endoplasmic reticulum or Golgi compartment.

The natural substrate of ARSA is cerebroside sulfate. Associated diseases are MLD and MSD. The natural substrate of ARSB is dermatan sulfate. The disease associated with this enzyme is MPSVI and MSD. The natural substrate of ARSC/STS is sulfated steroids. Diseases associated with this enzyme are XLI and MSD. The natural substrates of ARSD-F are unknown. The natural substrates of iduronate-2-sulfate sulfatase (IDS) are dermatan sulfate and herparan sulfate. Diseases associated with this enzyme are MPSII and MSD. The natural substrate of galactose 6-sulfatase is keratan sulfate and chondroitin 6-sulfate. Diseases associated with this enzyme include MPSIVA and MSD. The natural substrate of glucosamine-6-sulfatase is heparan sulfate and keratan sulfate. A disease associated with this enzyme is MPSIIID and MSD. The natural substrate of glucuronate-2-sulfatase is heparan sulfate. The natural substrate of glucosamine-3-sulfatase is heparan sulfate.

Sulfatases are activated through conversion of a cysteine residue as described above. The conversion is required for catalytic activity and is defective in MSD. It is likely that all sulfatases undergo the same modification. The substitution of this cysteine was shown to destroy the enzymatic activity of N-acetyl galactosamine-1-sulfatase (ARSB). It has been shown that the modified residue and a metal ion are located at the base of a substrate binding pocket.

Nine human sulfatase genes are known and murine rat, goat, or avian orthologs for some of these have been identified. A high degree of similarity occurs particularly in the amino terminal region which contains accordingly a potential consensus sulfatase signature.

Sulfatases, as discussed above, are associated with human disease. Most sulfatase deficiencies cause lysosomal storage disorders. The mucopolysaccharidoses contain various associations of mental retardation, facial dysmorphisms, skeletal deformities, hepatosplenomegaly, and deformities of soft tissues caused by deficiencies of sulfatases acting on glycosaminoglycans. In metachromatic leukodystrophy, a deficiency of ARSA causes the storage of sulfolipids in the central and peripheral nervous systems, leading to neurologic deterioration. X-linked icythyosis is caused by STS deficiency leading to increased cholesterol sulfate levels. MSD, a disorder in which all sulfatase activities are simultaneously defective, was shown to result from a defect in the co- or post-translational processing of sulfatases.

Accordingly, sulfatases are a major target for drug action and development. Therefore, it is valuable to the field of pharmaceutical development to identify and characterize previously unknown sulfatases. The present invention advances the state of the art by providing previously unidentified human sulfatases.

SUMMARY OF THE INVENTION

Novel sulfatase nucleotide sequences, and the deduced sulfatase polypeptides are described herein. Accordingly, the invention provides isolated sulfatase nucleic acid molecules having the sequences shown in SEQ ID NOS:2, 4, 6, and 8 or in the cDNA deposited with ATCC as Patent Deposit Number PTA-1639 (which corresponds with SEQ ID NO:4), or PTA-1846 (which corresponds with SEQ ID NO:6) ("the deposited cDNA"), and variants and fragments thereof.

It is also an object of the invention to provide nucleic acid molecules encoding the sulfatase polypeptides, and variants and fragments thereof Such nucleic acid molecules are useful as targets and reagents in sulfatase expression assays, are applicable to treatment and diagnosis of sulfatase-related disorders and are useful for producing novel sulfatase polypeptides by recombinant methods.

The invention thus further provides nucleic acid constructs comprising the nucleic acid molecules described herein. In a preferred embodiment, the nucleic acid molecules of the invention are operatively linked to a regulatory sequence. The invention also provides vectors and host cells for expressing the sulfatase nucleic acid molecules and polypeptides, and particularly recombinant vectors and host cells.

In another aspect, it is an object of the invention to provide isolated sulfatase polypeptides and fragments and variants thereof, including a polypeptide having the amino acid sequence shown in SEQ ID NOS:1, 3, 5 or 7 or the amino acid sequences encoded by the deposited cDNAs. The disclosed sulfatase polypeptides are useful as reagents or targets in sulfatase assays and are applicable to treatment and diagnosis of sulfatase-related disorders.

The invention also provides assays for determining the activity of or the presence or absence of the sulfatase polypeptides or nucleic acid molecules in a biological sample, including for disease diagnosis. In addition, the invention provides assays for determining the presence of a mutation in the polypeptides or nucleic acid molecules, including for disease diagnosis.

A further object of the invention is to provide compounds that modulate expression of the sulfatase for treatment and diagnosis of sulfatase-related disorders. Such compounds may be used to treat conditions related to aberrant activity or expression of the sulfatase polypeptides or nucleic acids.

The disclosed invention further relates to methods and compositions for the study, modulation, diagnosis and treatment of sulfatase related disorders. The compositions include sulfatase polypeptides, nucleic acids, vectors, transformed cells and related variants thereof In particular, the invention relates to the diagnosis and treatment of sulfatase-related disorders including, but not limited to disorders as described in the background above, further herein, or involving a tissue shown in the figures herein.

In yet another aspect, the invention provides antibodies or antigen-binding fragments thereof that selectively bind the sulfatase polypeptides and fragments. Such antibodies and antigen binding fragments have use in the detection of the sulfatase polypeptide, and in the prevention, diagnosis and treatment of sulfatase related disorders.

The sulfatases disclosed herein are designated as follows: 22438, 23553, 25278, and 26212.

DESCRIPTION OF THE DRAWINGS

FIGS. 1A and 1B shows the 22438 sulfatase cDNA sequence (SEQ ID NO:2) and the deduced amino acid sequence (SEQ D NO:1).

FIG. 4 shows an analysis of the 22438 sulfatase open reading frame for amino acids corresponding to specific functional sites. For the N-glycosylation sites, the actual modified residue is the first amino acid. For cAMP- and cGMP-dependent protein kinase phosphorylation sites, the actual modified residue is the last amino acid. For protein kinase C phosphorylation sites, the actual modified residue is the first amino acid. For casein kinase II phosphorylation sites, the actual modified residue is the first amino acid. For N-myristoylation sites, the actual modified residue is the first amino acid. In addition, an amidation site is found from about amino acids 56–59, an EGF-like domain cysteine pattern signature found from about amino acids 260–271, and a sulfatase signature is found from about amino acids 129–138.

FIGS. 5A, 5B and 5C shows the 23553 sulfatase cDNA sequence (SEQ ID NO:4) and the deduced amino acid sequence (SEQ ID NO:3).

FIGS. 8A and 8B shows an analysis of the 23553 sulfatase open reading frame for amino acids corresponding to specific functional sites. For the N-glycosylation sites, the actual modified residue is the first amino acid. For protein kinase C phosphorylation sites, the actual modified residue is the first amino acid. For casein kinase II phosphorylation sites, the actual modified residue is the first amino acid. For the tyrosine kinase phosphorylation site, the actual modified residue is the last amino acid residue. For N-myristoylation sites, the actual modified residue is the first amino acid. In addition, a sulfatase signature is found from about amino acids 85–97.

FIG. 9 shows relative expression of the 23553 sulfatase mRNA in normal and cancerous human tissues.

FIGS. 10A and 10B shows the 25278 sulfatase cDNA sequence (SEQ ID NO:6) and the deduced amino acid sequence (SEQ ID NO:5).

FIG. 13 shows an analysis of the 25278 sulfatase open reading frame for amino acids corresponding to specific functional sites. For the N-glycosylation sites, the actual modified residue is the first amino acid. For cAMP- and cGMP-dependent protein kinase phosphorylation sites, the actual modified residue is the last amino acid. For protein kinase C phosphorylation sites, the actual modified residue is the first amino acid. For casein kinase II phosphorylation sites, the actual modified residue is the first amino acid. For the tyrosine kinase phosphorylation site, the actual modified residue is the last amino acid residue. For N-myristoylation sites, the actual modified residue is the first amino acid. In addition, amidation sites are found from about amino acids 312–315 and 541–544, and sulfatase signatures are found from about amino acids 139–148 and 91–103.

FIGS. 15A and 15B shows the 26212 sulfatase cDNA sequence (SEQ ID NO:8) and the deduced amino acid sequence (SEQ ID NO:7).

FIGS. 18A and 18B shows an analysis of the 26212 sulfatase open reading frame for amino acids corresponding to specific functional sites. For the N-glycosylation sites, the actual modified residue is the first amino acid. For cAMP- and cGMP-dependent protein kinase phosphorylation sites, the actual modified residue is the last amino acid. For protein kinase C phosphorylation sites, the actual modified residue is the first amino acid. For casein kinase II phosphorylation sites, the actual modified residue is the first amino acid. For the tyrosine kinase phosphorylation site, the actual modified residue is the last amino acid residue. For N-myristoylation sites, the actual modified residue is the first amino acid. In addition, sulfatase signature sites are found from about amino acids 168–177 and 120–132.

DETAILED DESCRIPTION OF THE INVENTION

Sulfatase Polypeptides

Figure 2:
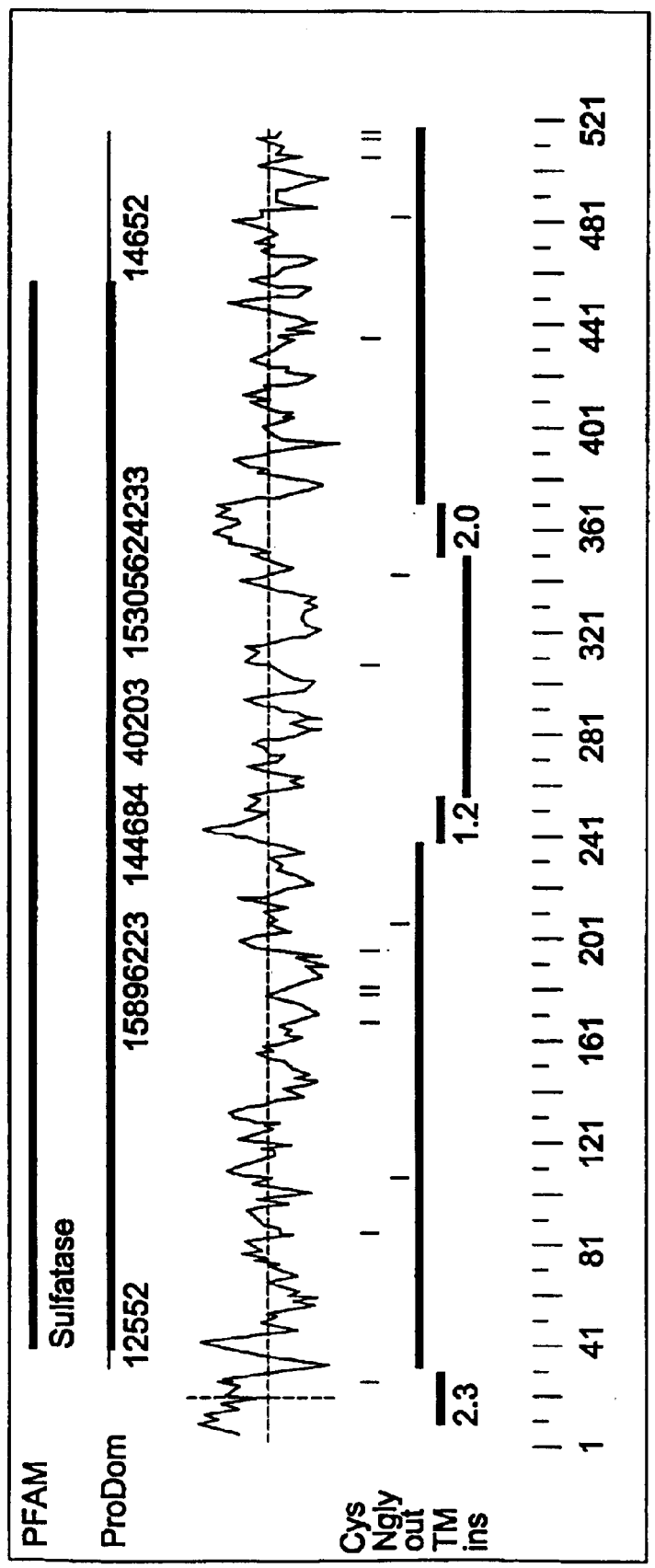
FIG. 2 shows a 22438 sulfatase hydrophobicity plot.
Figure 3:
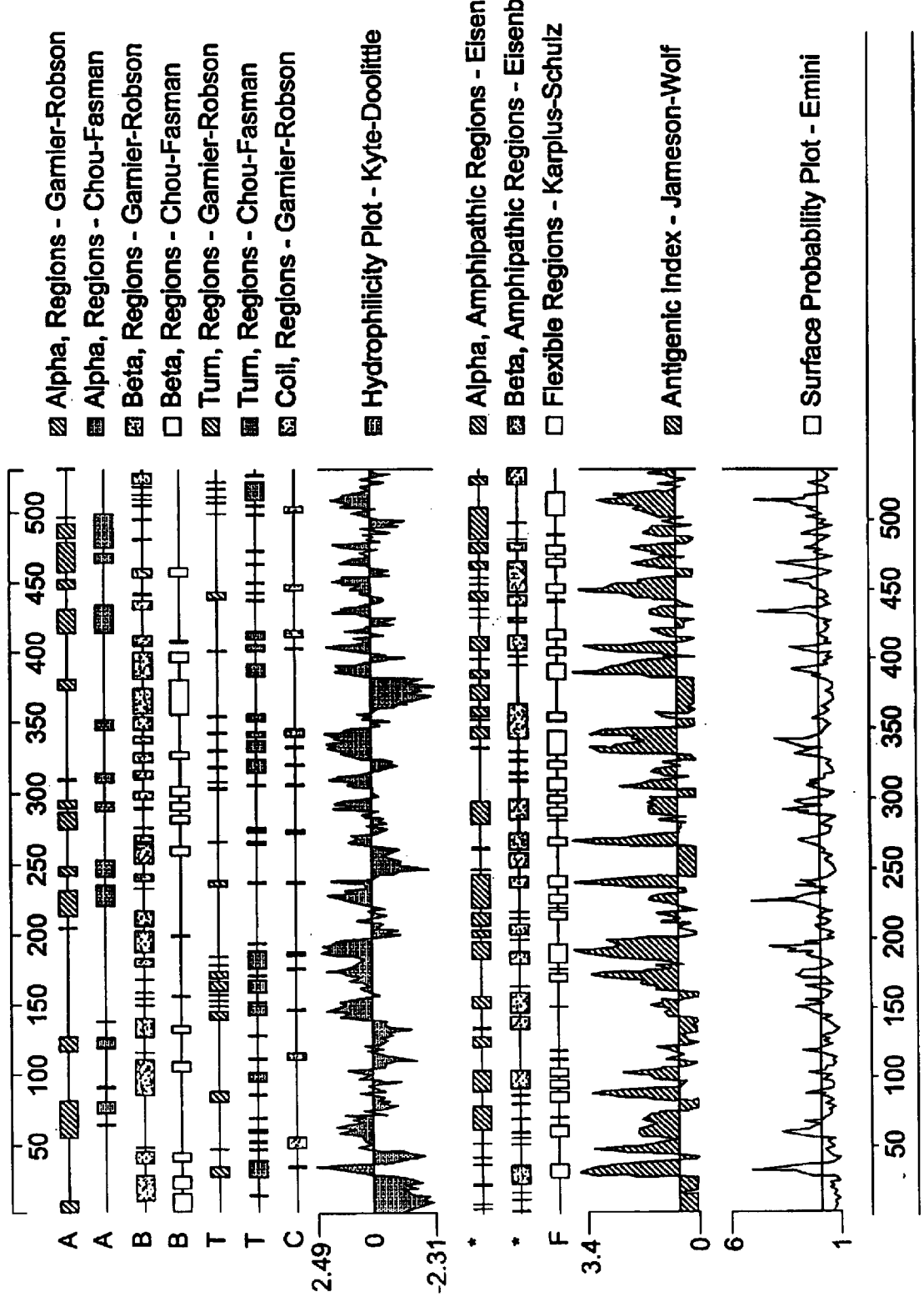
FIG. 3 shows an analysis of the 22438 sulfatase amino acid sequence: αβturn and coil regions; hydrophilicity; amphipathic regions; flexible regions; antigenic index, and surface probability plot.
Figure 6:
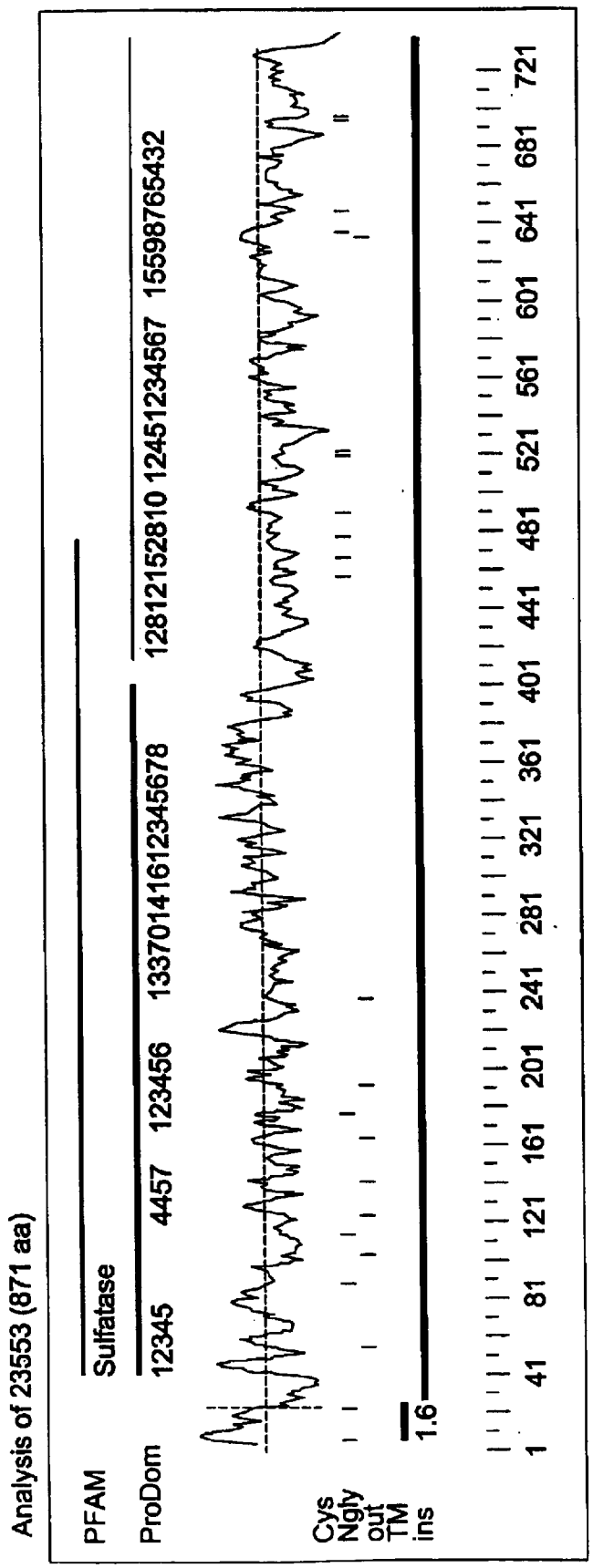
FIG. 6 shows a 23553 sulfatase hydrophobicity plot.
Figure 7:
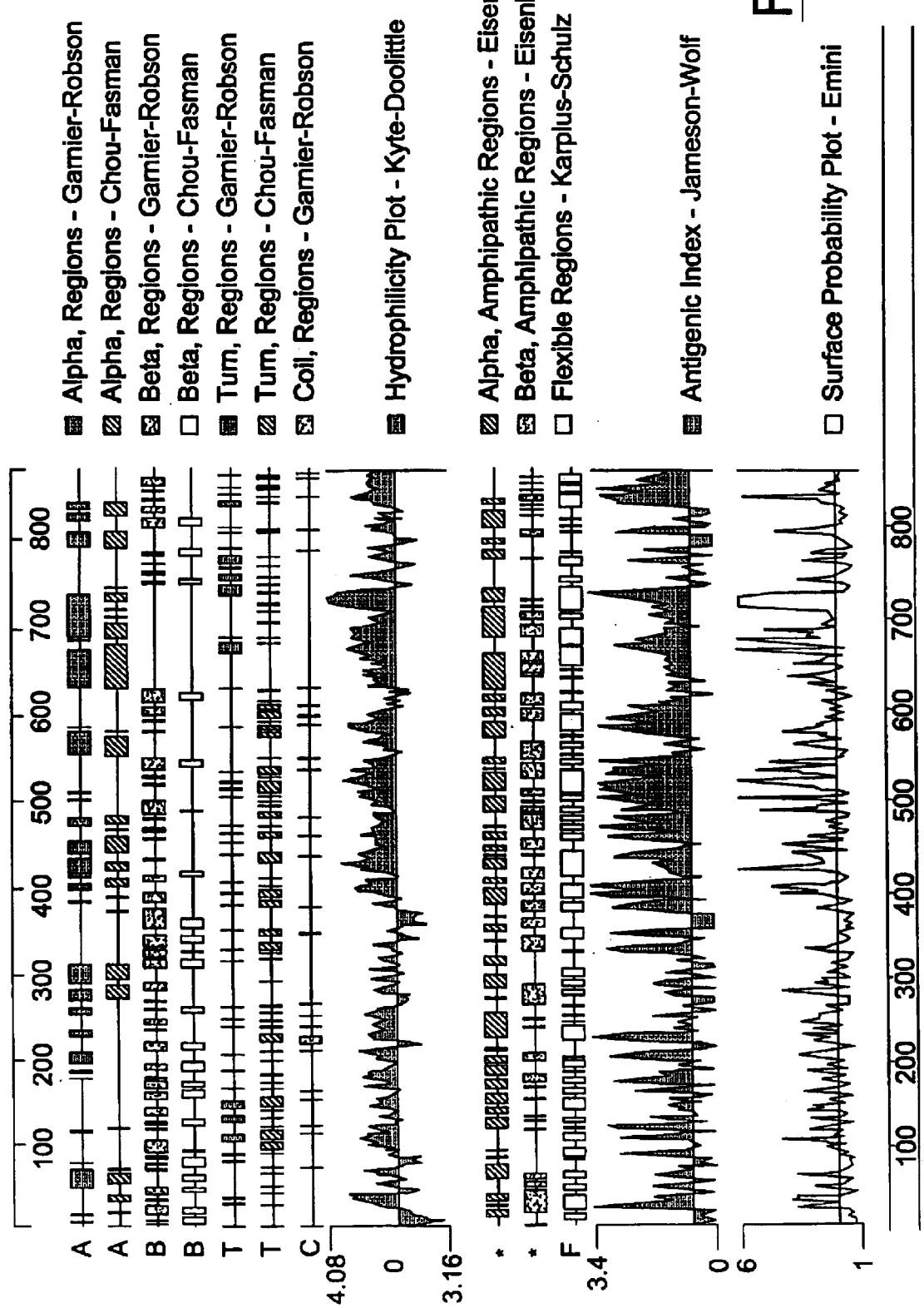
FIG. 7 shows an analysis of the 23553 sulfatase amino acid sequence: αβturn and coil regions; hydrophilicity; amphipathic regions, flexible regions; antigenic index; and surface probability plot.
Figure 11:
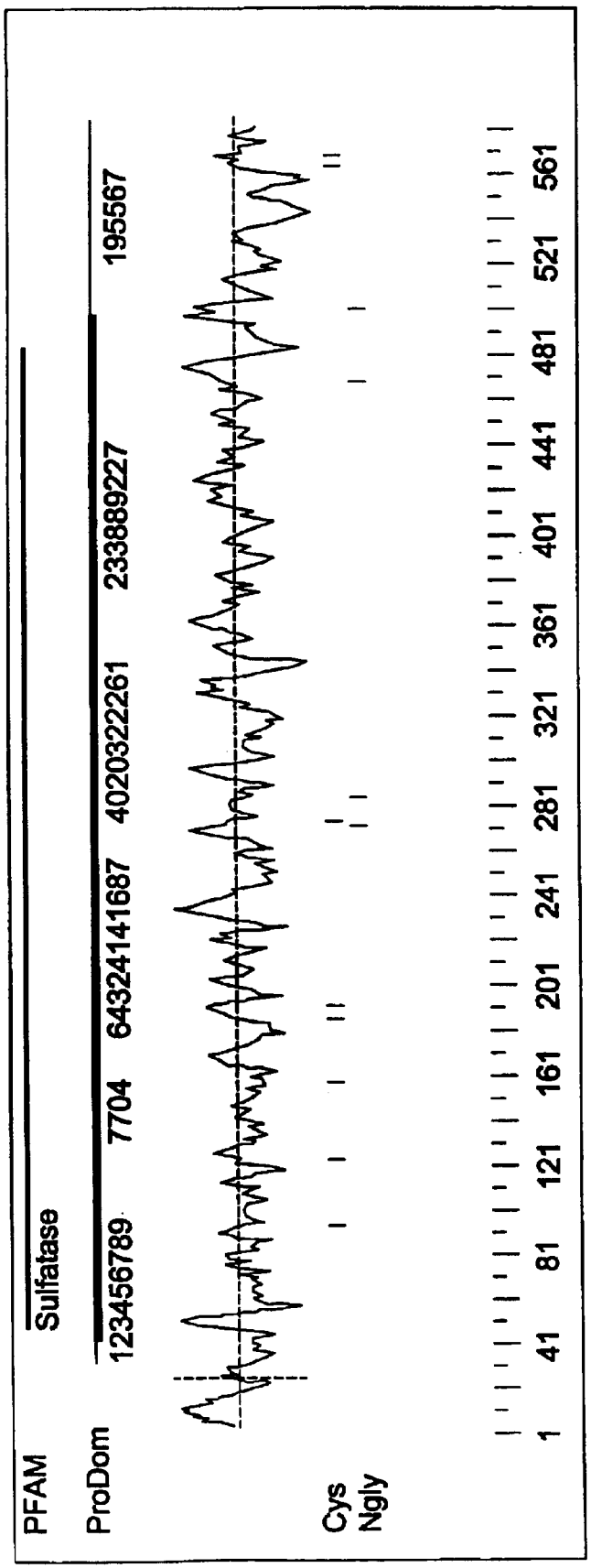
FIG. 11 shows a 25278 sulfatase hydrophobicity plot.
Figure 12:
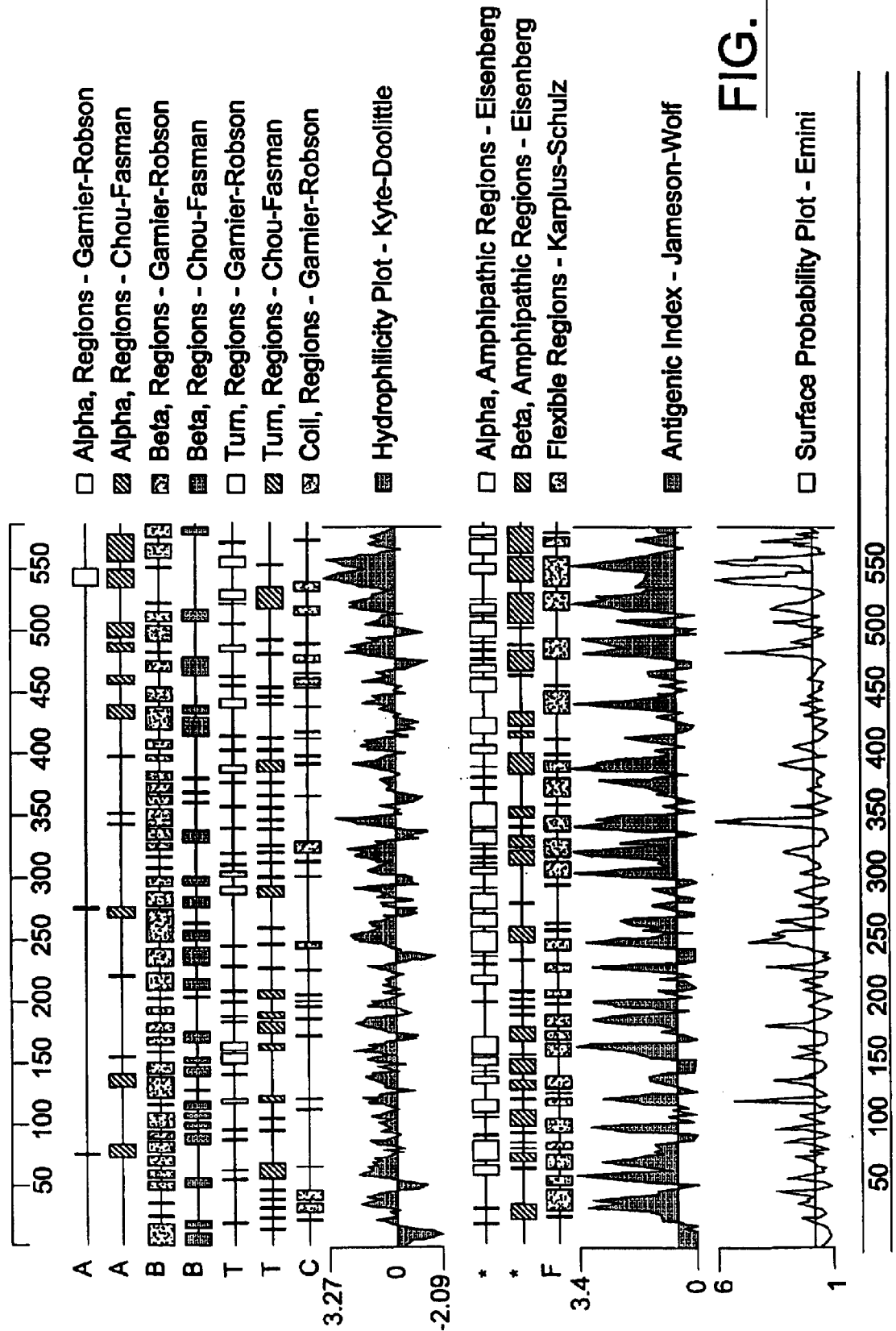
FIG. 12 shows an analysis of the 25278 sulfatase amino acid sequence: αβturn and coil regions; hydrophilicity; amphipathic regions; flexible regions; antigenic index; and surface probability plot.

The invention is based on the identification of the novel human 22438 sulfatase. In situ hybridization experiments showed that this sulfatase is expressed in the following monkey tissues: sub-populations of DRG neurons (mainly in small and medium sized neurons), in spinal cord (interneurons and motor neurons), and in the brain. The sulfatase is also expressed in human brain. The sulfatase cDNA was identified based on consensus motifs or protein domains characteristic of sulfatases and, in particular, arylsulfatase. BLAST analysis has shown homology with human arylsulfatase E, a human iduronate-2-sulfatase, human N-acetylgalactosamine-6-sulfatase, murine arylsulfatase A, and human arylsulfatase A. However, some homology has also been found with other arylsulfatases from various mammalian species, including, but not limited to, human arylsulfatase D, E, F, and B.

The invention is also based on the identification of the novel human 23553 sulfatase. Taqman analysis has shown positive differential expression in breast and colon cancer and in colonic metastases to the liver (FIG. 9). This sulfatase has been identified as a glucosamine-6-sulfatase based on ProDom matches and BLAST analysis. Some homology has also been found to human arylsulfatase A, human N-acetylglucosamine-6-sulfatase, and human iduronate-2-sulfatase.

The invention is also based on the identification of the novel human 25278 sulfatase. The sulfatase is differentially expressed in human colon cancer and in colonic metastases to the liver, as determined by Taqman analysis. This sulfatase has been identified as a N-acetylgalactosamine-4-sulfatase by ProDom matching and BLAST homology alignment. Further, based on BLAST analysis, some homology has also been shown to arylsulfatase B and arylsulfatase A The invention is also based on the identification of the novel human 26212 sulfatase. This sulfatase has been identified as an arylsulfatase by ProDom matching and BLAST sequence alignment. Homology has been shown to arylsulfatase B. Some homology has also been found with arylsulfatase F, E, D, and A, as well as with iduronate 2 sulfatase. Arylsulfatase B is also known as N-acetylgalactosamine-4-sulfatase.

Specifically, newly-identified human genes, termed 22438, 23553, 25278, and 26212 sulfatases are provided. These sequences, and other nucleotide sequences encoding the sulfatase proteins or fragments and variants thereof, are referred to as "22438, 23553, 25278, and 26212 sulfatase sequences."

Plasmids containing the sulfatase cDNA inserts were deposited with the Patent Depository of the American Type Culture Collection (ATCC), 10801 University Boulevard, Manassas, Va., on Apr. 5, 2000 or May 9, 2000 and assigned Patent Deposit Numbers PTA-1639 or PTA-1846, respectively. The deposits will be maintained under the terms of the Budapest Treaty on the International Recognition of the Deposit of Microorganisms for the Purposes of Patent Procedure. The deposits were made merely as a convenience for those of skill in the art and is not an admission that a deposit is required under 35 U.S.C. § 112.

The sulfatase cDNA was identified in human cDNA libraries. Specifically, expressed sequence tags (EST) found in human cDNA libraries, were selected based on homology to known sulfatase sequences. Based on such EST sequences, primers were designed to identify a full length clone from a human cDNA library. Positive clones were sequenced and the overlapping fragments were assembled. The 22438, 23553, 25278, and 26212 sulfatase amino acid sequences are shown in FIGS. 1, 5, 10, and 15, respectively, and SEQ ID NOS:1, 3, 5, and 7. The 22438, 23553, 25278, and 26212 sulfatase cDNA sequences are shown in FIGS. 1, 5, 10, and 15 and SEQ ID NOS:2, 4, 6, and 8.

Analysis of the assembled sequences revealed that the cloned cDNA molecules encoded sulfatase-like polypeptides. BLAST analysis indicated that the 23553 sulfatase is a glucosamine-6-sulfatase, that the 25278 sulfatase is an N-acetylgalactosamine-4-sulfatase, that the 22438 is an arylsulfatase with highest homology to arylsulfatase A and E genes and that the 26212 sulfatase is an arylsulfatase with highest homology to the arylsulfatase B gene (N-acetylgalactosamine-4-sulfatase).

The sulfatase sequences of the invention belong to the sulfatase family of molecules having conserved functional features. The term "family" when referring to the proteins and nucleic acid molecules of the invention is intended to mean two or more proteins or nucleic acid molecules having sufficient amino acid or nucleotide sequence identity as defined herein to provide a specific function. Such family members can be naturally-occurring and can be from either the same or different species. For example, a family can contain a first protein of murine origin and an ortholog of that protein of human origin, as well as a second, distinct protein of human origin and a murine ortholog of that protein.

The 22438 sulfatase gene encodes an approximately 2175 nucleotide mRNA transcript having the corresponding cDNA set forth in SEQ ID NO:2. This transcript has an open reading frame which encodes a 525 amino acid protein (SEQ ID NO:1).

The 23553 sulfatase gene encodes an approximately 4321 nucleotide mRNA transcript having the corresponding cDNA set forth in SEQ ID NO:4. This transcript has an open reading frame which encodes an 871 amino acid protein (SEQ ID NO:3).

The 25278 sulfatase gene encodes an approximately 2940 nucleotide mRNA transcript having the corresponding cDNA set forth in SEQ ID NO:6. This transcript has an open reading frame which encodes a 569 amino acid protein (SEQ ID NO:5).

The 26212 sulfatase gene encodes an approximately 2266 nucleotide mRNA transcript having the corresponding cDNA set forth in SEQ ID NO:8. This transcript has an open reading frame which encodes a 550 amino acid protein (SEQ ID NO:7).

Prosite program analysis was used to predict various sites within the 22438 sulfatase protein as shown in FIG. 4.

Prosite program analysis was used to predict various sites within the 23553 sulfatase protein as shown in FIG. 8.

Prosite program analysis was used to predict various sites within the 25278 sulfatase protein as shown in FIG. 13.

Prosite program analysis was used to predict various sites within the 26212 sulfatase protein as shown in FIG. 18.

In situ hybridization experiments showed that 22438 is expressed in subpopulations of DRG neurons, spinal cord, and brain, as disclosed hereinabove.

Expression of the 22438 sulfatase mRNA in the above cells and tissues indicates that the sulfatase is likely to be involved in the proper function of and in disorders involving these tissues. Accordingly, the disclosed invention further relates to methods and compositions for the study, modulation, diagnosis and treatment of sulfatase related disorders, especially disorders of these tissues that include, but are not limited to those disclosed herein.

The 23553 sulfatase is differentially expressed in breast and colon cancer and in colonic metastases to the liver. Accordingly, the disclosed invention further relates to methods and compositions for the study, modulation, diagnosis and treatment in these tissues (normal and tumor).

The 25278 sulfatase is differentially expressed in colon tumors and colonic metastases to the liver. Accordingly, the disclosed invention further relates to methods and compositions for the study, modulation, diagnosis and treatment in these normal and tumor tissues.

The compositions include sulfatase polypeptides, nucleic acids, vectors, transformed cells and related variants and fragments thereof, as well as agents that modulate expression of the polypeptides and polynucleotides. In particular, the invention relates to the modulation, diagnosis and treatment of sulfatase related disorders as described herein.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system, transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Furthermore, as disclosed in the background hereinabove, specific disorders have been associated with function of the various sulfatases. Accordingly, the sulfatases disclosed herein, having homology to specific sulfatases as disclosed herein, are useful for diagnosis and treatment of the disorders associated with sufatase dysfunction as disclosed herein and to modulation of gene expression in the affected tissues.

The sequences of the invention find use in diagnosis of disorders involving an increase or decrease in sulfatase expression relative to normal expression, such as a proliferative disorder, a differentiative disorder, or a developmental disorder. The sequences also find use in modulating sulfatase-related responses. By "modulating" is intended the upregulating or downregulating of a response. That is, the compositions of the invention affect the targeted activity in either a positive or negative fashion.

The invention relates to novel sulfatases, having the deduced amino acid sequence shown in FIGS. 1, 5, 10, and 15 (SEQ ID NOS:1, 3, 5, and 7) or having the amino acid sequences encoded by the deposited cDNAs, Patent Deposit Numbers PTA-1639 or PTA-1846. The deposited sequences, as well as the polypeptides encoded by the sequences, are incorporated herein by reference and control in the event of any conflict, such as a sequencing error, with description in this application.

Thus, the present invention provides an isolated or purified sulfatase polypeptides and variants and fragments thereof. "Sulfatase polypeptide" or "sulfatase protein" refers to the polypeptide in SEQ ID NOS:1, 3, 5, or 7 or encoded by the deposited cDNAs. The term "sulfatase protein" or "sulfatase polypeptide," however, further includes the numerous variants described herein, as well as fragments derived from the full-length sulfatase and variants.

Sulfatase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

In one embodiment, the language "substantially free of cellular material" includes preparations of sulfatase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

The sulfatase polypeptide is also considered to be isolated when it is part of a membrane preparation or is purified and then reconstituted with membrane vesicles or liposomes.

The language "substantially free of chemical precursors or other chemicals" includes preparations of the sulfatase polypeptide in which it is separated from chemical precursors or other chemicals that are involved in its synthesis. The language "substantially free of chemical precursors or other chemicals" includes, but is not limited to, preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the sulfatase polypeptide comprises the amino acid sequence shown in SEQ ID NOS:1, 3, 5, or 7. However, the invention also encompasses sequence variants. Variants include a substantially homologous protein encoded by the same genetic locus in an organism, i.e., an allelic variant. Variants also encompass proteins derived from other genetic loci in an organism, but having substantial homology to the sulfatase of SEQ ID NOS:1, 3, 5, or 7. Variants also include proteins substantially homologous to the sulfatase but derived from another organism, i.e., an ortholog. Variants also include proteins that are substantially homologous to the sulfatase that are produced by chemical synthesis. Variants also include proteins that are substantially homologous to the sulfatase that are produced by recombinant methods. It is understood, however, that variants exclude any amino acid sequences disclosed prior to the invention.

Preferred sulfatase polypeptides of the present invention have an amino acid sequence sufficiently identical to the amino acid sequence of SEQ ID NOS:1, 3, 5, or 7. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 50%, 55%, 60%, or 65% identity, preferably 70–75% identity, more preferably 75–80%, 85–90%, 91%, 92%, 93%, 94%, 95%, 96%, 97%, 98% or 99% identity are defined herein as sufficiently identical.

In one embodiment, a variant of the 23553 sulfatase is greater than 92% homologous. In another embodiment, a variant of the 25278 sulfatase is greater than 50% identical. In another embodiment, the 26212 sulfatase is greater than 50% identical.

The determination of percent identity between two sequences using the algorithms of Karlin and Altschul (1990) *Proc. Natl. Acad. Sci. USA* 87:2264, modified as in Karlin and Altschul (1993) *Proc. Natl. Acad Sci. USA* 90:5873–5877. Such an algorithm is incorporated into the NBLAST and XBLAST programs of Altschul et at. (1990) *J. Mol. Biol.* 215:403. BLAST nucleotide searches can be performed with the NBLAST program, score=100, wordlength=12, to obtain nucleotide sequences homologous to the sulfatase nucleic acid molecules of the invention. BLAST protein searches can be performed with the XBLAST program, score=50, wordlength=3, to obtain amino acid sequences homologous to the sulfatase molecules of the invention. When utilizing BLAST programs, the default parameters of the respective programs (e.g., XBLAST and NBLAST) can be used. See http://www.ncbi.nlm.nih.gov.

As used herein, two proteins (or a region of the proteins) are substantially homologous when the amino acid sequences are at least about 50–55%, 55–60%, 60–65%, 65–70%, 70–75%, 75–80%, typically at least about 80–85%, 85–90%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NOS:2, 4, 6, or 8 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 401%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the sulfatase. Similarity is determined by conservative amino acid substitution, as shown in Table 1. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:130–1310 (1990).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |

TABLE 1-continued

Conservative Amino Acid Substitutions

| | |
|---|---|
| Small | Alanine |
| | Serine |
| | Threonine |
| | Methionine |
| | Glycine |

A variant polypeptide can differ in amino acid sequence by one or more substitutions, deletions, insertions, inversions, fusions, and truncations or a combination of any of these. Variant polypeptides can be fully functional or can lack function in one or more activities. Thus, in the present case, variations can affect the function, for example, of one or more of regions including a metal (e.g., $Ca^{++}$)-binding domain, activation domain, sulfatase catalytic domain, the region containing a propeptide, regulatory regions, substrate binding regions, regions involved in membrane association or subcellular localization, regions involved in post-translational modification, for example, by phosphorylation, and regions that are important for effector function (i.e., agents that act upon the protein, such as in the conversion of cysteine to 2-amino-3-oxoproprionic acid or serine semi-aldehyde).

Fully functional variants typically contain only conservative variation or variation in non-critical residues or in noncritical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the sulfatase polypeptide. This includes preventing immunogenicity from pharmaceutical formulations by preventing protein aggregation.

Useful variations further include alteration of functional activity. For example, one embodiment involves a variation at the substrate binding site that results in binding but not hydrolysis or more or less hydrolysis of the substrate than wild type. A further useful variation at the same site can result in altered affinity for the substrate. Useful variations also include changes that provide for affinity for another substrate. Useful variations further include the ability to bind an effector molecule with greater or lesser affinity, such as not to bind or to bind but not release it. Further useful variations include alteration in the ability of the propeptide to be cleaved by a cleavage protein, including alteration in the binding or recognition site. Further, the cleavage site can also be modified so that recognition and cleavage are by a different protease. A specific useful variation involves a variation in the ability to be bound or activated by the enzyme that activates the sulfatase by the conversion of cysteine to 2–3-oxoproprionic acid or serine semi-aldehyde. Further variation could include a variation in the specificity of metal binding.

Another useful variation provides a fusion protein in which one or more domains or subregions are operationally fused to one or more domains, subregions, or motifs from another sulfatase. For example, a transmembrane domain from a protein can be introduced into the sulfatase such that the protein is anchored in the cell surface. Other permutations include changing the number of sulfatase domains, and mixing of sulfatase domains from different sulfatase families, so that substrate specificity is altered. Mixing these various domains can allow the formation of novel sulfatase molecules with different host cell, subcellular localization, substrate, and effector molecule (one that acts on the sulfatase) specificity.

The term "substrate" is intended to refer not only to the sulfated substrate that is cleaved by the sulfatase domain, but to refer to any component with which the polypeptide interacts in order to produce an effect on that component or a subsequent biological effect that is a result of interacting with that component. This can include, but is not limited to, for example, interaction with the sulfatase activation enzyme and components involved in the conversion of 3' phosophoadenosine 5' phosphosulfate to adenosine 3'5' biphosphate.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as peptide bond hydrolysis in vitro or related biological activity, such as proliferative activity. Sites that are critical for binding can also be determined by structural analysis such as crystallization, nuclear magnetic resonance or photoaffinity labeling (Smith et al (1992) *J. Mol. Biol.* 224:899–904; de Vos et al. (1992) *Science* 255:306–312).

The invention thus also includes polypeptide fragments of the sulfatases. Fragments can be derived from the amino acid sequence shown in SEQ ID NOS:1, 3, 5, or 7. However, the invention also encompasses fragments of the variants of the sulfatase polypeptides as described herein. The fragments to which the invention pertains, however, are not to be construed as encompassing fragments that may be disclosed prior to the present invention.

A fragment can comprise at least about 10, 11, 12, 13, 14, 15, 16, 17, 18, 19, 20, 21, 22, 23, 24, 25, 30, 35, 40, 45, 50 or more contiguous amino acids. Fragments can retain one or more of the biological activities of the protein, for example as discussed above, as well as fragments that can be used as an immunogen to generate sulfatase antibodies.

For example, for the 25278 sulfatase, the invention encompasses amino acid fragments greater than 5 amino acids, particularly from regions up to around nucleotide 450 and beyond around nucleotide 1520. Specific fragments which may be excluded include those that are underlined in FIG. 1. However, even in regions between around nucleotide 450 to around nucleotide 1520, fragments include those that are five or greater excluding those which may have been disclosed prior to the present invention.

For the 23553 sulfatase, fragments particularly include fragments of 5 amino acids or more up to around nucleotide 670.

For the 26212 sulfatase, for example, fragments containing 5 or more amino acids up to about nucleotide 572 are particularly encompassed by the invention. However, fragments of 5 amino acids or more encoded by around nucleotide 572 to around nucleotide 1985 are also encompassed by the invention with the understanding that such fragments do not encompass those which may have been disclosed prior to the invention. For example, these can include the sections underlined in FIG. 15.

Biologically active fragments (peptides which are, for example, about 5, 10, 15, 20, 25, 30, 35, 40, 50, 100 or more amino acids in length) can comprise a functional site. Such sites include but are not limited to those discussed above, such as a catalytic site, regulatory site, site important for substrate recognition or binding, regions containing a sulfatase domain or motif, phosphorylation sites, glycosylation sites, and other functional sites disclosed herein.

Fragments, for example, can extend in one or both directions from the functional site to encompass 5, 10, 15, 20, 30, 40, 50, or up to 100 amino acids. Further, fragments can include sub-fragments of the specific sites or regions disclosed herein, which sub-fragments retain the function of the site or region from which they are derived.

The invention also provides fragments with immunogenic properties. These contain an epitope-bearing portion of the sulfatase polypeptide and variants. These epitope-bearing peptides are useful to raise antibodies that bind specifically to a sulfatase polypeptide or region or fragment. These peptides can contain at least 10, 12, at least 14, or between at least about 15 to about 30 amino acids. The epitope-bearing sulfatase polypeptides may be produced by any conventional means (Houghten, R. A. (1985) *Proc. Natl. Acad Sci. USA* 82:5131–5135). Simultaneous multiple peptide synthesis is described in U.S. Pat. No. 4,631,211.

Non-limiting examples of antigenic polypeptides that can be used to generate antibodies include but are not limited to peptides derived from extracellular regions. Regions having a high antigenicity index are shown in FIGS. 3, 7, 12, and 17. However, intracellularly-made antibodies ("intrabodies") are also encompassed, which would recognize intracellular peptide regions.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the sulfatase polypeptide fragment and an additional region fused to the carboxyl terminus of the fragment.

The invention thus provides chimeric or fusion proteins. These comprise a sulfatase peptide sequence operatively linked to a heterologous peptide having an amino acid sequence not substantially homologous to the sulfatase polypeptide. "Operatively linked" indicates that the sulfatase polypeptide and the heterologous peptide are fused in-frame. The heterologous peptide can be fused to the N-terminus or C-terminus of the sulfatase polypeptide or can be internally located.

In one embodiment the fusion protein does not affect sulfatase function per se. For example, the fusion protein can be a GST-fusion protein in which sulfatase sequences are fused to the N- or C-terminus of the GST sequences. Other types of fusion proteins include, but are not limited to, enzymatic fusion proteins, for example beta-galactosidase fusions, yeast two-hybrid GAL4 fusions, poly-His fusions and Ig fusions. Such fusion proteins, particularly poly-His fusions, can facilitate the purification of recombinant sulfatase polypeptide. In certain host cells (e.g., mammalian host cells), expression and/or secretion of a protein can be increased by using a heterologous signal sequence. Therefore, in another embodiment, the fusion protein contains a heterologous signal sequence at its C- or N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing a sulfatase polypeptide and various portions of the constant regions of heavy or light chains of immunoglobulins of various subclass (IgG, IgM IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A sulfatase-encoding nucleic acid can be cloned into such an expression vector such that the fusion moiety is linked in-frame to sulfatase.

Another form of fusion protein is one that directly affects sulfatase functions. Accordingly, a sulfatase polypeptide is encompassed by the present invention in which one or more of the sulfatase regions (or parts thereof) has been replaced by heterologous or homologous regions (or parts thereof) from another sulfatase. Accordingly, various permutations are possible, for example, as discussed above. Thus, chimeric sulfatases can be formed in which one or more of the native domains or subregions has been duplicated, removed, or replaced by another. This includes but is not limited to catalytic sulfatase or substrate binding domains, and regions involved in activation.

It is understood however that such regions could be derived from a sulfatase that has not yet been characterized. Moreover, sulfatase function can be derived from peptides that contain these functions but are not in a sulfatase family.

The isolated 22438 sulfatase protein can be purified from cells that naturally express it, such as DRG neurons, including small and medium sized neurons, spinal cord, including interneurons and motor neurons, and brain, especially purified from cells that have been altered to express it (recombinant), or synthesized using known protein synthesis methods.

The isolated 23553 sulfatase protein can be purified from cells that naturally express it, such as cells from any of the tissues shown in FIG. 9, especially purified from cells that have been altered to express it (recombinant), or synthesized using known protein synthesis methods.

Figure 14:
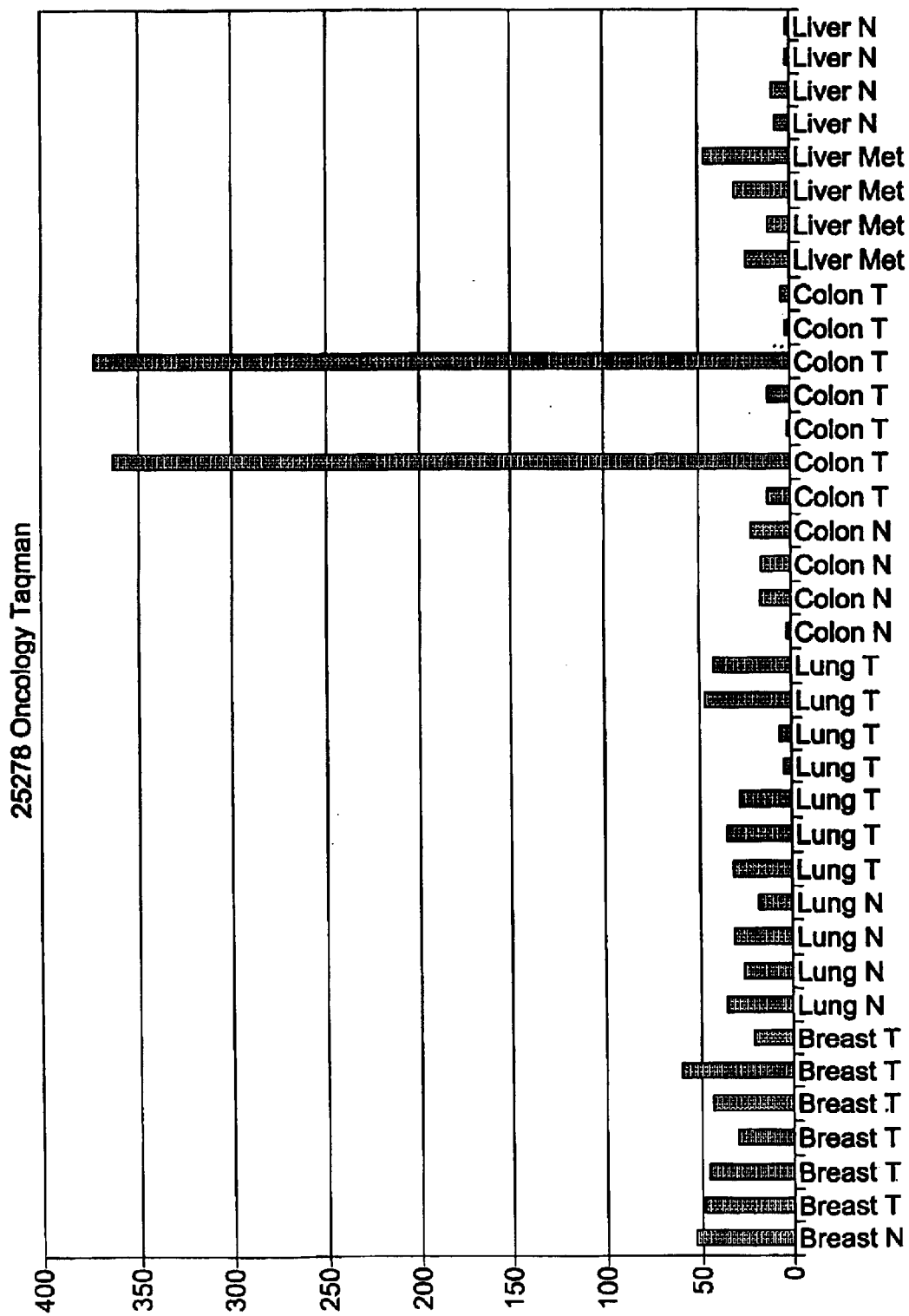
FIG. 14 shows relative expression of sulfatase mRNA in normal and cancerous human tissues.
Figure 16:
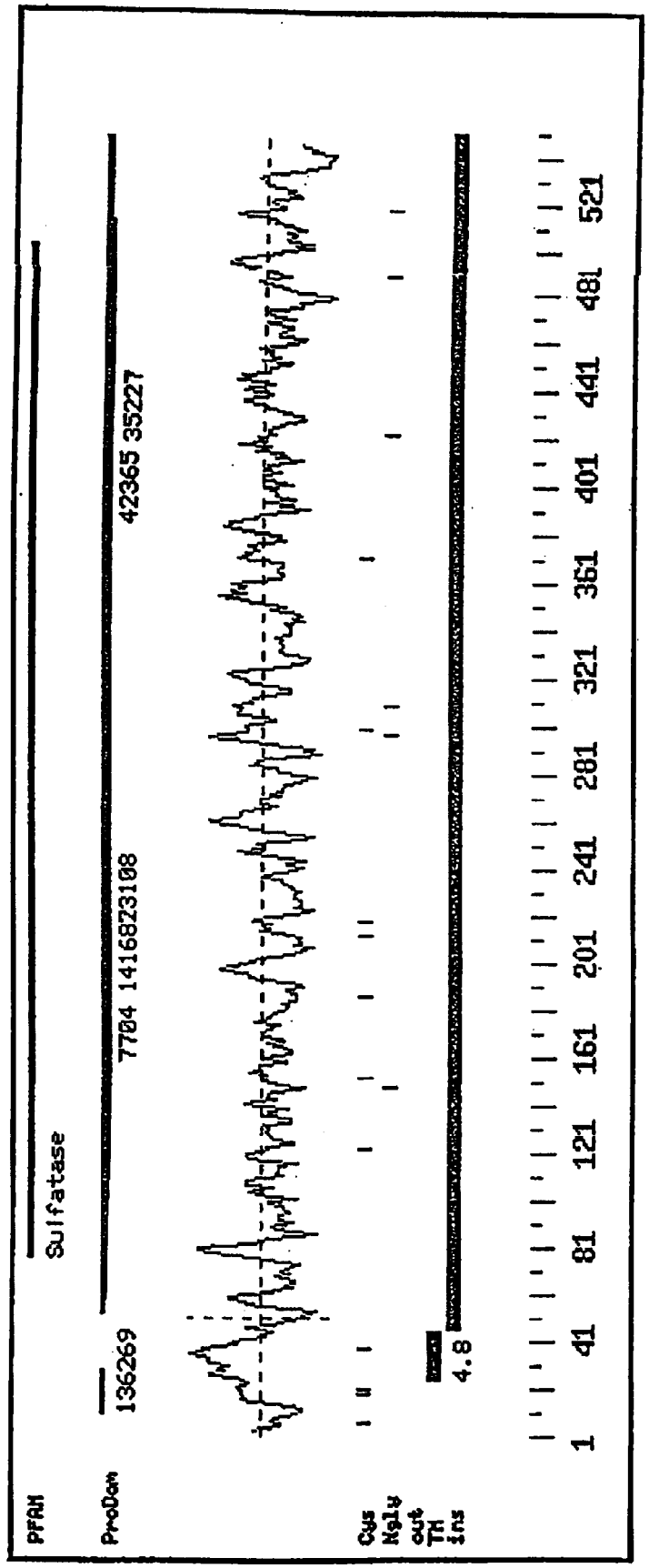
FIG. 16 shows a 26212 sulfatase hydrophobicity plot.
Figure 17:
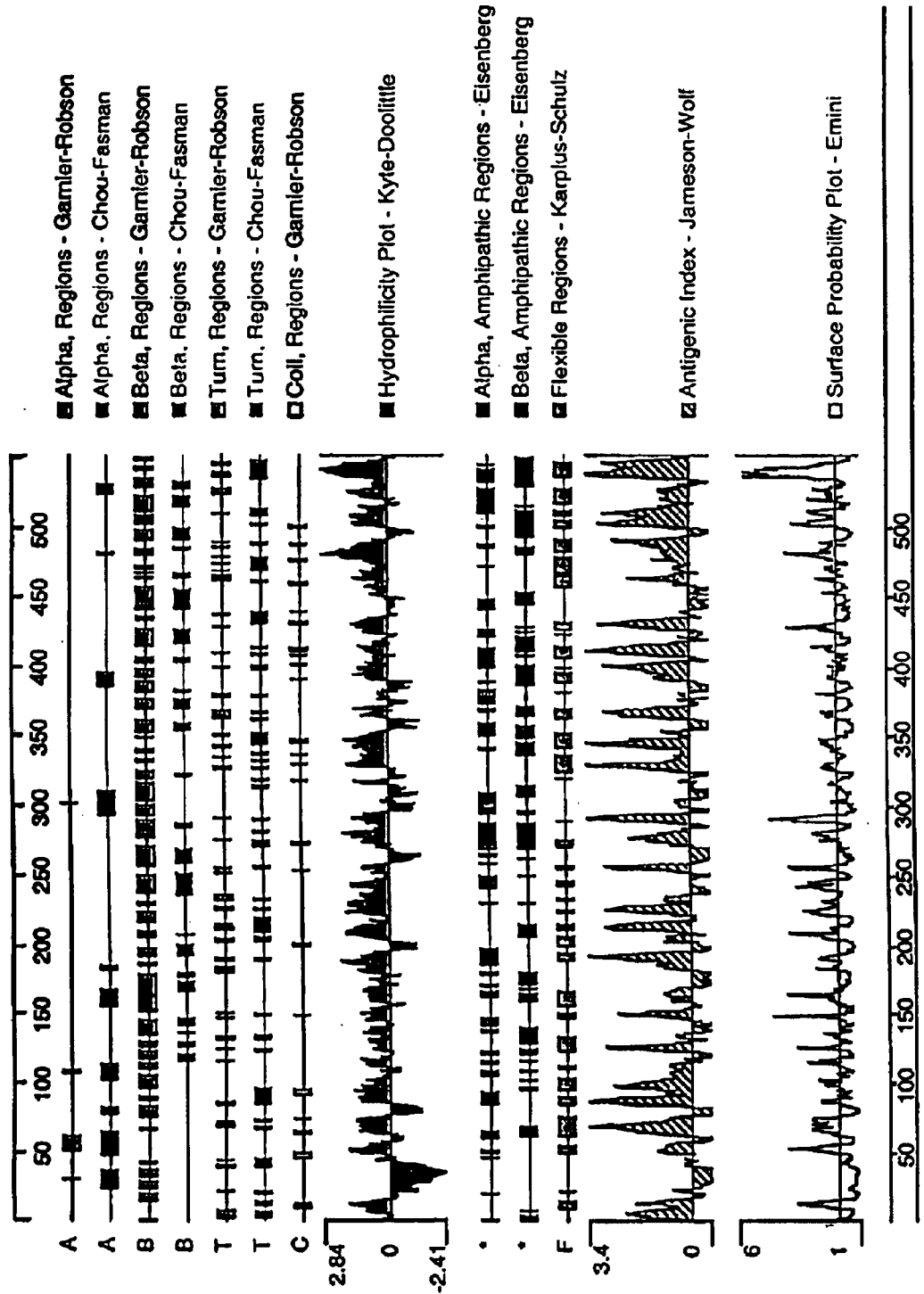
FIG. 17 shows an analysis of the 26212 sulfatase amino acid sequence: αβturn and coil regions; hydrophilicity; amphipathic regions; flexible regions; antigenic index; and surface probability plot.

The isolated 25278 sulfatase protein can be purified from cells that naturally express it, such as cells from any of the tissues shown in FIG. 14, especially purified from cells that have been altered to express it (recombinant), or synthesized using known protein synthesis methods.

The isolated 26212 sulfatase protein can be purified from cells that naturally express it, especially purified from cells that have been altered to express it (recombinant), or synthesized using known protein synthesis methods.

In one embodiment, the protein is produced by recombinant DNA techniques. For example, a nucleic acid molecule encoding the sulfatase polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enymol.* 182:626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

Sulfatase polypeptides are useful for producing antibodies specific for sulfatase, regions, or fragments. Regions having a high antigenicity index score are shown in FIGS. 3, 7, 12, and 17.

Sulfatase polypeptides are useful for biological assays related to sulfatases. Such assays involve any of the known sulfatase functions or activities or properties useful for diagnosis and treatment of sulfatase-related conditions, including those in the references cited herein, which are incorporated by reference for these assays, functions, and disorders.

These assays include, but are not limited to, binding to and/or cleaving specific substrates to produce fragments, steady state levels of sulfated compounds, cysteine modification, and biological assays related to the functions produced by sulfated compounds. Specific substrates useful for assays related to sulfate conjugate hydrolysis include but are not limited to xenobiotics, thyroid hormones, steroids, and catechols. Specific sulfate conjugates include, but are not limited to, 3α-sulfatolithocholyltaurine, sulfate conjugates of estrone, 4-methylumbelliferone, and harmol, sulfated cartilage and proteoglycans, 4-nitrophenol, simple phenols, hydroxyarylamines, iodothyronines, catecholamines, 1-naphthyl, salbutamol, estrogens, ethinylestradiol, equilenin, diethylstilbestrol, androgens, cholesterol bile salts, pregnenolone, benzylic alcohols, glycolipidsulfates, complex carbohydrates such as dermatan and chondrotin sulfate, steroid sulfate, sulfate conjugates of xenobiotics, cholesterol sulfate, xenobiotic phenyls, o-cresol, vanillan, eugenol, m-cresol, thymol, ethyl-4,4-dihydroxybenzoate, p-cresol, sesamol, methyl-2,6-dihydroxy4-methylbenzyloate, methyl-2,4-dihydroxybenzoate, methyl-3,5-dihydroxybenzoate, tyramine, dopamine, 5 hydroxytryptamine, pyrogallol, 4-nitrocatecholsulfate, estrone sulfate, metabolites of the cytochrome P450 mono-oxygenase system, dihydroepiandrosterone sulfate (DHEAS), minoxidil, cicletanine, sulfated mutagens and carcinogens, such as aromatic amines (including heterocyclic amines), and benzylic alcohols of chemicals such as polycyclic aromatic hydrocarbons, saffrole and estragole, glycosaminoglycans, sulfolipids, betahydroxysteroids, sulfate esters of chromogenic or fluorogenic aromatic compounds, cerebroside sulfate, keritan sulfate, and heparan sulfate. Substrates also include any in the references cited herein, which are incorporated herein by reference for these substrates. Accordingly the assays include, but are not limited to, these sulfated substrates and biological effects of sulfation or desulfation of these substrates and associated biochemical, cellular, or phenotypic effects of sulfation of desulfation, and any of the other biological or functional properties of these proteins, including, but not limited to, those disclosed herein, and in any reference cited herein which is incorporated herein by reference for the disclosure of these properties and for the assays based on these properties. Further, assays may relate to changes in the protein, per se, and on the effects of these changes, for example, activation of the sulfatase by modification of a cysteine residue as disclosed herein, cleavage of the propeptide by a proteinase, induction of expression of the protein in vivo, inhibition of function, as well as any other effects on the protein mentioned herein or cited in any reference herein, which are incorporated herein by reference for these effects and for the subsequent biological consequences of these effects.

Sulfatase polypeptides are also useful in drug screening assays, in cell-based or cell-free systems. Cell-based systems can be native, i.e., cells that normally express sulfatase, such as those discussed above, especially tumor cells, asia biopsy, or expanded in cell culture. In one embodiment, however, cell-based assays involve recombinant host cells expressing sulfatase. Accordingly, these drug-screening assays can be based on effects on protein function as described above for biological assays useful for diagnosis and treatment.

Determining the ability of the test compound to interact with a sulfatase can also comprise determining the ability of the test compound to preferentially bind to the polypeptide as compared to the ability of a known binding molecule to bind to the polypeptide.

The polypeptides can be used to identify compounds that modulate sulfatase activity. Such compounds, for example, can increase or decrease affinity or rate of binding to substrate, compete with substrate for binding to sulfatase, or displace substrate bound to sulfatase. Both sulfatase and appropriate variants and fragments can be used in high-throughput screens to assay candidate compounds for the ability to bind to sulfatase. These compounds can be further screened against a functional sulfatase to determine the effect of the compound on sulfatase activity. Compounds can be identified that activate (agonist) or inactivate (antagonist) sulfatase to a desired degree. Modulatory methods can be performed in vitro (e.g., by culturing the cell with the agent) or, alternatively, in vivo (e.g., by administering the agent to a subject).

Sulfatase polypeptides can be used to screen a compound for the ability to stimulate or inhibit interaction between sulfatase protein and a target molecule that normally interacts with the sulfatase, for example, substrate of the sulfatase domain. The assay includes the steps of combining sulfatase protein with a candidate compound under conditions that allow the sulfatase protein or fragment to interact with the target molecule, and to detect the formation of a complex between the sulfatase protein and the target or to detect the biochemical consequence of the interaction with the sulfatase and the target.

Determining the ability of the sulfatase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad Sci. USA* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc. Natl. Acad Sci. USA* 89:1865–1869) or on phage (Scott and Smith (1990) *Science* 249:386–390); (Devlin (1990) *Science* 249:404–406); (Cwirla et al. (1990) *Proc. Natl. Acad Sci.* 97:6378–6382); (Felici (1991) *J. Mol. Biol.* 222:301–310), (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778), 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); substrate analogs including, but not limited to, substrates disclosed herein.

One candidate compound is a soluble full-length sulfatase or fragment that competes for substrate. Other candidate compounds include mutant sulfatases or appropriate fragments containing mutations that affect sulfatase function and compete for substrate. Accordingly, a fragment that competes for substrate, for example with a higher affinity, or a fragment that binds substrate but does not process or otherwise affect it, is encompassed by the invention.

The invention provides other end points to identify compounds that modulate (stimulate or inhibit) sulfatase activity. The assays typically involve an assay of cellular events that indicate sulfatase activity. Thus, the expression of genes that are up- or down-regulated in response to sulfatase activity can be assayed. In one embodiment, the regulatory region of such genes can be operably linked to a marker that is easily detectable, such as luciferase. Alternatively, modification of the sulfatase could also be measured.

Any of the biological or biochemical functions mediated by the sulfatase can be used as an endpoint assay. These include any of the biochemical or biochemical/biological events described herein, in any reference cited herein, incorporated by reference for these endpoint assay targets, and other functions known to those of ordinary skill in the art. Specific end points can include, but are not limited to, the events resulting from expression (or lack thereof) of sulfatase activity. With respect to disorders, this would include, but not be limited to, effects on function, differentiation, and proliferation, which can be assayed, as well as the biological effects of function, such as disorders discussed hereinabove and in the references cited hereinabove which are incorporated herein by reference for the disorders disclosed in those references and other disorders and pathology. In the case of the 22438 sulfatase, models of pain can be used as an end point. In the case of the 23553 and 25278 sulfatases, tumor progression can be used as an end point.

Binding and/or activating compounds can also be screened by using chimeric sulfatase proteins in which one or more regions, segments, sites, and the like, as disclosed herein, or parts thereof, can be replaced by heterologous and homologous counterparts derived from other sulfatases. For example, a catalytic region can be used that interacts with a different substrate specificity and/or affinity than the native sulfatase. Accordingly, a different set of components is available as an end-point assay for activation. As a further alternative, the site of modification by an effector protein, for example, activation or phosphorylation, can be replaced with the site for a different effector protein. Activation can also be detected by a reporter gene containing an easily detectable coding region operably linked to a transcriptional regulatory sequence that is part of the native pathway in which sulfatase is involved.

Sulfatase polypeptides are also useful in competition binding assays in methods designed to discover compounds that interact with the sulfatase. Thus, a compound is exposed to a sulfatase polypeptide under conditions that allow the compound to bind or to otherwise interact with the polypeptide. Soluble sulfatase polypeptide is also added to the mixture. If the test compound interacts with the soluble sulfatase polypeptide, it decreases the amount of complex formed or activity from the sulfatase target. This type of assay is particularly useful in cases in which compounds are sought that interact with specific regions of the sulfatase. Thus, the soluble polypeptide that competes with the target sulfatase region is designed to contain peptide sequences corresponding to the region of interest.

Another type of competition-binding assay can be used to discover compounds that interact with specific functional sites. As an example, bindable substrate analog and a candidate compound can be added to a sample of the sulfatase. Compounds that interact with the sulfatase at the same site as the substrate or analog will reduce the amount of complex formed between the sulfatase and the substrate or analog. Accordingly, it is possible to discover a compound that specifically prevents interaction between the sulfatase and the component. Another example involves adding a candidate compound to a sample of sulfatase and cleavable substrate. A compound that competes with the substrate will reduce the amount of hydrolysis or binding of the substrate to the sulfatase. Accordingly, compounds can be discovered that directly interact with the sulfatase and compete with the substrate. Such assays can involve any other component that interacts with the sulfatase.

To perform cell free drug screening assays, it is desirable to immobilize either sulfatase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/sulfatase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of sulfatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a sulfatase-binding target component, such as substrate or activating enzyme, and a candidate compound are incubated in sulfatase-presenting wells and the amount of complex trapped in the well can be quantitated. Methods for detecting such complexes, in addition to those described above for the GST-immobilized complexes, include immunodetection of complexes using antibodies reactive with the sulfatase target molecule, or which are reactive with the sulfatase and compete with the target molecule; as well as enzyme-linked assays which rely on detecting an enzymatic activity associated with the target molecule.

Modulators of sulfatase activity identified according to these drug screening assays can be used to treat a subject with a disorder related to the sulfatase, by treating cells that express the sulfatase. These methods of treatment include the steps of administering the modulators of sulfatase activity in a pharmaceutical composition as described herein, to a subject in need of such treatment.

The 23553 and 25278 sulfatases are differentially expressed in tumor cells as disclosed herein. Accordingly, these sulfatases are relevant to these disorders and relevant as well to differentiation, function, and growth of the tissues giving rise to the tumors. The 22438 sulfatase is expressed as described above, and accordingly is relevant for disorders involving these tissues. Disorders include, but are not limited to, those discussed hereinabove. Moreover, since the gene is expressed in the central nervous system, this sulfatase is relevant for the treatment of pain.

Sulfatase polypeptides are thus useful for treating a sulfatase-associated disorder characterized by aberrant expression or activity of a sulfatase. In one embodiment, the method involves administering an agent (e.g., an agent identified by a screening assay described herein), or combination of agents that modulates (e.g., upregulates or downregulates) expression or activity of the protein. In another embodiment, the method involves administering sulfatase as therapy to compensate for reduced or aberrant expression or activity of the protein.

Methods for treatment include but are not limited to the use of soluble sulfatase or fragments of sulfatase protein that compete for substrate or any other component that directly interacts with sulfatase, or any of the enzymes that modify the sulfatase. These sulfatases or fragments can have a higher affinity for the target so as to provide effective competition Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a disorder characterized by an aberrant hematopoietic response. In another example, it is desirable to achieve tissue regeneration in a subject.

In yet another aspect of the invention, the proteins of the invention can be used as "bait proteins" in a two-hybrid assay or three-hybrid assay (see, e.g., U.S. Pat. No. 5,283, 317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO 94/10300), to identify other proteins (captured proteins) which bind to or interact with the proteins of the invention and modulate their activity.

Sulfatase polypeptides also are useful to provide a target for diagnosing a disease or predisposition to disease mediated by the sulfatase, including, but not limited to, those diseases disclosed herein, in the references cited herein, and as disclosed above in the background. Accordingly, methods are provided for detecting the presence, or levels of the sulfatase in a cell, tissue, or organism. The method involves contacting a biological sample with a compound capable of interacting with the sulfatase such that the interaction can be detected. One agent for detecting a sulfatase is an antibody capable of selectively binding to the sulfatase. A biological sample includes tissues, cells and biological fluids isolated from a subject, as well as tissues, cells and fluids present within a subject.

The sulfatase also provides a target for diagnosing active disease, or predisposition to disease, in a patient having a variant sulfatase. Thus, sulfatase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered sulfatase activity in cell-based or cell-free assays, such as by alteration in substrate binding or degradation, or ability to be activated by the activation enzyme, or antibody-binding pattern, altered isoelectric point, direct amino acid sequencing, and any other of the known assay techniques useful for detecting mutations in a protein in general or in a sulfatase specifically, such as are disclosed herein.

In vitro techniques for detection of sulfatase include enzyme linked immunosorbent assays (ELISAs), Western blots, immunoprecipitations and immunofluorescence. Alternatively, the protein can be detected in vivo in a subject by introducing into the subject a labeled anti-sulfatase antibody. For example, the antibody can be labeled with a radioactive marker whose presence and location in a subject can be detected by standard imaging techniques. Particularly useful are methods, which detect the allelic variant of sulfatase expressed in a subject, and methods, which detect fragments of sulfatase in a sample.

Sulfatase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10–11):983–985, and Linder, M. W. (1997) Clin. Chem. 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of sulfatase in which one or more of sulfatase functions in one population is different from those in another population. The polypeptides thus allow a target to ascertain a genetic predisposition that can affect treatment modality. Thus, in a peptide-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

Sulfatase polypeptides are also useful for monitoring therapeutic effects during clinical trials and other treatment. Thus, the therapeutic effectiveness of an agent that is designed to increase or decrease gene expression, protein levels or sulfatase activity can be monitored over the course of treatment using sulfatase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the sulfatase and its variants and fragments. An antibody is considered to selectively bind, even if it also binds to other proteins that are not substantially homologous with the sulfatase. These other proteins share homology with a fragment or domain of sulfatase. This conservation in specific regions gives rise to antibodies that bind to both proteins by virtue of the homologous sequence. In this case, it would be understood that antibody binding to the sulfatase is still selective.

Antibodies can be polyclonal or monoclonal. An intact antibody, or a fragment thereof (e.g. Fab or F(ab')$_2$) can be used. An appropriate immunogenic preparation can be derived from native, recombinantly expressed, or chemically synthesized peptides.

To generate antibodies, an isolated sulfatase polypeptide is used as an immunogen to generate antibodies using standard techniques for polyclonal and monoclonal antibody preparation. Either the full-length protein or antigenic peptide fragment can be used. Regions having a high antigenicity index are disclosed hereinabove.

Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire sulfatase or domains of the sulfatase as described herein, for example, the substrate binding region, sulfatase motif, or subregions thereof Antibodies can also be developed against other specific functional sites as disclosed herein.

The antigenic peptide can comprise a contiguous sequence of at least 12, 14, 15–20, 20–25, or 25–30 or more amino acid residues. In one embodiment, fragments correspond to regions that are located on the surface of the protein, e.g., hydrophilic regions. These fragments are not to be construed, however, as encompassing any fragments, which may be disclosed prior to the invention.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I $^{35}$S or $^{3}$H Antibody Uses The antibodies can be used to isolate a sulfatase by standard techniques, such as affinity chromatography or immunoprecipitation. The antibodies can facilitate the purification of the natural sulfatase from cells and recombinantly produced sulfatase expressed in host cells.

The antibodies are useful to detect the presence of a sulfatase in cells or tissues to determine the pattern of expression of the sulfatase among various tissues in an organism and over the course of normal development. The antibodies can be used to detect a sulfatase in situ, in vitro, or in a cell lysate or supernatant in order to evaluate the abundance and pattern of expression. Antibody detection of circulating fragments of the full length sulfatase can be used to identify sulfatase turnover. In addition, the antibodies can be used to assess abnormal tissue distribution or abnormal expression during development.

Further, the antibodies can be used to assess sulfatase expression in disease states such as in active stages of the disease or in an individual with a predisposition toward disease related to sulfatase function. When a disorder is caused by an inappropriate tissue distribution, developmental expression, or level of expression of sulfatase protein, the antibody can be prepared against the normal sulfatase protein. If a disorder is characterized by a specific mutation in sulfatase, antibodies specific for this mutant protein can be used to assay for the presence of the specific mutant sulfatase. However, intracellularly-made antibodies ("intrabodies") are also encompassed, which would recognize intracellular sulfatase peptide regions.

The antibodies can also be used to assess normal and aberrant subcellular localization of cells in the various tissues in an organism. Antibodies can be developed against the whole sulfatase or portions of the sulfatase.

The diagnostic uses can be applied, not only in genetic testing, but also in monitoring a treatment modality. Accordingly, where treatment is ultimately aimed at correcting sulfatase expression level or the presence of aberrant sulfatases and aberrant tissue distribution or developmental expression, antibodies directed against the sulfatase or relevant fragments can be used to monitor therapeutic efficacy.

Additionally, antibodies are useful in pharmacogenomic analysis. Thus, antibodies prepared against polymorphic sulfatase can be used to identify individuals that require modified treatment modalities.

The antibodies are also useful as diagnostic tools as an immunological marker for aberrant sulfatase analyzed by electrophoretic mobility, isoelectric point, tryptic peptide digest, and other physical assays known to those in the art.

The antibodies are also useful for tissue typing. Thus, where a specific sulfatase has been correlated with expression in a specific tissue, antibodies that are specific for this sulfatase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting sulfatase function, for example, substrate binding, or sulfatase activity. For example, sulfatase activity may be measured by the ability to form a binding complex with a sulfated conjugate, such as disclosed herein.

These uses can also be applied in a therapeutic context in which treatment involves inhibiting sulfatase function. An antibody can be used, for example, to block substrate binding. Antibodies can be prepared against specific fragments containing sites required for function or against intact sulfatase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016, and U.S. Pat. No. 5,545,806.

The invention also encompasses kits for using antibodies to detect the presence of a sulfatase protein in a biological sample. The kit can comprise antibodies such as a labeled or labelable antibody and a compound or agent for detecting the sulfatase in a biological sample; means for determining the amount of sulfatase in the sample; and means for comparing the amount of sulfatase in the sample with a standard. The compound or agent can be packaged in a suitable container. The kit can further comprise instructions for using the kit to detect the sulfatase.

Polynucleotides

The nucleotide sequences in SEQ ID NOS:2, 4, 6, and 8 were obtained by sequencing the deposited human cDNAs. Accordingly, the sequences of the deposited clones are controlling as to any discrepancies between the two and any reference to a sequence of SEQ ID NOS:2, 4, 6, or 8, includes reference to the sequence of the deposited cDNA.

The specifically disclosed cDNA comprises the coding region and 5' and 3' untranslated sequences in SEQ ID NOS:2, 4, 6, or 8.

The invention provides isolated polynucleotides encoding the novel sulfatases. The term "sulfatase polynucleotide" or "sulfatase nucleic acid" refers to the sequences shown in SEQ ID NOS:2, 4, 6, or 8, or in the deposited cDNAs. The term "sulfatase polynucleotide" or "sulfatase nucleic acid" further includes variants and fragments of sulfatase polynucleotides.

An "isolated" sulfatase nucleic acid is one that is separated from other nucleic acid present in the natural source of sulfatase nucleic acid. Preferably, an "isolated" nucleic acid is free of sequences which naturally flank sulfatase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the sulfatase nucleic acid is isolated from flanking sequences such that it can be subjected to the specific manipulations described herein, such as recombinant expression, preparation of probes and primers, and other uses specific to the sulfatase nucleic acid sequences. In one embodiment, the sulfatase nucleic acid comprises only the coding region.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

Sulfatase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

Sulfatase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Sulfatase polynucleotides can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (antisense strand).

The invention further provides variant sulfatase polynucleotides, and fragments thereof, that differ from the nucleotide sequence shown in SEQ ID NOS:2, 4, 6, or 8, due to degeneracy of the genetic code and thus encode the same protein as that encoded by a nucleotide sequence shown in SEQ ID NOS:2, 4, 6, or 8.

The invention also provides sulfatase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NOS:2, 4, 6 or 8, and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a sulfatase that is typically at least about 40–45%, 45–50%, 50–55%, 55–60%, 60–65%, 65–70%, 70–75%, more typically at least about 75–80% or 80–85%, and most typically at least about 85–90% or 90–95% or more homologous to the nucleotide sequence shown in SEQ ID NOS:2, 4, 6 or 8, or a fragment of this sequence. Such nucleic acid molecules can readily be identified as being able to hybridize under stringent conditions, to the nucleotide sequence shown in SEQ ID NOS:2, 4, 6 or 8, or a fragment of the sequence.

In the case of the 23553 sulfatase, in one embodiment, a variant is greater than 65% homologous with respect to nucleotide sequence. For the 25278 sulfatase, in one embodiment, a variant is greater than 50–60% homologous with respect to nucleotide sequence. With respect to the 26212 sulfatase, in one embodiment, a variant is greater than about 65–75% homologous with respect to nucleotide sequence.

It is understood that stringent hybridization does not indicate substantial homology where it is due to general homology, such as polyA$^+$ sequences, or sequences common to all or most proteins, sulfatases, arylsulfatases, glucosamine-6-sulfatases, N-acetylgalactosamine-4-sulfatases, or any of the sulfatases to which the sulfatases of the present invention have shown homology by BLAST analysis, for example, regions to arylsulfatases A, B, C, D, E, F, IDS, and the like. Moreover, it is understood that variants do not include any of the nucleic acid sequences that may have been disclosed prior to the invention.

As used herein, the term "stringent conditions" is intended to describe conditions comprising hybridization in 6×sodium chloride/sodium citrate (SSC) at about 45° C., followed by one or more washes in 0.2×SSC/0.1% SDS at 65° C. Methods of hybridization are known to those skilled in the art and can be found in *Current Protocols in Molecular Biology*, John Wiley & Sons, N.Y. (1998), incorporated by reference. In one embodiment, an isolated nucleic acid molecule that hybridizes under stringent conditions to a sequence of SEQ ID NOS:2, 4, 6 or 8, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

The present invention also provides isolated nucleic acids that contain a single or double stranded fragment or portion that hybridizes under stringent conditions to the nucleotide sequence of SEQ ID NOS:2, 4, 6, or 8 or the complements of SEQ ID NOS:2, 4, 6, or 8. In one embodiment, the nucleic acid consists of a portion of a nucleotide sequence of SEQ ID NOS:2, 4, 6 or 8, and the complements. The nucleic acid fragments of the invention are at least about 10–15, preferably at least about 15–20 or 20–25 contiguous nucleotides, and can be 30, 33, 35, 40, 50, 60, 70, 75, 80, 90, 100, 200, 500 or more nucleotides in length. Longer fragments, for example, 600 or more nucleotides in length, which encode antigenic proteins or polypeptides described herein are also useful.

In the case of the 23553 sulfatase, in one embodiment, fragments are derived from nucleotide 1 to about nucleotide 670 and comprise 5–10 and 10–20 contiguous base pairs, and particularly greater than 18. For this sulfatase, in another embodiment, a fragment is derived from around nucleotide 3008 to 3514 and comprises around 5–10 and 10–20 contiguous nucleotides. In other embodiments for this sulfatase, a fragment is derived from around nucleotide 3994 to 4321 and is about 5–10 or 10–20 contiguous nucleotides. For the 25278, in one embodiment, a fragment is derived from around nucleotide 130 to around nucleotide 454 and comprises a contiguous sequence of about 5–10 or 10–20 nucleotides. In another embodiment, the fragment is derived from around nucleotide 454 to around nucleotide 1400 and comprises around 5–10 or 10–20 contiguous nucleotides, especially a fragment greater than 17 nucleotides. In another embodiment the fragment is derived from around nucleotide 1400 to around nucleotide 1850 and comprises a continuous sequence of around 5–10, 10–20, or 20–25 nucleotides, especially a fragment greater than 23 nucleotides. In another embodiment, a fragment is derived from about nucleotide 1933 to about nucleotide 2421. Such a fragment comprises around 5–10 or 10–20 contiguous nucleotides. For the 26212 sulfatase, in one embodiment, a fragment is derived from around nucleotide 272 to around nucleotide 538 and comprises a contiguous sequence of around 5–10 or 10–20 nucleotides, especially a fragment greater than 17 nucleotides. In another embodiment, the fragment is derived from around nucleotide 538 to around nucleotide 751 and comprises a contiguous sequence of at least 5–10 or 10–20 nucleotides, especially greater than 12 nucleotides. In another embodiment, the fragment is derived from around nucleotide 1074 to around 1551 and comprises a contiguous nucleotide sequence of around 5–10, 10–20, or 20–30, especially greater than 20 nucleotides. In a further embodiment, the fragment is derived from around nucleotide 2052 to 2251 and comprises a contiguous sequence of 5–10 and 10–20 nucleotides, especially fragments greater than 18 nucleotides.

The fragment can comprise DNA or RNA and can be derived from either the coding or the non-coding sequence.

In another embodiment an isolated sulfatase nucleic acid encodes the entire coding region. In another embodiment the isolated sulfatase nucleic acid encodes a sequence corresponding to the mature protein. Other fragments include nucleotide sequences encoding the amino acid fragments described herein.

Thus, sulfatase nucleic acid fragments further include sequences corresponding to the regions described herein, subregions also described, and specific functional sites. Sulfatase nucleic acid fragments also include combinations of the regions, segments, motifs, and other functional sites described above. It is understood that a sulfatase fragment includes any nucleic acid sequence that does not include the entire gene. A person of ordinary skill in the art would be aware of the many permutations that are possible. Nucleic acid fragments, according to the present invention, are not to be construed as encompassing those fragments that may have been disclosed prior to the invention.

Where the location of the regions or sites have been predicted by computer analysis, one of ordinary skill would appreciate that the amino acid residues constituting these regions can vary depending on the criteria used to define the regions.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 30, 40, 50 or 75 consecutive nucleotides of the nucleic acid sequence shown in SEQ ID NO:2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

Sulfatase polynucleotides are thus useful for probes, primers, and in biological assays. Where the polynucleotides are used to assess sulfatase properties or functions, such as in the assays described herein, all or less than all of the entire cDNA can be useful. Assays specifically directed to sulfatase functions, such as assessing agonist or antagonist activity, encompass the use of known fragments. Further, diagnostic methods for assessing sulfatase function can also be practiced with any fragment, including those fragments that may have been known prior to the invention. Similarly, in methods involving treatment of sulfatase dysfunction, all fragments are encompassed including those, which may have been known in the art.

Sulfatase polynucleotides are useful as a hybridization probe for cDNA and genomic DNA to isolate a full-length cDNA and genomic clones encoding the polypeptides described in SEQ ID NOS:1, 3, 5, or 7, and to isolate cDNA and genomic clones that correspond to variants producing the same polypeptides shown in SEQ ID NOS:1, 3, 5, or 7, or the other variants described herein. Variants can be isolated from the same tissue and organism from which a polypeptide shown in SEQ ID NOS:1, 3, 5, or 7 was isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the sulfatase polypeptide. Accordingly, it could be derived from 5' noncoding regions, the coding region, and 3' noncoding regions.

The nucleic acid probe can be, for example, the full-length cDNA of SEQ ID NOS:2, 4, 6, or 8, or a fragment thereof such as an oligonucleotide of at least 5, 10, 15, 20, 25, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein, ribozymes or antisense molecules. For example, a fragment can be hybridized to any portion of an mRNA and a larger or full-length cDNA can be produced.

Antisense nucleic acids of the invention can be designed using the nucleotide sequences of SEQ ID NOS:2, 4, 6, or 8, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry- O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell sulfatases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci: USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1 988) *Pharm Res.* 5:539–549).

Sulfatase polynucleotides are also useful as primers for PCR to amplify any given region of a sulfatase polynucleotide.

Sulfatase polynucleotides are also useful for constructing recombinant vectors. Such vectors include expression vectors that express a portion of, or all of, the sulfatase polypeptides. Vectors also include insertion vectors, used to integrate into another polynucleotide sequence, such as into the cellular genome, to alter in situ expression of sulfatase genes and gene products. For example, an endogenous sulfatase coding sequence can be replaced via homologous recombination with all or part of the coding region containing one or more specifically introduced mutations.

Sulfatase polynucleotides are also useful for expressing antigenic portions of sulfatase proteins.

Sulfatase polynucleotides are also useful as probes for determining the chromosomal positions of sulfatase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to-be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

Sulfatase polynucleotide probes are also useful to determine patterns of the presence of the gene encoding sulfatases and their variants with respect to tissue distribution, for example, whether gene duplication has occurred and whether the duplication occurs in all or only a subset of tissues. The genes can be naturally occurring or can have been introduced into a cell, tissue, or organism exogenously.

Sulfatase polynucleotides are also useful for designing ribozymes corresponding to all, or a part, of the mRNA produced from genes encoding the polynucleotides described herein.

Sulfatase polynucleotides are also useful for constructing host cells expressing a part, or all, of a sulfatase polynucleotide or polypeptide.

Sulfatase polynucleotides are also useful for constructing transgenic animals expressing all, or a part, of a sulfatase polynucleotide or polypeptide.

Sulfatase polynucleotides are also useful for making vectors that express part, or all, of a sulfatase polypeptide.

Sulfatase polynucleotides are also useful as hybridization probes for determining the level of sulfatase nucleic acid expression. Accordingly, the probes can be used to detect the presence of, or to determine levels of, sulfatase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of a sulfatase gene.

Alternatively, the probe can be used in an in situ hybridization context to assess the position of extra copies of a sulfatase gene, as on extrachromosomal elements or as integrated into chromosomes in which the sulfatase gene is not normally found, for example, as a homogeneously staining region.

These uses are relevant for diagnosis of disorders involving an increase or decrease in sulfatase expression relative to normal, such as a proliferative disorder, a differentiative or developmental disorder, or a hematopoietic disorder. Disorders in which sulfatase expression is relevant include, but are not limited to, those disclosed herein above.

Disorders in which 22438 sulfatase expression is relevant include, but are not limited to, those involving the tissues as disclosed herein and those associated with pain.

Disorders in which 23553 sulfatase expression is relevant include, but are not limited to, breast and colon carcinoma.

Disorders in which 25278 sulfatase expression is relevant include, but are not limited to, colon carcinoma.

Thus, the present invention provides a method for identifying a disease or disorder associated with aberrant expression or activity of a sulfatase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a sulfatase, such as by measuring the level of a sulfatase-encoding nucleic acid in a sample of cells from a subject e.g., mRNA or genomic DNA, or determining if the sulfatase gene has been mutated.

Nucleic acid expression assays are useful for drug screening to identify compounds that modulate sulfatase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals. The invention thus provides a method for identifying a compound that can be used to treat a disorder associated with nucleic acid expression of a sulfatase gene. The method typically includes assaying the ability of the compound to modulate the expression of the sulfatase nucleic acid and thus identifying a compound that can be used to treat a disorder characterized by undesired sulfatase nucleic acid expression.

The assays can be performed in cell-based and cell-free systems. Cell-based assays include cells naturally expressing the sulfatase nucleic acid or recombinant cells genetically engineered to express specific nucleic acid sequences. Alternatively, candidate compounds can be assayed in vivo in patients or in transgenic animals.

The assay for sulfatase nucleic acid expression can involve direct assay of nucleic acid levels, such as mRNA levels, or on collateral compounds (such as substrate hydrolysis). Further, the expression of genes that are up- or down-regulated in response to sulfatase activity can also be assayed. In this embodiment the regulatory regions of these genes can be operably linked to a reporter gene such as luciferase.

Thus, modulators of sulfatase gene expression can be identified in a method wherein a cell is contacted with a candidate compound and the expression of mRNA determined. The level of expression of sulfatase mRNA in the presence of the candidate compound is compared to the level of expression of sulfatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate sulfatase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Alternatively, a modulator for sulfatase nucleic acid expression can be a small molecule or drug identified using the screening assays described herein as long as the drug or small molecule inhibits sulfatase nucleic acid expression.

Sulfatase polynucleotides are also useful for monitoring the effectiveness of modulating compounds on the expression or activity of a sulfatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a-physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

Sulfatase polynucleotides are also useful in diagnostic assays for qualitative changes in sulfatase nucleic acid, and particularly in qualitative changes that lead to pathology. The polynucleotides can be used to detect mutations in sulfatase genes and gene expression products such as mRNA. The polynucleotides can be used as hybridization probes to detect naturally-occurring genetic mutations in a sulfatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of a sulfatase gene associated with a dysfunction provides a diagnostic tool for an active disease or susceptibility to disease when the disease results from overexpression, underexpression, or altered expression of a sulfatase.

Mutations in a sulfatase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a sulfatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant sulfatase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat Res.* 285: 125–144; and Hayashi et la. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

Sulfatase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the sulfatase gene that results in altered affinity for a substrate-related compound could result in an excessive or decreased drug effect with standard concentrations of the compound. Accordingly, the sulfatase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

Sulfatase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Sulfatase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the sulfatase sequences can be used to provide an alternative technique, which determines the actual DNA sequence of selected fragments in the genome of an individual. Thus, the sulfatase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. Sulfatase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

Sulfatase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

Sulfatase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

Sulfatase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of sulfatase probes can be used to identify tissue by species and/or by organ type.

In a similar fashion, these primers and probes can be used to screen tissue culture for contamination (i.e. screen for the presence of a mixture of different types of cells in a culture).

Alternatively, sulfatase polynucleotides can be used directly to block transcription or translation of sulfatase gene sequences by means of antisense or ribozyme constructs. Thus, in a disorder characterized by abnormally high or undesirable sulfatase gene expression, nucleic acids can be directly used for treatment.

Sulfatase polynucleotides are thus useful as antisense constructs to control sulfatase gene expression in cells, tissues, and organisms. A DNA antisense polynucleotide is designed to be complementary to a region of the gene involved in transcription, preventing transcription and hence production of sulfatase protein. An antisense RNA or DNA polynucleotide would hybridize to the mRNA and thus block translation of mRNA into sulfatase protein.

Examples of antisense molecules useful to inhibit nucleic acid expression include antisense molecules complementary to a fragment of the 5' untranslated region of SEQ ID NOS:2, 4, 6, or 8, which also includes the start codon and antisense molecules which are complementary to a fragment of the 3' untranslated region of SEQ ID NOS:2, 4, 6, or 8.

Alternatively, a class of antisense molecules can be used to inactivate mRNA in order to decrease expression of sulfatase nucleic acid. Accordingly, these molecules can treat a disorder characterized by abnormal or undesired sulfatase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the sulfatase protein.

Sulfatase polynucleotides also provide vectors for gene therapy in patients containing cells that are aberrant in sulfatase gene expression. Thus, recombinant cells, which include the patient's cells that have been engineered ex vivo and returned to the patient, are introduced into an individual where the cells produce the desired sulfatase protein to treat the individual.

The invention also encompasses kits for detecting the presence of a sulfatase nucleic acid in a biological sample. For example, the kit can comprise reagents such as a labeled or labelable nucleic acid or agent capable of detecting sulfatase nucleic acid in a biological sample; means for determining the amount of sulfatase nucleic acid in the sample; and means for comparing the amount of sulfatase nucleic acid in the sample with a standard. The compound or agent can be packaged in a suitable container. The kit can further comprise instructions for using the kit to detect sulfatase mRNA or DNA.

Computer Readable Means

The nucleotide or amino acid sequences of the invention are also provided in a variety of mediums to facilitate use thereof As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape, optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:4034 10) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing sulfatase polynucleotides. The term "vector" refers to a vehicle, preferably a nucleic acid molecule that can transport sulfatase polynucleotides. When the vector is a nucleic acid molecule, the sulfatase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of sulfatase polynucleotides. Alternatively, the vector may integrate into the host cell genome and produce additional copies of sulfatase polynucleotides when the host cell replicates.

The invention provides vectors for the maintenance (cloning vectors) or vectors for expression (expression vectors) of sulfatase polynucleotides. The vectors can function in procaryotic or eukaryotic cells or in both (shuttle vectors).

Expression vectors contain cis-acting regulatory regions that are operably linked in the vector to sulfatase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of sulfatase polynucleotides from the vector. Alternatively, a trans-acting factor may be supplied by the host cell. Finally, a trans-acting factor can be produced from the vector itself.

It is understood, however, that in some embodiments, transcription and/or translation of sulfatase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd ed., Cold Spring Harbor Laboratory Press, Cold Spring Harbor, N.Y.).

A variety of expression vectors can be used to express a sulfatase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual* 2nd ed, Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

Sulfatase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of sulfatase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

Sulfatase polynucleotides can also be expressed by expression vectors that are operative in yeast. Examples of vectors for expression in yeast e.g., *S. cerevisiae* include pYepSec1 (Baldari et al. (1987) *EMBO J*. 6:229–234 ), pMFa (Kurjan et al. (1982) *Cell* 30:933–943), pJRY88 (Schultz et al. (1987) *Gene* 54:113–123), and pYES2 (Invitrogen Corporation, San Diego, Calif.).

Sulfatase polynucleotides can also be expressed in insect cells using, for example, baculovirus expression vectors. Baculovirus vectors available for expression of proteins in cultured insect cells (e.g., Sf 9 cells) include the pAc series (Smith et al. (1983)*Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J*. 6:187–195).

The expression vectors listed herein are provided by way of example only of the well-known vectors available to those of ordinary skill in the art that would be useful to express sulfatase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.)

Host cells can contain more than one vector. Thus, different nucleotide sequences can be introduced on different vectors of the same cell. Similarly, sulfatase polynucleotides can be introduced either alone or with other polynucleotides that are not related to sulfatase polynucleotides such as those providing trans-acting factors for expression vectors. When more than one vector is introduced into a cell, the vectors can be introduced independently, co-introduced or joined to the sulfatase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the sulfatase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing sulfatase proteins or polypeptides that can be further purified to produce desired amounts of sulfatase protein or fragments. Thus, host cells containing expression vectors are useful for polypeptide production.

Host cells are also useful for conducting cell-based assays involving sulfatase or sulfatase fragments. Thus, a recombinant host cell expressing a native sulfatase is useful to assay for compounds that stimulate or inhibit sulfatase function, gene expression at the level of transcription or translation, and interaction with other cellular components.

Host cells are also useful for identifying sulfatase mutants in which these functions are affected. If the mutants naturally occur and give rise to a pathology, host cells containing the mutations are useful to assay compounds that have a desired effect on the mutant sulfatase (for example, stimulating or inhibiting function) which may not be indicated by their effect on the native sulfatase.

Recombinant host cells are also useful for expressing the chimeric polypeptides described herein to assess compounds that activate or suppress activation by means of a heterologous domain, segment, site, and the like, as disclosed herein.

Further, mutant sulfatases can be designed in which one or more of the various functions is engineered to be increased or decreased and used to augment or replace sulfatase proteins in an individual. Thus, host cells can provide a therapeutic benefit by replacing an aberrant sulfatase or providing an aberrant sulfatase that provides a therapeutic result. In one embodiment, the cells provide sulfatases that are abnormally active.

In another embodiment, the cells provide sulfatases that are abnormally inactive. These sulfatases can compete with endogenous sulfatases in the individual.

In another embodiment, cells expressing sulfatases that cannot be activated, are introduced into an individual in order to compete with endogenous sulfatases for substrate. For example, in the case in which excessive substrate or substrate analog is part of a treatment modality, it may be necessary to effectively inactivate the substrate or substrate analog at a specific point in treatment. Providing cells that compete for the molecule, but which cannot be affected by sulfatase activation would be beneficial.

Homologously recombinant host cells can also be produced that allow the in situ alteration of endogenous sulfatase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the sulfatase polynucleotides or sequences proximal or distal to a sulfatase gene are allowed to integrate into a host cell genome by homologous recombination where expression of the gene can be affected. In one embodiment, regulatory sequences are introduced that either increase or decrease expression of an endogenous sequence. Accordingly, a sulfatase protein can be produced in a cell not normally producing it. Alternatively, increased expression of sulfatase protein can be effected in a cell normally producing the protein at a specific level. Further, expression can be decreased or eliminated by introducing a specific regulatory sequence. The regulatory sequence can be heterologous to the sulfatase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant sulfatase proteins. Such mutations could be introduced, for example, into the specific functional regions such as the peptide substrate-binding site.

In one embodiment, the host cell can be a fertilized oocyte or embryonic stem cell that can be used to produce a transgenic animal containing the altered sulfatase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous sulfatase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinions in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a sulfatase protein and identifying and evaluating modulators of sulfatase protein activity.

Other examples of transgenic animals include non-human primates, sheep, dogs, cows, goats, chickens, and amphibians.

In one embodiment, a host cell is a fertilized oocyte or an embryonic stem cell into which sulfatase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the sulfatase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the sulfatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Laaso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding or activation, may not be evident from in vitro cell-free or cell-based assays. Accordingly, it is useful to provide non-human transgenic animals to assay in vivo sulfatase function, including peptide interaction, the effect of specific mutant sulfatases on sulfatase function and peptide interaction, and the effect of chimeric sulfatases. It is also possible to assess the effect of null mutations, that is mutations that substantially or completely eliminate one or more sulfatase functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

Sulfatase nucleic acid molecules, proteins, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo by in vivo transcription or translation of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a sulfatase protein or anti-sulfatase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can-also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin, an excipient such as starch or lactose, a disintegrating agent such as alginic acid, Primogel, or corn starch, a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. An isolated nucleic acid molecule selected from the group consisting of:
   a) a nucleic acid molecule comprising a nucleotide sequence which is at least 91% identical to the nucleotide sequence of SEQ ID NO:8, wherein the nucleic acid molecule encodes a polypeptide with sulfatase activity, or a full complement thereof; and,
   b) a nucleic acid molecule which encodes a polypeptide which is at least 91% identical to the amino acid sequence of SEQ ID NO:7, wherein the polypeptide has sulfatase activity.

2. An isolated nucleic acid molecule selected from the group consisting of:
   a) a nucleic acid molecule comprising the nucleotide sequence of SEQ ID NO:8, or a complement thereof; and
   b) a nucleic acid molecule which encodes a polypeptide comprising the amino acid sequence of SEQ ID NO:7.

3. The nucleic acid molecule of claim 1 further comprising vector nucleic acid sequences.

4. The nucleic acid molecule of claim 1 further comprising nucleic acid sequences encoding a heterologous polypeptide.

5. A host cell which contains the nucleic acid molecule of claim 3.

6. The host cell of claim 5 which is a mammalian host cell.

7. A nonhuman host cell containing the nucleic acid molecule of claim 1.

8. A method of producing a polypeptide encoded by the nucleic acid molecule of claim 1, comprising culturing the host cell containing a nucleic acid molecule comprising the nucleic acid molecule of claim 1 and vector nucleic acid sequences, under conditions in which the polypeptide encoded by the nucleic acid molecule is expressed.

9. The method of claim 8 wherein said polypeptide comprises the amino acid sequence of SEQ ID NO:7.

* * * * *